United States Patent
Van Almsick et al.

(10) Patent No.: US 6,297,196 B1
(45) Date of Patent: Oct. 2, 2001

(54) BENZOYL DERIVATIVES, PROCESS FOR THEIR PREPARATION AND THEIR USE AS HERBICIDES AND PLANT GROWTH REGULATORS

(75) Inventors: Andreas Van Almsick, Oberursel; Lothar Willms, Hofheim; Thomas Auler, Kelsterbach; Hermann Bieringer, Eppstein; Christopher Rosinger, Hofheim, all of (DE)

(73) Assignee: Hoechst Schering AgrEvo GmbH, Berlin (DE)

(*) Notice: Subject to any disclaimer, the term of this patent is extended or adjusted under 35 U.S.C. 154(b) by 0 days.

(21) Appl. No.: 09/388,905

(22) Filed: Sep. 2, 1999

(30) Foreign Application Priority Data

Sep. 4, 1998 (DE) ............................................ 198 40 337

(51) Int. Cl.[7] ...................... C07D 239/02; C07D 335/04; C07D 405/00; A01N 43/54; A01N 43/02

(52) U.S. Cl. ..................... 504/230; 564/302; 564/315; 564/408; 564/219; 564/261; 504/243; 504/242; 504/251; 504/235; 504/288; 504/283; 546/208.1; 549/208.1; 548/325; 548/127

(58) Field of Search ................................... 544/302, 315, 544/408, 219; 504/243, 242, 251, 235, 288, 283, 261, 230; 546/208.1; 549/23; 548/525, 127

(56) References Cited

U.S. PATENT DOCUMENTS

| | | | |
|---|---|---|---|
| 5,468,722 | 11/1995 | Shibata et al. | 504/282 |
| 5,723,408 | 3/1998 | Shibata et al. | 504/139 |
| 5,849,926 | 12/1998 | Shibata et al. | 548/364.4 |
| 5,863,866 | 1/1999 | Takashima et al. | 504/282 |

FOREIGN PATENT DOCUMENTS

| | | |
|---|---|---|
| 4634096 | 9/1996 | (AU) . |
| 0636622 | 2/1995 | (EP) . |
| WO 93/18031 | 9/1993 | (WO) . |
| WO 95/13275 | 5/1995 | (WO) . |
| WO 95/25099 | 9/1995 | (WO) . |
| WO 96/00008 | 1/1996 | (WO) . |
| WO 96/25413 | 8/1996 | (WO) . |
| WO 96/31507 | 10/1996 | (WO) . |
| WO 97/08164 | 3/1997 | (WO) . |
| WO 97/12885 | 4/1997 | (WO) . |
| WO 97/13765 | 4/1997 | (WO) . |
| WO 97/43270 | 11/1997 | (WO) . |
| WO 97/44340 | 11/1997 | (WO) . |

OTHER PUBLICATIONS

CAS Printout for WO 97/12885, Apr. 1997.*

* cited by examiner

*Primary Examiner*—Richard L. Raymond
*Assistant Examiner*—Hong Liu
(74) *Attorney, Agent, or Firm*—Frommer Lawrence & Haug LLP

(57) ABSTRACT

Benzoyl derivatives of the formula (I), process for their preparation and their use as herbicides and plant growth regulators are described.

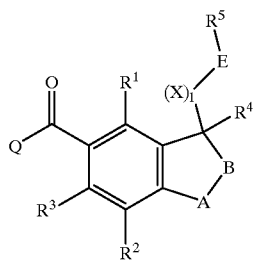

In this formula (I), $R^1$, $R^2$, $R^3$, $R^4$ and $R^5$ are various organic radicals, Q is isothiazole, isoxazole, cyclohexanedione or a β-ketonitrile radical and A, B, E and X are divalent units containing one or more atoms.

16 Claims, No Drawings

BENZOYL DERIVATIVES, PROCESS FOR THEIR PREPARATION AND THEIR USE AS HERBICIDES AND PLANT GROWTH REGULATORS

The invention relates to the technical field of the herbicides and plant growth regulators, in particular that of the herbicides for the selective control of broad-leaved weeds and weed grasses in crops of useful plants.

From various publications, it is already known that certain benzoyl derivatives have herbicidal properties. Thus, EP-A 0 712 853 and EP-A 0 841 335 describe fused benzoyl derivatives which carry an alkyl radical in the α-position of the fused-on ring system.

EP-A 0 629 623, EP-A 0 810 227 and EP-A 0 819 691 describe fused benzoyl derivatives which are substituted in the α-position of the fused-on ring system by an alkoxy radical. WO 97/23135 discloses fused benzoyl derivatives which carry a radical from the group consisting of alkyl, alkenyl, alkynyl, alkoxy and alkoxyimino in the α-position of the fused-on ring system. WO 98/29406 discloses fused benzoyl derivatives which carry one or two radicals from the group consisting of alkyl, alkoxyimino, alkoxy, alkylthio and disubstituted amino in the α-position of the fused-on ring system. Here, the three last-mentioned radicals may also be present in cyclic form, so that a cycloalkoxy, cycloalkylthio or cycloalkylamino radical is present in the α-position of the fused-on ring system. Additionally, WO 98129406 mentions a fused benzoyl derivative where a (2-tetrahydrofuryl)methyloxy radical is present in the abovementioned α-position.

Furthermore, it is known from various publications that herbicides from the group of the benzoylcyclohexanediones as inhibitors of para-hydroxyphenylpyruvate dioxygenase are based on the same mechanism of action as those from the group of the benzoylisoxazoles, cf. *J. Pesticide Sci.* 21, 473–478 (1996), *Weed Science* 45, 601–609 (1997), *Pesticide Science* 50, 83–84, (1997) and *Pesticide Outlook*, 29–32, (December 1996). Additionally, from *Pesticide Science* 50, 83–84, (1997), it is known that a benzoylisoxazole of the formula (A) can rearrange under certain conditions to give a benzoyl-3-oxopropionitrile of the formula (B).

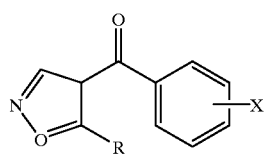

(A)

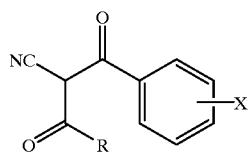

(B)

However, the use of the benzoyl derivatives known from these publications is frequently associated with disadvantages in practice. Thus, the herbicidal or plant-growth-regulating activity of the known compounds is not always sufficient, or, if the herbicidal activity is sufficient, undesirable damage to the useful plants is observed.

It is an object of the present invention to provide herbicidal and plant-growth-regulating compounds which overcome the disadvantages known from the prior art.

This object is achieved by benzoyl derivatives of the formula (I)

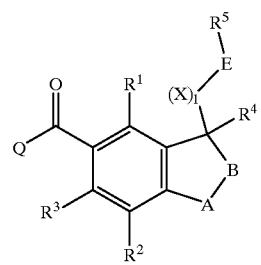

(I)

in which
Q is a radical of the formula (II), (III) or (IV)

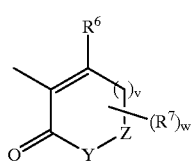

(II)

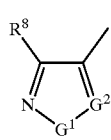

(III)

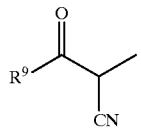

(IV)

$R^1$, $R^2$, $R^3$ independently of one another are hydrogen, hydroxyl, thio, amino, cyano, nitro, halogen or an unsubstituted or substituted hydrocarbon radical which may or may not contain one or more additional, identical or different, heteroatoms selected from the group consisting of oxygen, sulfur, nitrogen, fluorine, chlorine, bromine and iodine;

$R^4$ is hydrogen, cyano, alkyl, alkenyl, alkynyl, cycloalkyl, alkoxycarbonyl, phenyl, where the six last-mentioned groups are unsubstituted or substituted by one or more identical or different radicals selected from the group consisting of halogen, nitro, cyano, alkyl, cycloalkyl, alkenyl, alkynyl, alkoxy and alkylthio;

$R^5$ is heteroaryl, heterocylyl or aryl which is unsubstituted or mono- or polysubstituted by identical or different radicals, or is a radical selected from the group consisting of $-O-N=CR^lR^m$, $-P(=O)(OR^i)(R^j)$, $-P(=O)(OR^i)(OR^k)$ or

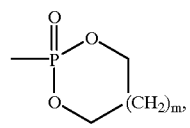

or, if E is a bond and l is zero, $R^5$ can also be hydroxyl,
A is a divalent unit selected from the group consisting of O, S, SO, $SO_2$, $NR^a$, $CHR^a$ and $CR^aR^b$;

B is a chain which comprises one to four carbon atoms, which is saturated or contains one or more multiple bonds and which is unsubstituted or substituted by alkyl, haloalkyl, alkoxy, haloalkoxy or by an unsubstituted or alkyl-, haloalkyl-, alkoxy-, haloalkoxy-, halogen-, cyano- or nitro-substituted phenyl radical;

E is a bond, a one- to six-membered chain which is saturated or contains one or more multiple bonds and which consists of divalent units selected from the group consisting of C, $CR^c$, $CR^cR^d$, N, $NR^c$, S, SO, $SO_2$, O and CO;

X is a divalent unit selected from the group consisting of O, S and $NR^e$;

$R^6$ is alkylthio, haloalkylthio, alkylsulfinyl, haloalkylsulfinyl, alkylsulfonyl, haloalkylsulfonyl, cyano, cyanato, thiocyanato, halogen or $OR^f$;

Y is a divalent unit selected from the group consisting of O, S, NH, N-alkyl or $CHR^7$;

$R^7$ is hydrogen, tetrahydropyran-3-yl, tetrahydropyran-4-yl, tetrahydrothiopyran-3-yl, alkyl, cycloalkyl, alkoxy, alkoxyalkyl, alkylcarbonyl, alkoxycarbonyl, alkylthio, phenyl, where the hydrocarbon moiety of the eight last-mentioned radicals is unsubstituted or substituted by one or more identical or different radicals selected from the group consisting of halogen, alkylthio and alkyloxy, or two radicals $R^7$ which are attached to a joint carbon atom form a chain selected from the group consisting of $OCH_2CH_2O$, $OCH_2CH_2CH_2O$, $SCH_2CH_2S$ and $SCH_2CH_2CH_2S$, this chain being unsubstituted or substituted by one to four methyl groups, or two radicals $R^7$ which are attached to directly adjacent carbon atoms form a bond or together with the carbon atoms that carry them form an unsubstituted or substituted 3- to 6-membered ring;

Z is a bond, a divalent unit selected from the group consisting of O, S, SO, $SO_2$, NH, N-alkyl or $CHR^7$, where Y and Z should not simultaneously be a divalent unit which contains an oxygen, nitrogen or sulfur atom as chain member;

$G^1$–$G^2$ is a divalent unit selected from the group consisting of $OCR^9$, $SCR^9$ and $NR^{10}COR^{11}$, where the attachment to the ring system is to be carried out such that the carbon atom of this divalent unit is in each case attached to the carbon atom of the ring system via a double bond;

$R^8$ is hydrogen, alkyl or alkoxycarbonyl;

$R^9$ is hydrogen, alkyl, cycloalkyl, haloalkyl or halocycloalkyl;

$R^{10}$ is hydrogen, alkyl, alkenyl, alkynyl, cycloalkyl, phenyl, benzyl, where the six last-mentioned groups are unsubstituted or substituted by one or more identical or different radicals selected from the group consisting of halogen, cyano, nitro and alkoxy;

$R^{11}$ is hydrogen, formyl, alkyl, haloalkyl, alkoxyalkyl or a group L-$R^{12}$;

L is a divalent unit selected from the group consisting of $SO_2$, CO, $CHR^gCO$ or $CR^gR^h$;

$R^{12}$ is alkyl, haloalkyl, alkoxy, haloalkoxy, alkylamino, dialkylamino, cycloalkyl or is phenyl which is unsubstituted or substituted by one or more identical or different radicals selected from the group consisting of cyano, nitro, alkyl, alkoxy, haloalkyl and haloalkoxy;

$R^a$ and $R^b$ independently of one another are hydrogen, halogen, cyano, nitro, formyl, alkyl, cycloalkyl, alkenyl, alkynyl, alkylcarbonyl and alkylsulfonyl, where the hydrocarbon moiety of the six last-mentioned radicals is unsubstituted or substituted by one or more identical or different radicals selected from the group consisting of halogen, nitro, cyano, alkyl, cycloalkyl, alkenyl, alkynyl, alkoxy and alkylthio;

$R^c$ and $R^d$ independently of one another are hydrogen, halogen, nitro, cyano, alkyl, haloalkyl, cycloalkyl, alkenyl, haloalkenyl, alkynyl, haloalkynyl, alkoxy, haloalkoxy, alkylthio, haloalkylthio, alkylcarbonyl, haloalkylcarbonyl, alkoxycarbonyl, haloalkoxycarbonyl, aminocarbonyl, alkylaminocarbonyl, dialkylaminocarbonyl, haloalkylcarbonylamino, alkylcarbonyl-N-alkylamino, alkylsulfonyl, alkylsulfinyl, alkylsulfonylamino, haloalkylsulfonyl, haloalkylsulfinyl, alkylsulfonylamino and alkylsulfonyl-N-alkylamino;

$R^e$ is hydrogen, formyl, alkyl, cycloalkyl, alkenyl, alkynyl, alkylcarbonyl and alkylsulfonyl, where the hydrocarbon moiety of the six last-mentioned radicals may be unsubstituted or substituted by one or more identical or different radicals selected from the group consisting of halogen, nitro, cyano, alkyl, cycloalkyl, alkenyl, alkynyl, alkoxy and alkylthio;

$R^f$ is hydrogen, alkyl, haloalkyl, alkoxyalkyl, formyl, alkylcarbonyl, alkoxycarbonyl, alkylaminocarbonyl, dialkylaminocarbonyl, alkylsulfonyl, haloalkylsulfonyl, benzoyl or phenylsulfonyl, where the aromatic moiety of the two last-mentioned radicals is unsubstituted or substituted by one or more identical or different radicals selected from the group consisting of alkyl, haloalkyl, alkoxy, haloalkoxy, halogen, cyano and nitro;

$R^g$ and $R^h$ independently of one another are hydrogen or alkyl;

$R^i$ and $R^k$ independently of one another are hydrogen or $R^j$;

$R^j$ is alkyl, alkenyl, haloalkyl, haloalkenyl, phenyl, benzyl, where these six abovementioned radicals are unsubstituted or substituted by one or more identical or different radicals selected from the group consisting of halogen, cyano, nitro, ($C_1$–$C_4$)-alkyl, ($C_1$–$C_4$)-alkoxy, halogen-($C_1$–$C_4$)-alkyl or halo-($C_1$–$C_4$)-alkoxy;

$R^l$ and $R^m$ independently of one another are hydrogen or alkyl, alkenyl, alkynyl, haloalkyl, haloalkenyl or haloalkynyl which is substituted by one or more identical or different radicals $R^1$, or $R^l$ and $R^m$ together with the carbon atom to which they are attached form a 3-, 4-, -, 6-, 7- or 8-membered saturated or partially unsaturated ring which may or may not contain one to three heteroatoms selected from the group consisting of oxygen, sulfur and nitrogen and which is unsubstituted or substituted by one or more identical or different radicals $R^1$;

l is 0 or 1;

m is 0, 1 or 2;

n is 0, 1, 2 or 3;

v is 1 or 2;

w is 0, 1, 2, 3 or 4, with the proviso that a) the compound 4-[2-tetrahydrofuryl]methyloxy-5,8-dimethyl-6-[(2,6-dioxocyclohexyl)carbonyl]-1,2,3,4-tetrahydro-1$\lambda^6$-thiochromene-1,1-dione is not embraced by the above definition and b) in $R^5$ aryl is not phenyl if E is methylene and $G^1$ in $G^1$–$G^2$ is sulfur.

Depending on external conditions, such as solvent and pH, numerous compounds of the formula (I) according to the invention can occur in different tautomeric structures.

In the case that Q is a radical of the formula (II) in which $R^6$ is hydroxyl, the following tautomeric structures are possible:

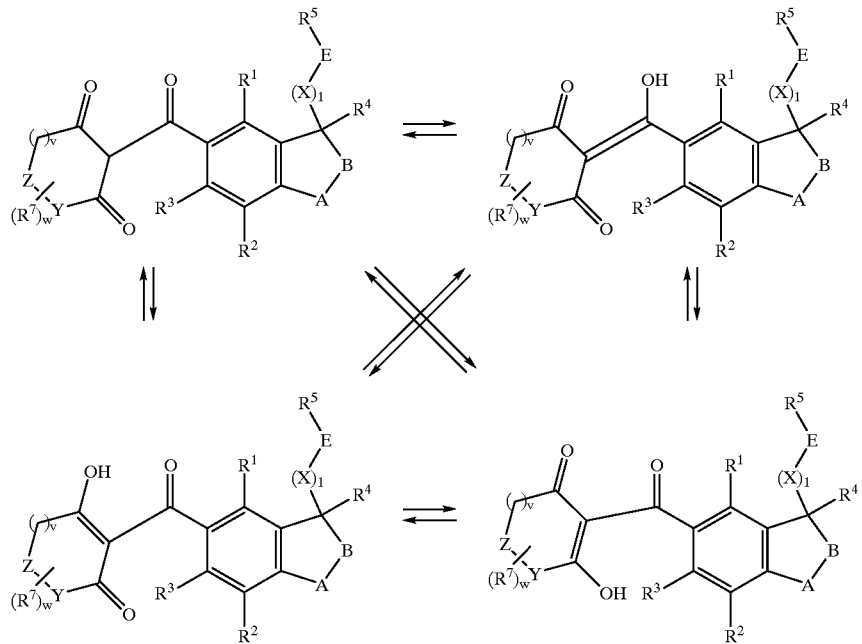

In the case that Q is a radical of the formula (IV), the following tautomeric structures are possible:

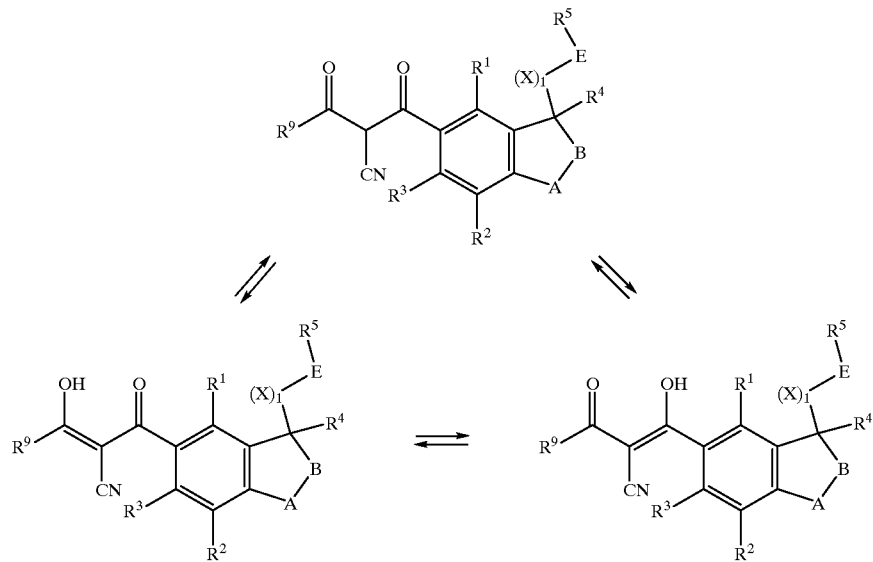

These tautomeric structures are also embraced by the formula (I).

Depending on the type of the substituents, the compounds of the formula (I) contain an acidic proton which can be removed by reaction with a base. Suitable bases are, for example, alkali metals, such as lithium, sodium and potassium, alkaline earth metals, such as calcium and magnesium, ammonia and organic amines. Such salts likewise form part of the subject matter of the invention.

A hydrocarbon radical is a straight-chain, branched or cyclic, saturated, partially saturated, unsaturated or aromatic radical, for example alkyl, alkenyl, alkynyl, cycloalkyl, cycloalkenyl, cycloalkynyl or aryl. Also embraced by this definition are composite terms, such as cycloalkylalkenyl, cycloalkynylalkyl and arylalkynyl. If this hydrocarbon radical contains additional heteroatoms, these can in principle, i.e. the chemical structure permitting, be located in any position of the hydrocarbon radical.

In the formula (I) and all subsequent formulae, hydrocarbon-containing radicals in the form of a chain, such as alkyl, alkoxy, haloalkyl, haloalkoxy, alkylamino and alkylthio, and the corresponding unsaturated and/or substituted radicals in the carbon skeleton, such as alkenyl and alkynyl, can in each case be straight-chain or branched. Unless specifically mentioned, in these radicals the lower carbon skeletons, for example those having 1 to 6 carbon atoms or, in the case of unsaturated groups, having 2 to 4 carbon atoms, are preferred. Alkyl radicals, even in the composite meanings, such as alkoxy, haloalkyl, etc., are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyls, 1-methylhexyl and 1,4-dimethylpentyl; alkenyl and alkynyl radicals have the meaning of the unsaturated radicals which correspond to the meaning of the alkyl radicals and which are possible; alkenyl is, for example, allyl, 1-methylprop-2-en-1-yl, 2-methylprop-2-en-1-yl, but-2-en-1-yl, but-3-en-1-yl, 1-methyl-but-3-en-1-yl and 1-methyl-but-2-en-1-yl; alkynyl is, for example, propargyl, but-2-yn-1-yl, but-3-yn-1-yl, 1-methylbut-3-yn-1-yl. The multiple bond may be located in any position of the unsaturated radical.

Cycloalkyl is a carbocyclic saturated ring system having three to eight carbon atoms, for example cyclopropyl, cyclopentyl or cyclohexyl. Analogously, cycloalkenyl is a monocyclic alkenyl group having three to eight carbon ring members, for example cyclopropenyl, cyclobutenyl, cyclopentenyl and cyclohexenyl, where the double bond may be in any position. In the case of composite radicals, such as cycloalkylalkenyl, the first-mentioned radical may be located in any position of the radical mentioned second.

In the case of a doubly substituted amino group, such as dialkylamino, these two radicals may be identical or different.

Halogen is fluorine, chlorine, bromine or iodine. Haloalkyl, -alkenyl and -alkynyl is alkyl, alkenyl and alkynyl, respectively, which is partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

The term heterocyclyl is to be understood as three- to six-membered saturated or partially unsaturated mono- or polycyclic heterocycles which contain one to three heteroatoms selected from a group consisting of oxygen, nitrogen and sulfur. The group may be attached at any position of the heterocycle, if chemically possible. Examples are oxiranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxoazolidinyl, 3-isothioazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxa-diazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydrofur-4-yl, 2,3-dihydrofur-5-yl, 2,5-dihydrofur-2-yl, 2,5-dihydrofur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydro-isoxazol-4-yl, 4,5-dihydroisoxazol-5-yl, 2,5-dihydroisothiazol-3-yl, 2,5-dihydroisothiazol-4-yl, 2,5-dihydroisothiazol-5-yl, 2,3-dihydroisopyrazol-3-yl, 2,3-dihydroisopyrazol-4-yl, 2,3-dihydroisopyrazol-5-yl, 4,5-dihydroisopyrazol-3-yl, 4,5-dihydroisopyrazol-4-yl, 4,5-dihydroisopyrazol-5-yl, 2,5-dihydroisopyrazol-3-yl, 2,5-dihydroisopyrazol-4-yl, 2,5-dihydroisopyrazol-5-yl, 2,3-dihydrooxazol-3-yl, 2,3-dihydrooxazol-4-yl, 2,3-dihydrooxazol-5-yl, 4,5-dihydrooxazol-3-yl, 4,5-dihydrooxazol-4-yl, 4,5-dihydrooxazol-5-yl, 2,5-dihydrooxazol-3-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 1-morpholinyl, 2-morpholinyl, 3-morpholinyl, 1-piperidinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,3-dithian-2-yl, 1,1-dioxo-2,3,4,5-tetrahydrothein-2-yl, 2H-1,4-benzothiazin-3-yl, 2H-1,4-benzoxazin-3-yl, 1,3-dihydrooxazin-2-yl.

Aryl is an aromatic mono- or polycyclic hydrocarbon radical, for example phenyl, naphthyl, biphenyl and phenanthryl. The group can be attached at any position of aryl, if chemically possible.

Heteroaryl is an aromatic mono-, bi- or tricyclic radical which, in addition to carbon ring members, contains one to four nitrogen atoms or one to three nitrogen atoms and one oxygen or one sulfur atom or one oxygen or one sulfur atom. The group can be attached at any position of aryl, if chemically possible. Examples of 5-membered heteroaryl are 2-pyrrolyl, 3-pyrrolyl, 1-pyrazolyl, 3-pyrazolyl, 4-pyrazolyl, 5-pyrazolyl, 2-imidazolyl, 4-imidazolyl, 1,2,4-triazolyl-3-yl, 1,3,4-triazol-2-yl, 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl. Examples of 6-membered heteroaryl are 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl. Examples of fused 5-membered heteroaryl are benzothiazol-2-yl and benzoxazol-2-yl. Examples of benzofused 6-membered heteroaryl are quinoline, isoquinoline, quinazoline and quinoxaline.

The definition of a divalent unit is to be understood such that the saturation may take place via single, double and/or triple bonds. The divalent unit "O" is therefore an oxygen atom which is attached via two single bonds. The divalent unit "CR$^e$" is a carbon atom which is attached via a single and a double bond and carries a radical R$^e$. The divalent unit "C" is a carbon atom which is attached via a single and a triple bond. If an unsymmetrical divalent unit is present, i.e. if two possibilities of attachment are allowed, in each case both possibilities of attaching this unit and the rest of the molecule are embraced by the formula I.

Depending on the type and the attachment of the substituents, the compounds of the formula (I) may be present as stereoisomers. If, for example, one or more alkenyl groups are present, this may lead to diastereomers. If, for example, one or more asymmetric carbon atoms are present, this may lead to enantiomers and diastereomers. Stereoisomers can be obtained from mixtures resulting in the preparation by using customary separation methods, for example chromatographic separation processes. Stereoisomers can also be prepared selectively by employing stereoselective reactions using optically active starting materials and/or auxiliaries. The invention also relates to all stereoisomers and mixtures thereof which are embraced by the formula (I) but not defined specifically.

The term "partially or fully halogenated" is meant to express that some or all of the hydrogen atoms in the groups thus characterized can be replaced by identical or different halogen atoms as mentioned above.

If a group is polysubstituted, this is to be understood such that the general principles of constructing chemical compounds have to be observed when combining the different substituents, i.e. that no compounds are formed which are known to the person skilled in the art to be chemically unstable or impossible.

Of further interest are compounds of the formula (I) in which

R$^1$, R$^2$, R$^3$ independently of one another are hydrogen, alkyl, alkenyl, alkynyl, cycloalkyl, cycloalkenyl, cycloalkylalkyl, cycloalkylalkenyl, cycloalkylalkynyl, aryl, arylalkyl, arylalkenyl, arylalkynyl, heteroaryl, heteroarylalkyl, heteroarylalkenyl, heteroarylalkynyl, heterocyclyl, heterocyclylalkyl, heterocyclylalkenyl, heterocyclylalkynyl, hydroxyl, alkoxy, alkenyloxy, alkynyloxy, cycloalkoxy, cycloalkylalkoxy, cycloalkylalkenyloxy, cycloalkylalkynyloxy, cycloalkenyloxy, aryloxy, arylalkoxy, arylalkenyloxy, arylalkynyloxy, heteroaryloxy, heteroarylalkoxy, heteroarylalkenyloxy, heteroarylalkynyloxy, heterocyclyloxy, heterocyclylalkoxy, heterocyclylalkenyloxy, heterocyclylalkynyloxy, thio, alkylthio, alkenylthio, alkynylthio, cycloalkylthio, cycloalkylalkylthio, cycloalkylalkenylthio, cycloalkylalkynylthio, cycloalkenylthio, arylthio, arylalkylthio, arylalkenylthio, arylalkynylthio, heteroarylthio, heteroarylalkylthio, heteroarylalkenylthio, heteroarylalkynylthio, heterocyclylthio, heterocyclylalkylthio, heterocyclylalkenylthio, heterocyclylalkynylthio, amino, unsubstituted or substituted mono- or dialkylamino, unsubstituted or substituted mono- or diarylamino, unsubstituted or substituted mono- or diheteroarylamino, unsubstituted or substituted N-alkyl-N-arylamino, unsubstituted or substituted N-alkyl-N-heteroarylamino, alkenylamino, alkynylamino, cycloalkylamino, cycloalkenylamino, heterocyclylalkylamino, heterocyclylalkenylamino, alkylsulfonyl, alkenylsulfonyl, alkynylsulfonyl, cycloalkylsulfonyl, cycloalkylalkylsulfonyl, cycloalkylalkenylsulfonyl, cycloalkylalkynylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynylsulfonyl, heterocyclylsulfonyl, heterocyclylalkylsulfonyl, heterocyclylalkenylsulfonyl, heterocyclylalkynylsulfonyl, alkylsulfinyl, alkenylsulfinyl, alkynylsulfinyl, cycloalkylsulfinyl, cycloalkylalkylsulfinyl, cycloalkylalkenylsulfinyl, cycloalkylalkynylsulfinyl, arylsulfinyl, arylalkylsulfinyl, arylalkenylsulfinyl, arylalkynylsulfinyl, heteroarylsulfinyl, heteroarylalkylsulfinyl, heteroarylalkenylsulfinyl, heteroarylalkynylsulfinyl, heterocyclylsulfinyl, arylalkylsulfinyl, heterocyclylalkenylsulfinyl, heterocyclylalkynylsulfinyl, aminosulfonyl, unsubstituted or substituted mono- or dialkylaminosulfonyl, unsubstituted or substituted mono- or diarylaminosulfonyl, unsubstituted or substituted mono- or diheteroarylaminosulfonyl, unsubstituted or substituted N-alkyl-N-arylaminosulfonyl, unsubstituted or substituted N-alkyl-N-heteroarylaminosulfonyl, alkylsulfonyloxy, alkenylsulfonyloxy, alkynylsulfonyloxy, cycloalkylsulfonyloxy, cycloalkylalkylsulfonyloxy, cycloalkylalkenylsulfonyloxy, cycloalkylalkynylsulfonyloxy, arylsulfonyloxy, arylalkylsulfonyloxy, arylalkenylsulfonyloxy, arylalkynylsulfonyloxy, heteroarylsulfonyloxy, heteroarylalkylsulfonyloxy, heteroarylalkenylsulfonyloxy, heteroarylalkynylsulfonyloxy, heterocyclylsulfonyloxy, heterocyclylalkylsulfonyloxy, heterocyclylalkenylsulfonyloxy, heterocyclylalkynylsulfonyloxy, alkylsulfonylamino, alkenylsulfonylamino, alkynylsulfonylamino, cycloalkylsulfonylamino, cycloalkylalkylsulfoamino, cycloalkylalkenylsulfonylamino, cycloalkylalkynylsulfonylamino, arylsulfonylamino, arylalkylsulfonylamino, arylalkenylsulfonoamino, arylalkynylsulfonylamino, heteroarylsulfonylamino, heteroarylalkylsulfonylamino, heteroarylalkenylsulfonoamino, heteroarylalkynylsulfonylamino, alkylsulfonyl-N-alkylamino, alkenylsulfonyl-N-alkylamino, alkynylsulfonyl-N-alkylamino, cycloalkylsulfonyl-N-alkylamino, cycloalkylalkylsulfonyl-N-alkylamino, cycloalkylalkenylsulfonyl-N-alkylamino, cycloalkylalkynylsulfonyl-N-alkylamino, arylsulfonyl-N-alkylamino, heteroarylsulfonyl-N-alkylamino, arylalkylsulfonyl-N-alkylamino, heteroarylalkylsulfonyl-N-alkylamino, arylalkenylsulfonoamino, heteroarylalkenylsulfonoamino, arylalkynylsulfonyl-N-alkylamino, heteroarylalkynylsulfonyl-N-alkylamino, heterocyclylsulfonyl-N-alkylamino, heterocyclylalkylsulfoamino, heterocyclylalkenylsulfonyl-N-alkylamino, heterocyclylalkynylsulfonyl-N-alkylamino, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, arylcarbonyl, arylalkylcarbonyl, arylalkenylcarbonyl, arylalkylylcarbonyl, heteroarylcarbonyl, heteroarylalkylcarbonyl, heteroarylalkenyl, heteroarylalkynylcarbonyl, heterocyclylcarbonyl, heterocyclylalkylcarbonyl, heterocyclylalkenyl, heterocyclylalkynylcarbonyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, aryloxycarbonyl, arylalkoxycarbonyl, arylalkenyloxycarbonyl, arylalkynyloxycarbonyl, heteroaryloxycarbonyl, heteroarylalkoxycarbonyl, heteroarylalkenyloxycarbonyl, heteroarylalkynyloxycarbonyl, heterocyclyloxycarbonyl, heterocyclylalkoxycarbonyl, heterocyclylalkenyloxycarbonyl, heterocyclylalkynyloxycarbonyl, aminocarbonyl, unsubstituted or substituted mono- or dialkylaminocarbonyl, unsubstituted or substituted mono- or diarylaminocarbonyl, unsubstituted or substituted mono- or diheteroarylaminocarbonyl, unsubstituted or substituted N-alkyl-N-arylaminocarbonyl, unsubstituted or substituted N-alkyl-N-heteroarylaminocarbonyl, unsubstituted or substituted alkylcarbonylamino, unsubstituted or substituted alkylcarbonyl-N-alkylamino, unsubstituted or substituted arylcarbonylamino, unsubstituted or substituted arylcarbonyl-N-arylamino, unsubstituted or substituted heteroarylcarbonylamino, unsubstituted or substituted heteroarylcarbonyl-N-heteroarylamino, unsubstituted or substituted alkylcarbonyl-N-arylamino, unsubstituted or substituted arylcarbonyl-N-alkylamino, unsubstituted or substituted alkylcarbonyl-N-heteroarylamino, unsubstituted or substituted heteroarylcarbonyl-N-alkylamino, alkoxycarbonylamino, alkenyloxycarbonylamino, alkynyloxycarbonylamino, cycloalkoxycarbonylamino, cycloalkylalkoxycarbonylamino, cycloalkylalkenyloxycarbonylamino, cycloalkylalkynyloxycarbonylamino, aryloxycarbonylamino, arylalkoxycarbonylamino, arylalkenyloxycarbonylamino, arylalkynyloxycarbonylamino, heteroaryloxycarbonylamino, heteroarylalkoxycarbonylamino, heteroarylalkenyloxycarbonylamino, heteroarylalkynyloxycarbonylamino, heterocyclyloxycarbonylamino, heterocyclylalkoxycarbonylamino, heterocyclylalkenyloxycarbonylamino, heterocyclylalkynyloxycarbonylamino, alkoxycarbonyl-N-alkylamino, alkenyloxycarbonyl-N-alkylamino, alkynyloxycarbonyl-N-alkylamino, cycloalkoxycarbonyl-N-alkylamino, cycloalkylalkoxycarbonyl-N-alkylamino, cycloalkylalkenyloxycarbonyl-N-alkylamino, cycloalkylalkynyloxycarbonyl-N-alkylamino, aryloxycarbonyl-N-alkylamino, arylalkoxycarbonyl-N-alkylamino, arylalkenyloxycarbonyl-N-alkylamino, arylalkynyloxycarbonyl-N-alkylamino, heteroarylalkoxycarbonyl-N-alkylamino, heteroarylalkenyloxycarbonyl-N-alkylamino, heteroarylalkynyloxycarbonyl-N-alkylamino, heterocyclylalkoxycarbonyl-N-alkylamino, heterocyclylalkenyloxycarbonyl-N-alkylamino, heterocyclylalkynyloxycarbonyl-N-alkylamino, formyl, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfinyl, haloalkenylsulfinyl, haloalkynylsulfinyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkenyloxycarbonylamino, haloalkynyloxycarbonylamino, alkoxyalkoxy, arylalkoxyalkoxy, cyano, nitro, or a radical selected from the group consisting of alkyl-NH—N=CH—, aryl-(CH$_2$)$_n$—NH—N=CH—, alkoxy-N=CH—, aryl-(CH$_2$)$_n$—O—N=CH—, alkyl-NH—NH—CO— and arylalkyl-NH—NH—CO— and R$^5$ is heteroaryl, heterocyclyl or aryl, each of which is unsubstituted or mono- or polysubstituted by identical or different substituents selected from the group consisting of alkyl, alkenyl, alkynyl, cycloalkyl, cycloalkenyl, cycloalkylalkyl, cycloalkylalkenyl, cycloalkylalkynyl, aryl, arylalkyl, arylalkenyl, arylalkynyl, heteroaryl, heteroarylalkyl, heteroarylalkenyl, heteroarylalkynyl, heterocyclyl, heterocyclylalkyl, heterocyclylalkenyl, heterocyclylalkynyl, hydroxyl, alkoxy, alkenyloxy, alkynyloxy, cycloalkoxy, cycloalkylalkoxy, cycloalkylalkenyloxy, cycloalkylalkynyloxy, cycloalkenyloxy, aryloxy, arylalkoxy, arylalkenyloxy, arylalkynyloxy, heteroaryloxy, heteroarylalkoxy, heteroarylalkenyloxy, heteroarylalkynyloxy, heterocyclyloxy, heterocyclylalkoxy, heterocyclylalkenyloxy, heterocyclylalkynyloxy, thio, alkylthio, alkenylthio, alkynylthio, cycloalkylthio, cycloalkylalkylthio, cycloalkylalkenylthio, cycloalkylalkynylthio, cycloalkenylthio, arylthio, arylalkylthio, arylalkenylthio, arylalkynylthio, heteroarylthio, heteroarylalkylthio, heteroarylalkenylthio, heteroarylalkynylthio, heterocyclylthio, heterocyclylalkylthio, heterocyclylalkenylthio, heterocyclylalkynylthio, amino, unsubstituted or substituted mono- or dialkylamino, unsubstituted or substituted mono- or diarylamino, unsubstituted or substituted mono- or diheteroarylamino, unsubstituted or substituted N-alkyl-N-arylamino, unsubstituted or substituted N-alkyl-N-heteroarylamino, alkenylamino, alkynylamino, cycloalkylamino, cycloalkenylamino, heterocyclylalkylamino, heterocyclylalkenylamino, alkylsulfonyl, alkenylsulfonyl, alkynylsulfonyl, cycloalkylsulfonyl, cycloalkylalkylsulfonyl, cycloalkylalkenylsulfonyl, cycloalkylalkynylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynylsulfonyl, heterocyclylsulfonyl, heterocyclylalkylsulfonyl, heterocyclylalkenylsulfonyl, heterocyclylalkynylsulfonyl, alkylsulfinyl, alkenylsulfinyl, alkynylsulfinyl, cycloalkylsulfinyl, cycloalkylalkylsulfinyl, cycloalkylalkenylsulfinyl, cycloalkylalkynylsulfinyl, arylsulfinyl, arylalkylsulfinyl, arylalkenylsulfinyl, arylalkynylsulfinyl, heteroarylsulfinyl, heteroarylalkylsulfinyl, heteroarylalkenylsulfinyl, heteroarylalkynylsulfinyl, heterocyclylsulfinyl, arylalkylsulfinyl, heterocyclylalkenylsulfinyl, heterocyclylalkynylsulfinyl, aminosulfonyl, unsubstituted or substituted mono- or dialkylaminosulfonyl, unsubstituted or substituted mono- or diarylaminosulfonyl, unsubstituted or substituted mono- or diheteroarylaminosulfonyl, unsubstituted or substituted N-alkyl-N-arylaminosulfonyl, unsubstituted or substituted N-alkyl-N-heteroarylaminosulfonyl, alkylsulfonyloxy, alkenylsulfonyloxy, alkynylsulfonyloxy, cycloalkylsulfonyloxy, cycloalkylalkylsulfonyloxy, cycloalkylalkenylsulfonyloxy, cycloalkylalkynylsulfonyloxy, arylsulfonyloxy, arylalkylsulfonyloxy, arylalkenylsulfonyloxy, arylalkynylsulfonyloxy, heteroarylsulfonyloxy, heteroarylalkylsulfonyloxy, heteroarylalkenylsulfonyloxy, heteroarylalkynylsulfonyloxy, heterocyclylsulfonyloxy, heterocyclylalkylsulfonyloxy, heterocyclylalkenylsulfonyloxy, heterocyclylalkynylsulfonyloxy, alkylsulfonylamino, alkenylsulfonylamino, alkynylsulfonylamino, cycloalkylsulfonylamino, cycloalkylalkylsulfoamino, cycloalkylalkenylsulfonylamino, cycloalkylalkynylsulfonylamino, arylsulfonylamino, arylalkylsulfonylamino, arylalkenylsulfonoamino, arylalkynylsulfonylamino, heteroarylsulfonylamino, heteroarylalkylsulfonylamino, heteroarylalkenylsulfonoamino, heteroarylalkynylsulfonylamino, alkylsulfonyl-N-alkylamino, alkenylsulfonyl-N-alkylamino, N-alkyl-alkynylsulfonyl-N-alkylamino, cycloalkylsulfonyl-N-alkylamino, cycloalkylalkylsulfonyl-N-alkylamino, cycloalkylalkenylsulfonyl-N-alkylamino, cycloalkylalkynylsulfonyl-N-alkylamino, arylsulfonyl-N-alkylamino, heteroarylsulfonyl-N-alkylamino, arylalkylsulfonyl-N-alkylamino, heteroarylalkylsulfonyl-N-alkylamino, arylalkenylsulfonyl-N-alkylamino, heteroarylalkenylsulfononyl-N-alkylamino, arylalkynylsulfonyl-N-alkylamino, heteroarylalkynylsulfonyl-N-alkylamino, heterocyclylsulfonyl-N-alkylamino, heterocyclylalkylsulfonyl-N-alkylamino, heterocyclylalkenylsulfonyl-N-alkylamino, heterocyclylalkynylsulfonyl-N-alkylamino, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenyl, heteroarylalkynylcarbonyl, heterocyclylcarbonyl, heterocyclylalkylcarbonyl, heterocyclylalkenyl, heterocyclylalkynylcarbonyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, aryloxycarbonyl, arylalkoxycarbonyl, arylalkenyloxycarbonyl, arylalkynyloxycarbonyl, heteroaryloxycarbonyl, heteroarylalkoxycarbonyl, heteroarylalkenyloxycarbonyl, heteroarylalkynyloxycarbonyl, heterocyclyloxycarbonyl, heterocyclylalkoxycarbonyl, heterocyclylalkenyloxycarbonyl, heterocyclylalkynyloxycarbonyl, aminocarbonyl, unsubstituted or substituted mono- or dialkylaminocarbonyl, unsubstituted or substituted mono- or diarylaminocarbonyl, unsubstituted or substituted mono- or diheteroarylaminocarbonyl, unsubstituted or substituted N-alkyl-N-arylaminocarbonyl, unsubstituted or substituted N-alkyl-N-heteroarylaminocarbonyl, unsubstituted or substituted alkylcarbonylamino, unsubstituted or substituted alkylcarbonyl-N-alkylamino, unsubstituted or substituted arylcarbonylamino, unsubstituted or substituted arylcarbonyl-N-arylamino, unsubstituted or substituted heteroarylcarbonylamino, unsubstituted or substituted heteroarylcarbonyl-N-heteroarylamino, unsubstituted or substituted alkylcarbonyl-N-arylamino, unsubstituted or substituted arylcarbonyl-N-alkylamino, unsubstituted or substituted alkylcarbonyl-N-heteroarylamino, unsubstituted or substituted heteroarylcarbonyl-N-alkylamino, alkoxycarbonylamino, alkenyloxycarbonylamino, alkynyloxycarbonylamino, cycloalkoxycarbonylamino, cycloalkylalkoxycarbonylamino, cycloalkylalkenyloxycarbonylamino, cycloalkylalkynyloxycarbonylamino, aryloxycarbonylamino, arylalkoxycarbonylamino, arylalkenyloxycarbonylamino, arylalkynyloxycarbonylamino, heteroaryloxycarbonylamino, heteroarylalkoxycarbonylamino, heteroarylalkenyloxycarbonylamino, heteroarylalkynyloxycarbonylamino, heterocyclyloxycarbonylamino, heterocyclylalkoxycarbonylamino, heterocyclylalkenyloxycarbonylamino, heterocyclylalkynyloxycarbonylamino, alkoxycarbonyl-N-alkylamino, alkenyloxycarbonyl-N-alkylamino, alkynyloxycarbonyl-N-alkylamino, cycloalkoxycarbonyl-N-alkylamino, cycloalkylalkoxycarbonyl-N-alkylamino, cycloalkylalkenyloxycarbonyl-N-alkylamino, cycloalkylalkynyloxycarbonyl-N-alkylamino, aryloxycarbonyl-N-alkylamino, arylalkoxycarbonyl-N-alkylamino, arylalkenyloxycarbonyl-N-alkylamino, arylalkynyloxycarbonyl-N-alkylamino, heteroarylalkoxycarbonyl-N-alkylamino, heteroarylalkenyloxycarbonyl-N-alkylamino, heteroarylalkynyloxycarbonyl-N-alkylamino, heterocyclylalkoxycarbonyl-N-alkylamino, heterocyclylalkenyloxycarbonyl-N-alkylamino, heterocyclylalkynyloxycarbonyl-N-alkylamino, formyl, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfinyl, haloalkenylsulfinyl, haloalkynylsulfinyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkenyloxycarbonylamino, haloalkynyloxycarbonylamino, alkoxyalkoxy, arylalkoxyalkoxy, cyano, nitro, or a radical selected from the group consisting of alkyl-NH—N=CH—, aryl-(CH$_2$)$_n$—NH—N=CH—, alkoxy-N=CH—, aryl-(CH$_2$)$_n$—O—N=CH—, alkyl-NH—NH—CO— and arylalkyl-NH—NH—CO— and, or is a radical selected from the group consisting of —O—N=CR$^i$R$^m$, —P(=O)(OR$^i$)(R$^j$), —P(=O)(OR$^i$)(OR$^k$) or

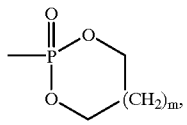

or, in the case that E is a bond and l is zero, R$^5$ may also be hydroxyl.

Of particular interest are compounds of the formula (I) in which

R$^1$, R$^2$, R$^3$ independently of one another are hydrogen, halogen, nitro, cyano, alkyl, cycloalkyl, alkenyl, alkynyl, alkoxy, alkylthio, alkylsulfinyl, alkylsulfonyl, alkylsulfonyloxy, alkylsulfonylamino, alkylsulfonyl-N-alkylamino, phenyl, benzyl, where the thirteen last-mentioned groups are unsubstituted or substituted by one or more identical or different radicals selected from the group consisting of halogen, nitro, cyano, alkyl, haloalkyl, cycloalkyl, alkenyl, alkynyl, alkoxy, haloalkoxy and alkylthio;

R$^4$ is hydrogen, cyano, alkyl, alkenyl, alkynyl, cycloalkyl, where the four last-mentioned groups are unsubstituted or substituted by one or more identical or different radicals selected from the group consisting of halogen, nitro, cyano, alkyl, cycloalkyl, alkynyl, alkoxy, alkylthio;

R$^5$ is a phenyl radical, a three-, five- or six-membered heteroaryl radical which may contain up to three heteroatoms selected from the group consisting of nitrogen, oxygen and sulfur, or a three- to six-membered saturated, partially saturated or unsaturated heterocycle radical which may contain up to four heteroatoms selected from the group consisting of nitrogen, oxygen and sulfur, each of which is unsubstituted or mono- or polysubstituted by identical or different substituents selected from the group consisting of halogen, nitro, cyano, formyl, amino, phenyl, benzyl, (C$_1$–C$_6$)-alkyl, (C$_2$–C$_6$)-alkenyl, (C$_2$–C$_6$)-alkynyl, (C$_3$–C$_6$)-cycloalkyl, (C$_1$–C$_6$)-alkoxy, (C$_1$–C$_6$)-alkylamino, di-(C$_1$–C$_6$)-alkylamino, (C$_1$–C$_6$)-alkoxycarbonyl, (C$_1$–C$_6$)-alkylaminocarbonyl, di-(C$_1$–C$_6$)-alkylaminocarbonyl, (C$_1$–C$_6$)-alkylcarbonyl, (C$_1$–C$_6$)-alkylcarbonylamino, (C$_1$–C$_6$)-alkylcarbonyl-(C$_1$–C$_6$)-alkylamino, (C$_1$–C$_6$)-alkylcarbonyl-di-(C$_1$–C$_6$)alkylamino, (C$_1$–C$_6$)-alkylthio, (C$_1$–C$_6$)-alkylsulfinyl, (C$_1$–C$_6$)-alkylsulfonyl, (C$_1$–C$_6$)-alkylsulfonylamino, (C$_1$–C$_6$)-alkylsulfonyl-(C$_1$–C$_6$)-alkylamino, (C$_1$–C$_6$)-alkylsulfonyl-di-(C$_1$–C$_6$)-alkylamino, where the 22 last-mentioned groups are unsubstituted or substituted by one or more identical or different radicals selected from the group consisting of halogen, nitro, cyano, (C$_1$–C$_6$)-alkyl, (C$_3$–C$_6$)-cycloalkyl, (C$_2$–C$_6$)-alkenyl, (C$_2$–C$_6$)-alkynyl, (C$_1$–C$_6$)-alkoxy, (C$_1$–C$_6$)-alkylthio or by a three- to six-membered saturated, partially saturated or unsaturated heterocycle which may contain up to four heteroatoms selected from the group consisting of nitrogen, oxygen and sulfur, or is a radical selected from the group consisting of —O—N=CR$^i$R$^m$, —P(=O)(OR$^i$)(R$^j$), —P(=O)(OR$^i$)(OR$^k$) or

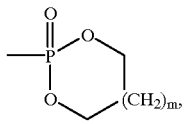

or, in the case that E is a bond and l is zero, R$^5$ may also be hydroxyl;

A is a divalent unit selected from the group consisting of S, SO, SO$_2$, and NR$^a$;

B is a chain comprising one or two carbon atoms which is saturated or contains a double bond and which is unsubstituted or substituted by alkyl, haloalkyl, alkoxy or haloalkoxy;

E is a bond, CR$^c$R$^d$, NR$^c$, S, SO, SO$_2$, O and CO;

R$^6$ is (C$_1$–C$_6$)-alkylthio, (C$_1$–C$_6$)-alkylsulfinyl, (C$_1$–C$_6$)-alkylsulfonyl, cyano, cyanato, thiocyanato, halogen or OR$^f$;

Y is a divalent unit selected from the group consisting of O, S, N—(C$_1$–C$_6$)-alkyl or CHR$^7$;

R$^7$ is hydrogen, (C$_1$–C$_6$)-alkyl, (C$_3$–C$_8$)-cycloalkyl, (C$_1$–C$_6$)-alkoxy, (C$_1$–C$_6$)-alkoxy-(C$_1$–C$_6$)-alkyl, (C$_1$–C$_6$)-alkylcarbonyl, (C$_1$–C$_6$)-alkoxycarbonyl, (C$_1$–C$_6$)-alkylthio, phenyl, where the hydrocarbon moiety of the eight last-mentioned radicals is unsubstituted or substituted by one or more identical or different radicals selected from the group consisting of halogen, (C$_1$–C$_3$)-alkylthio and (C$_1$–C$_3$)-alkyloxy;

Z is a bond, CH$_2$ or CHR$^7$;

R$^8$ is hydrogen, (C$_1$–C$_6$)-alkyl or (C$_1$–C$_6$)-alkoxycarbonyl;

R$^9$ is hydrogen, (C$_1$–C$_6$)-alkyl, (C$_3$–C$_8$)-cycloalkyl or halo-(C$_1$–C$_6$)-alkyl;

R$^{10}$ is hydrogen, (C$_1$–C$_6$)-alkyl, (C$_2$–C$_6$)-alkenyl, (C$_2$–C$_6$)-alkynyl, (C$_3$–C$_8$)-cycloalkyl, phenyl, benzyl, where the six last-mentioned radicals are unsubstituted or substituted by one or more identical or different radicals selected from the group consisting of halogen, cyano, nitro and (C$_1$–C$_6$)-alkoxy;

R$^{11}$ is hydrogen, formyl, (C$_1$–C$_6$)-alkyl, halo-(C$_1$–C$_6$)-alkyl, (C$_1$–C$_6$)-alkoxy-(C$_1$–C$_6$)-alkyl or a group L-R$^{12}$;

L is a divalent unit selected from the group consisting of SO$_2$, CO and CHR$^g$CO;

R$^{12}$ is (C$_1$–C$_6$)-alkyl, halo-(C$_1$–C$_6$)-alkyl, or phenyl which is unsubstituted or substituted by one or more identical or different radicals selected from the group consisting of cyano, nitro, (C$_1$–C$_3$)-alkyl, (C$_1$–C$_3$)-alkoxy, halo-(C$_1$–C$_3$)-alkyl and halo-(C$_1$–C$_3$)-alkoxy;

R$^a$ is hydrogen, halogen, cyano, nitro, formyl, (C$_1$–C$_6$)-alkyl, (C$_3$–C$_8$)-cycloalkyl, (C$_2$–C$_6$)-alkenyl, (C$_2$–C$_6$)-alkynyl, (C$_1$–C$_6$)-alkylcarbonyl and (C$_1$–C$_6$)-alkylsulfonyl, where the hydrocarbon moiety of the six last-mentioned radicals is unsubstituted or substituted by one or more identical or different radicals selected from the group consisting of halogen, nitro, cyano, (C$_1$–C$_6$)-alkyl, (C$_3$–C$_8$)-cycloalkyl, (C$_2$–C$_6$)-alkenyl, (C$_2$–C$_6$)-alkynyl, (C$_1$–C$_6$)-alkoxy and (C$_1$–C$_6$)-alkylthio;

R$^c$ and R$^d$ independently of one another are hydrogen, halogen, nitro, cyano, (C$_1$–C$_6$)-alkyl, halo-(C$_1$–C$_6$)-alkyl, (C$_3$–C$_8$)-cycloalkyl, (C$_2$–C$_6$)-alkenyl, halo- ($C_2$–$C_6$)-alkenyl, ($C_2$–$C_6$)-alkynyl, halo-($C_2$–$C_6$)-alkynyl, ($C_1$–$C_6$)-alkoxy, halo-($C_1$–$C_6$)-alkoxy, ($C_1$–$C_6$)-alkylthio, halo-($C_1$–$C_6$)-alkylthio, ($C_1$–$C_6$)-alkylcarbonyl, halo-($C_1$–$C_6$)-alkylcarbonyl, ($C_1$–$C_6$)-alkoxycarbonyl, halo-($C_1$–$C_6$)-alkoxycarbonyl, aminocarbonyl, ($C_1$–$C_6$)-alkylsulfonyl;

$R^e$ is hydrogen, formyl, ($C_1$–$C_6$)-alkyl, ($C_3$–$C_8$)-cycloalkyl, ($C_2$–$C_6$)-alkenyl, ($C_2$–$C_6$)-alkynyl, ($C_1$–$C_6$)-alkylcarbonyl and ($C_1$–$C_6$)-alkylsulfonyl, where the hydrocarbon moiety of the six last-mentioned radicals may be unsubstituted or substituted by one or more identical or different radicals selected from the group consisting of halogen, nitro, cyano, ($C_1$–$C_6$)-alkyl, cycloalkyl, ($C_2$–$C_6$)-alkenyl, ($C_2$–$C_6$)-alkynyl, ($C_1$–$C_6$)-alkoxy and ($C_1$–$C_6$)-alkylthio;

$R^1$ is hydrogen, ($C_1$–$C_6$)-alkyl, halo-($C_1$–$C_6$)-alkyl, ($C_1$–$C_6$)-alkylcarbonyl, ($C_1$–$C_6$)-alkoxycarbonyl, ($C_1$–$C_6$)-alkylsulfonyl, halo-($C_1$–$C_6$)-alkylsulfonyl, benzoyl or phenylsulfonyl, where the aromatic moiety of the two last-mentioned radicals is unsubstituted or substituted by one or more identical or different radicals selected from the group consisting of ($C_1$–$C_6$)-alkyl, halo-($C_1$–$C_6$)-alkyl, ($C_1$–$C_6$)-alkoxy, halo-($C_1$–$C_6$)-alkoxy, halogen, cyano and nitro;

$R^g$ and $R^h$ independently of one another are hydrogen or ($C_1$–$C_6$)-alkyl, and w is 0, 1, 2 or 3.

Preference is given to compounds of the formula I in which $R^1$, $R^2$, $R^3$ independently of one another are hydrogen, halogen, nitro, cyano, ($C_1$–$C_6$)-alkyl, ($C_3$–$C_8$)-cycloalkyl, ($C_2$–$C_6$)-alkenyl, ($C_2$–$C_6$)-alkynyl, ($C_1$–$C_6$)-alkoxy, ($C_1$–$C_6$)-alkylthio, ($C_1$–$C_6$)-alkylsulfinyl, ($C_1$–$C_6$)-alkylsulfonyl, ($C_1$–$C_6$)-alkylsulfonyloxy, ($C_1$–$C_6$)-alkylsulfonylamino, ($C_1$–$C_6$)-alkylsulfonyl-N—($C_1$–$C_6$)-alkylamino, phenyl, benzyl, where the thirteen last-mentioned groups are unsubstituted or substituted by one or more identical or different radicals selected from the group consisting of halogen, nitro, cyano, ($C_1$–$C_3$)-alkyl, halo-($C_1$–$C_3$)-alkyl, cyclopropyl, ($C_2$–$C_4$)-alkenyl, ($C_2$–$C_4$)-alkynyl, ($C_1$–$C_3$)-alkoxy, halo-($C_1$–$C_3$)-alkoxy and alkylthio;

$R^4$ is ($C_1$–$C_4$)-alkyl, hydrogen, cyano, ($C_2$–$C_4$)-alkenyl, ($C_2$–$C_4$)-alkynyl, ($C_3$–$C_6$)-cycloalkyl, where the three last-mentioned groups are unsubstituted or substituted by one or more identical or different radicals selected from the group consisting of halogen, cyano, ($C_1$–$C_3$)-alkoxy, ($C_1$–$C_3$)-alkylthio, and where the group mentioned first is unsubstituted or substituted by one or more identical or different radicals selected from the group consisting of halogen, cyano, ($C_3$–$C_6$)-cycloalkyl, ($C_1$–$C_3$)-alkoxy, ($C_1$–$C_3$)-alkylthio;

$R^5$ is a phenyl radical, a three-, five- or six-membered heteroaryl radical which may contain up to three heteroatoms selected from the group consisting of nitrogen, oxygen and sulfur, or a three- to six-membered saturated, partially saturated or unsaturated heterocycle radical which may contain up to four heteroatoms selected from the group consisting of nitrogen, oxygen and sulfur, each of which is unsubstituted or mono- or polysubstituted by identical or different substituents selected from the group consisting of halogen, nitro, cyano, formyl, amino, phenyl, benzyl, ($C_1$–$C_4$)-alkyl, ($C_2$–$C_4$)-alkenyl, ($C_2$–$C_4$)-alkynyl, ($C_3$–$C_6$)-cycloalkyl, ($C_1$–$C_4$)-alkoxy, ($C_1$–$C_4$)-alkylamino, di-($C_1$–$C_4$)-alkylamino, ($C_1$–$C_4$)-alkoxycarbonyl, ($C_1$–$C_4$)-alkylaminocarbonyl, di-($C_1$–$C_4$)-alkylamino-carbonyl, ($C_1$–$C_4$)-alkylcarbonyl, ($C_1$–$C_4$)-alkylcarbonylamino, ($C_1$–$C_4$)-alkylthio, ($C_1$–$C_4$)-alkylsulfinyl, ($C_1$–$C_4$)-alkylsulfonyl or is a radical selected from the group consisting of —O—N=$CR^iR^m$, —P(=O)($OR^i$)($R^j$), —P(=O)($OR^i$)($OR^k$) or

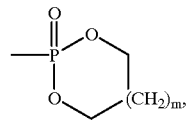

or, in the case that E is a bond and l is zero, $R^5$ may also be hydroxyl,

A is a divalent unit selected from the group consisting of S, SO, and $SO_2$;

B is a chain comprising one or two carbon atoms which is saturated or contains a double bond and which is unsubstituted or substituted by one or two identical or different radicals selected from the group consisting of ($C_1$–$C_3$)-alkyl, halo-($C_1$–$C_3$)-alkyl, ($C_1$–$C_3$)-alkoxy or halo-($C_1$–$C_3$)-alkoxy;

E is a bond, $CR^cR^d$, $SO_2$ and CO;

$R^6$ is ($C_1$–$C_3$)-alkylthio, ($C_1$–$C_3$)-alkylsulfonyl, cyano, cyanato, thiocyanato, halogen or $OR^f$;

Y is a divalent unit selected from the group consisting of O and $CHR^7$;

$R^7$ is hydrogen, ($C_1$–$C_6$)-alkyl, ($C_3$–$C_8$)-cycloalkyl, ($C_1$–$C_6$)-alkoxy-($C_1$–$C_6$)-alkyl, ($C_1$–$C_6$)-alkylcarbonyl, ($C_1$–$C_6$)-alkoxycarbonyl, phenyl, where the six last-mentioned radicals are unsubstituted or substituted by one or more identical or different halogen atoms;

$R^9$ is ($C_1$–$C_6$)-alkyl, ($C_3$–$C_6$)-Cycloalkyl or halo-($C_1$–$C_6$)-alkyl;

$R^{10}$ is ($C_1$–$C_6$)-alkyl, ($C_2$–$C_6$)-alkenyl, ($C_2$–$C_6$)-alkynyl, ($C_3$–$C_8$)-cycloalkyl, phenyl or benzyl;

$R^{11}$ is hydrogen, ($C_1$–$C_6$)-alkyl or a group $L-R^{12}$;

$R^c$ and $R^d$ independently of one another are hydrogen, ($C_1$–$C_3$)-alkyl, halo-($C_1$–$C_3$)-alkyl, ($C_2$–$C_6$)-alkenyl, halo-($C_2$–$C_6$)-alkenyl, ($C_2$–$C_6$)-alkynyl, halo($C_2$–$C_6$)-alkynyl, ($C_1$–$C_3$)-alkoxy, halo-($C_1$–$C_3$)-alkoxy, ($C_1$–$C_3$)-alkylthio, halo-($C_1$–$C_3$)-alkylthio and ($C_1$–$C_3$)-alkylcarbonyl;

$R^f$ is hydrogen, ($C_1$–$C_6$)-alkyl, ($C_1$–$C_6$)-alkylcarbonyl, ($C_1$–$C_6$)-alkoxycarbonyl, ($C_1$–$C_6$)-alkylsulfonyl, benzoyl or phenylsulfonyl, where the aromatic moiety of the two last-mentioned radicals is unsubstituted or substituted by one or more identical or different radicals selected from the group consisting of ($C_1$–$C_6$)-alkyl, halo-($C_1$–$C_6$)-alkyl, ($C_1$–$C_6$)-alkoxy, halo-($C_1$–$C_6$)-alkoxy, halogen, cyano and nitro, and w is 0, 1 or 2.

Preference is also given to compounds of the formula I in which Q is a radical of the formula (II) or (III)

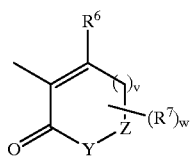

(II)

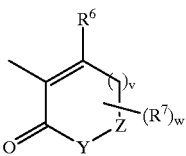

(II)

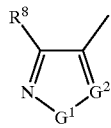

(III)

Particular preference is given to compounds of the formula I in which $R^1$ and $R^2$ independently of one another are hydrogen, $(C_1-C_4)$-alkyl, halogen or nitro;

$R^3$ and $R^4$ are hydrogen;

A is $SO_2$;

B is $CH_2-CH_2$;

E is a bond or a divalent unit selected from the group consisting of $CH_2$, CO and $SO_2$;

$R^6$ is $OR^f$;

Y is $CHR^7$;

Z is $CHR^7$;

$G^1-G^2$ is a divalent unit selected from the group consisting of $OCR^9$ and $NR^{10}COR^{11}$;

$R^7$ is hydrogen or $(C_1-C_6)$-alkyl;

$R^8$ is hydrogen;

$R^9$ is $(C_3-C_6)$-cycloalkyl;

$R^{10}$ is $(C_1-C_3)$-alkyl;

$R^{11}$ is hydrogen or a group $L-R^{12}$;

L is a divalent unit selected from the group consisting of $SO_2$, CO and $CH_2CO$;

$R^{12}$ is phenyl which is unsubstituted or substituted by one or more identical or different radicals selected from the group consisting of halogen, cyano, nitro, $(C_1-C_6)$-alkyl, $(C_1-C_6)$-alkoxy, $(C_1-C_6)$-haloalkyl and $(C_1-C_6)$-haloalkoxy;

$R^e$ is hydrogen, formyl, $(C_1-C_6)$-alkyl, $(C_2-C_6)$-alkenyl, $(C_2-C_6)$-alkynyl, $(C_1-C_6)$-alkylcarbonyl and $(C_1-C_6)$-alkylsulfonyl;

$R^f$ is hydrogen, $(C_1-C_6)$-alkylsulfonyl, benzoyl, phenylsulfonyl, where the two last-mentioned radicals are unsubstituted or substituted by one or more identical or different radicals selected from the group consisting of $(C_1-C_6)$-alkyl, $(C_1-C_6)$-haloalkyl, $(C_1-C_6)$-alkoxy, $(C_1-C_6)$-haloalkoxy, halogen, cyano and nitro, and v is 1.

Very particular preference is given to compounds of the formula I in which Q is a radical of the formula (II)

Very particular preference is also given to compounds of the formula I in which $R^5$ is a phenyl radical, a three-, five- or six-membered heteroaryl radical which may contain up to three heteroatoms selected from the group consisting of nitrogen, oxygen and sulfur, or a three- to six-membered partially saturated or unsaturated heterocycle radical which may contain one, two, three or four heteroatoms selected from the group consisting of nitrogen, oxygen and sulfur, each of which is unsubstituted or mono- or polysubstituted by identical or different substituents selected from the group consisting of halogen, nitro, cyano, formyl, amino, phenyl, benzyl, $(C_1-C_4)$-alkyl, $(C_2-C_4)$-alkenyl, $(C_2-C_4)$-alkynyl, $(C_3-C_6)$-cycloalkyl, $(C_1-C_4)$-alkoxy, $(C_1-C_4)$-alkylamino, di-$(C_1-C_4)$-alkylamino, $(C_1-C_4)$-alkoxycarbonyl, $(C_1-C_4)$-alkylaminocarbonyl, di-$(C_1-C_4)$-alkylaminocarbonyl, $(C_1-C_4)$-alkylcarbonyl, $(C_1-C_4)$-alkylcarbonylamino, $(C_1-C_4)$-alkylthio, $(C_1-C_4)$-alkylsulfinyl, $(C_1-C_4)$-alkylsulfonyl.

Depending on the meaning of the substituents, the compounds according to the invention can be prepared, for example, starting from the compound of the formula (Ia), which is known or can be prepared by known methods, according to one or more of the processes shown in the schemes below.

Scheme 1 shows the acid-catalyzed reaction of the compound of the formula (Ic) with ethanediol, which gives the compound of the formula (Id). The subsequent reaction with n-butyllithium or magnesium, carbon dioxide and the following treatment with acid gives the compound of the formula (Ie) in which R is OH. Such reactions are known, for example, from J. Org. Chem. 55, 773 (1990). By customary esterification methods, this compound can be converted into the corresponding esters of the formula (Ie) in which R is alkoxy. In all formulae below, the substituents have the same meanings as mentioned for formula (I), unless stated otherwise.

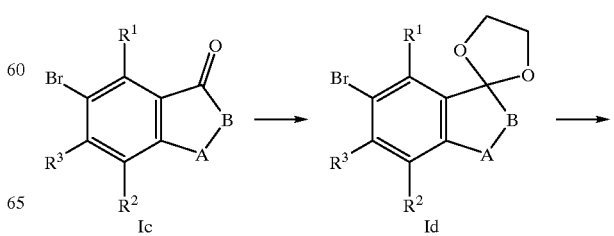

-continued

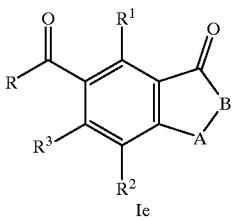

Ie

Compounds of the formula (Ie) in which R is alkoxy can be functionalized on the benzo-fused carbonyl group according to Scheme 2 by a large number of reactions. Such reactions are known, for example, from Houben-Weyl, "Methoden der organischen Chemie" [Methods of Organic Chemistry], volume 7, part 2b, Georg-Thieme Verlag, Stuttgart, 1965.

Scheme 2:

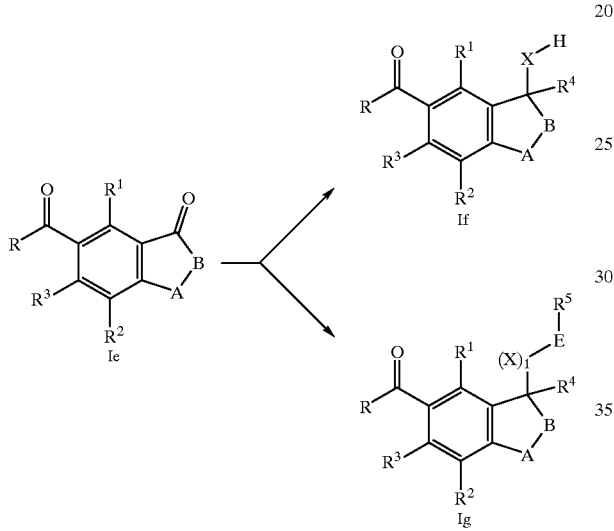

2.1 The reaction with reducing agents such as $NaBH_4$ leads to compounds of the formula (If) in which X is oxygen and $R^4$ is hydrogen.
2.2 The reaction with Grignard reagents leads to compounds of the formula (If) in which X is oxygen and $R^4$ is alkyl, alkenyl, alkynyl, cycloalkyl or phenyl.
2.3 The reaction with $Me_3SiCN$ or $Me_3SiCF_3$ leads to compounds of the formula (If) in which X is oxygen and $R_4$ is CN or $CF_3$.
2.4 The reaction with alkali metal cyanides in the presence of ammonium chloride leads to compounds of the formula (If) in which X is NH and $R_4$ is CN.
2.5 The reaction with $NaBH_3CN$ in the presence of ammonium acetate leads to compounds of the formula (If) in which X is NH and $R_4$ is hydrogen.
2.6 The reaction with $P_4S_{10}$ and, subsequently, with Grignard reagents leads to compounds of the formula (If) in which X is sulfur and $R^4$ is alkyl, alkenyl, alkynyl, cycloalkyl or phenyl.
2.7 The reaction with $H_2N$—E—$R^5$ and subsequent reduction leads to compounds of the formula (Ig) in which $(X)_l$ is NH and $R^4$ is hydrogen.
2.8 The reaction with $H_2N$—E—$R^5$ and subsequent reaction with Grignard reagents leads to compounds of the formula (Ig) in which $(X)_l$ is NH and $R^4$ is CN.
2.9 The reaction with $H_2N$—E—$R^5$ and KCN likewise leads to compounds of the formula (Ig) in which $(X)_l$ is NH and $R_4$ is CN.

2.10 The reaction with $(R^iO)(R^kO)(O=)PCN$ in the presence of LiCN in THF leads to compounds of the formula (Ig) in which l is zero and E is a bond, $R^4$ is CN and $R^5$ is $P(=O)(ORi)(OR^k)$.

Compounds of the formula (Ig) as shown in Scheme 3 are also obtainable from compounds of the formula (If) in which R is alkoxy. Such reactions are known, for example, from *J. Med. Chem.* 28, 1817, (1985), *Tetrahedron Lett.* 1699, (1986) and *Acta Chem. Scand.* B32, 452 (1978).

Scheme 3:

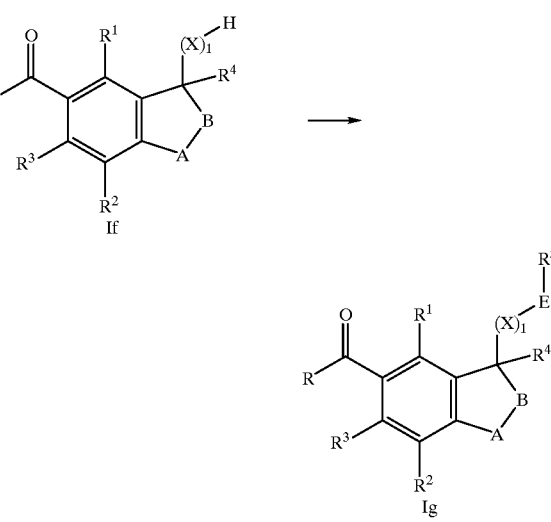

3.1 The reaction with chlorinating agents such as thionyl chloride and, subsequently, with an amine of the formula $HNR^a$—E—$R^5$ leads to compounds of the formula (Ig) in which $(X)^l$ is $NR^a$ and $R^4$ is hydrogen.
3.2 The reaction with chlorinating agents such as thionyl chloride and, subsequently, with an alcohol of the formula HO—E—$R^5$ leads to compounds of the formula (Ig) in which $(X)^l$ is oxygen and $R^4$ is hydrogen.
3.3 The reaction with chlorinating agents such as thionyl chloride and, subsequently, with a thioalcohol of the formula HS—E—$R^5$ leads to compounds of the formula (Ig) in which $(X)^l$ is sulfur and $R^4$ is hydrogen.
3.4 The reaction with a halide, triflate or mesylate leads to compounds of the formula (Ig) in which $(X)^l$ is oxygen and $R^4$ is hydrogen.
3.5 The reaction with a carboxylic acid in the presence of dehydrating agents such as DCC leads to compounds of the formula (Ig) in which $(X)^l$ is oxygen, E is CO and $R^4$ is hydrogen.
3.6 The reaction with chlorinating agents such as $CCl_4/PPh_3$ and, subsequently, with $P(OR^i)_3$ leads to compounds of the formula (Ig) in which l is zero and E is a bond, $R^4$ is hydrogen and $R^5$ is $P(=O)(OR^i)(OR^k)$.
3.7 The reaction with chlorinating agents such as $CCl_4/PPh_3$ and, subsequently, with NaCN in a solvent such as DMF or DMSO leads to a compound (Ig), in which $R^5$ is cyano, which can be reacted, by derivatizations known to the person skilled in the art, to give other compounds (Ig) in which $R^5$ is —COOH, —COOR, —COCl, -CH=NOH or —CHO. Starting from these last-mentioned compounds (Ig), it is possible, by reactions known to the person skilled in the art, to prepare compounds of the formula (I) according to the invention in which $R^5$ is heteroaryl or heterocyclyl, each of which is attached via a carbon atom.
3.8 The reaction with chlorinating agents such as $CCl_4/PPh_3$ and, subsequently, base-catalyzed with a heteroaromatic or heterocycle which has a nitrogen ring atom which carries a hydrogen atom leads to compounds of the formula (Ig) in which I is zero and E is a bond, $R^4$ is hydrogen and $R^5$ is heteroaryl or heterocyclyl attached via a nitrogen atom.

3.9 The reaction with chlorinating agents such as oxalyl chloride or $CCl_4/PPh_3$ and, subsequently, with a compound HO—N=$R^kR^l$ in the presence of a base such as NaH in a suitable solvent such as THF, DMF or DMSO leads to compounds of the formula (Ig) in which (X)l—E together represents a bond, $R^4$ is hydrogen and $R^5$ is —O—N=$R^kR^l$.

The reaction of a compound of the formula (Ig) with a compound of the formula (IIa) shown in scheme 4 gives compounds of the formula Ia' in which Q is a radical of the formula (II). To this end, the compound of the formula (Ig) is reacted with (IIa) either in the presence of dehydrating agents such as DCC, or, after conversion into its acyl chloride, base-catalyzed, and subsequently treated with a source of cyanide. These methods are described, for example, in EP-A 0 369 803 and EP-B 0 283 261. In these formulae and the formulae below, R is alkoxy.

Scheme 4:

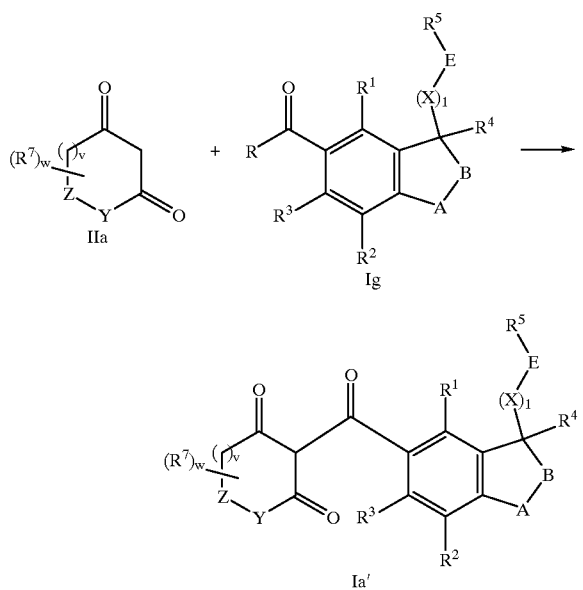

The reaction of a compound of the formula (Ig) with a hydroxypyrazole of the formula (IIIa) shown in Scheme 5 gives compounds according to the invention in which Q is a radical of the formula (III) and $G^1$–$G^2$ is $NR^{10}OCR^{11}$. To this end, the compound of the formula (Ig) is reacted with (IIIa) either in the presence of dehydrating agents such as DCC or, after conversion into its acid chloride, base-catalyzed, and subsequently treated with a source of cyanide. These methods are described, for example, in EP-A 0 369 803. The radical $R^{11}$ is introduced on the pyrazole ring by known reactions such as esterification, alkylation or acylation.

Scheme 5:

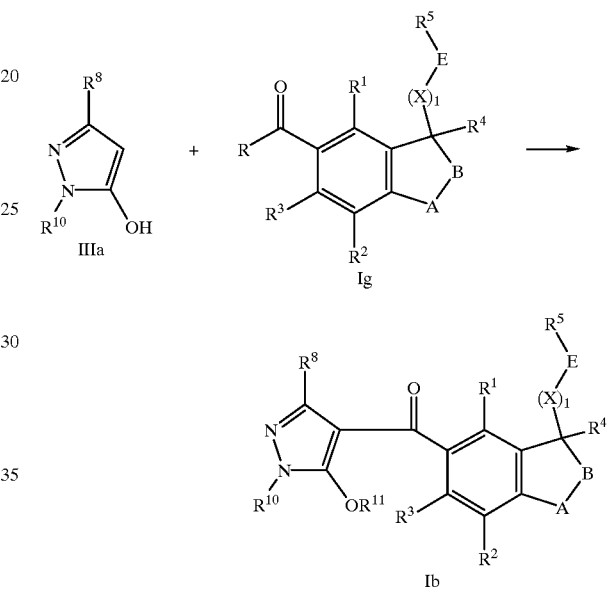

The reaction of a compound of the formula (Ig) with a β-ketoester shown in Scheme 6 and subsequent acidic cleavage gives a compound of the formula (Ih) which is converted by reaction with an orthocarboxylic ester or a carboxamide acetal into a compound of the formula (Ii) in which $L^1$ is a leaving group such as ethoxy or N,N-dimethylamino. Finally, by base-catalyzed reaction with hydroxylamine, the compounds (Ib'), according to the invention in which Q is a radical of the formula (III) and $G^1$–$G^2$ is $OCR^9$ are obtained.

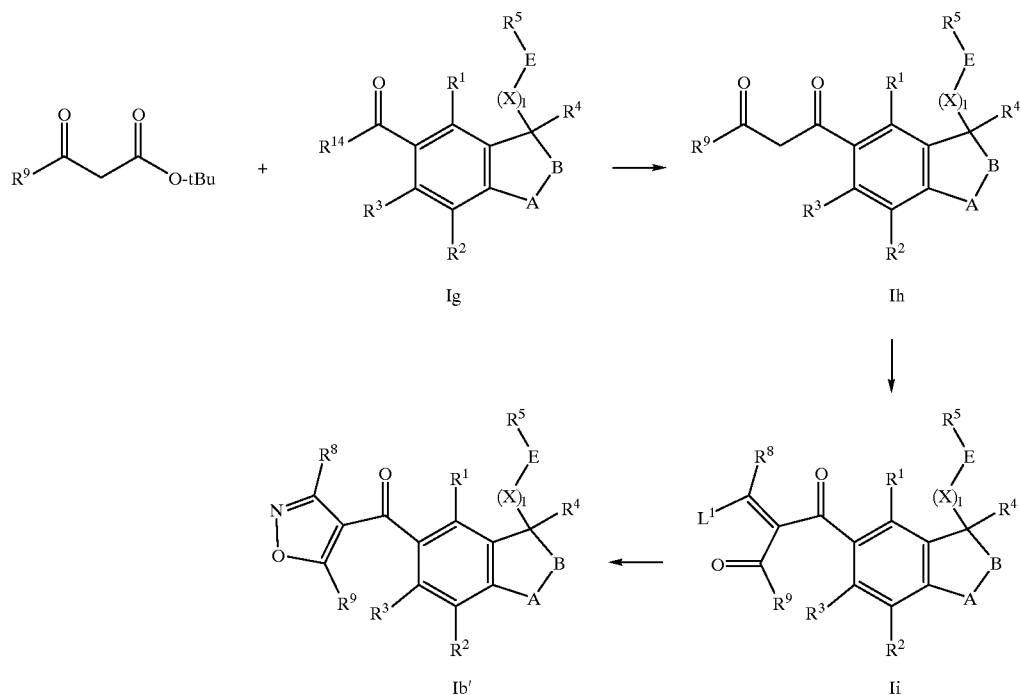

The reaction of a compound of the formula (Ig) in the presence of magnesium, an organomagnesium compound or an organolithium compound with a halogen-substituted isothiazole, which can be prepared, for example, according to methods in *Synth. Commun.* 17, 1207 (1987), shown in Scheme 7, gives compounds (Ib″) according to the invention in which Q is a radical of the formula (III) and $G^1$–$G^2$ is $SCR^9$.

Scheme 7

-continued

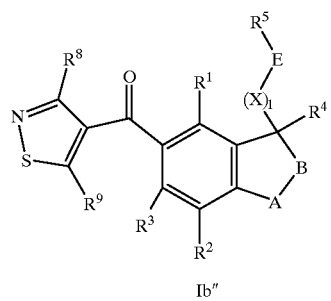

The base-catalyzed reaction of a compound of the formula (Ig), in which R is chlorine with a β-ketonitrile of the formula (IVa) shown in Scheme 8 gives compounds (Ic) according to the invention in which Q is a radical of the formula (IVI). The reaction is carried out, for example, analogously to the methods known from EP-A 0 213 892 and EP-A 0 496 631.

Scheme 8

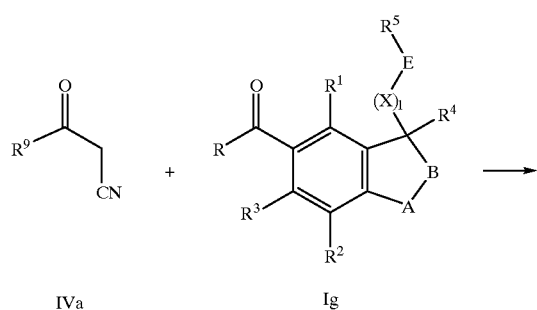

IVa          Ig

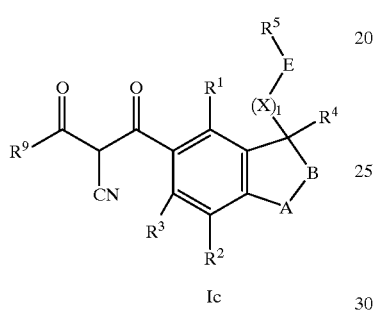

Ic

The reaction of a compound of the formula (Ia') with a halogenating agent such as oxalyl chloride or oxalyl bromide shown in Scheme 9 leads to compounds of the formula (Ia") according to the invention which can be converted by reaction, if appropriate with basetalysis, with nucleophiles, such as alkali metal cyanides, alkali metal cyanates, alkali metal thiocyanates, alkyl thioalcohols and thiophenols to give other compounds of the formula (Ia) according to the invention. Such reactions are described, for example in *Synthesis* 12, 1287 (1992).

Scheme 9

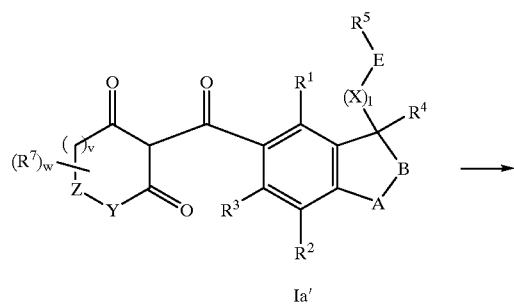

Ia'

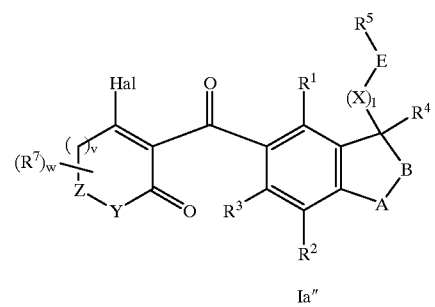

Ia"

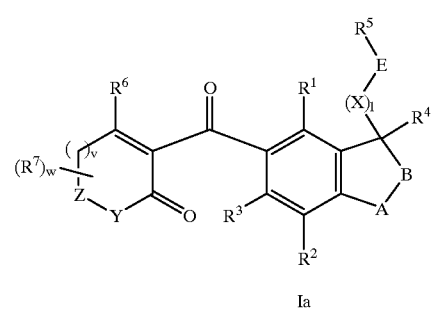

Ia

Compounds of the formula (If) in which A is sulfur can be oxidized according to Scheme 10 using suitable oxidizing agents such as peroxyacetic acid, hydrogen peroxide, m-chloroperbenzoic acid and potassium peroxymonosulfate to give the corresponding compounds in which, depending on the amount of the oxidizing agent employed, A is SO or $SO_2$. Such reactions are known, for example, from *J. Org. Chem.* 53, 532 (1988) and can also be applied to other compounds mentioned here.

Scheme 10

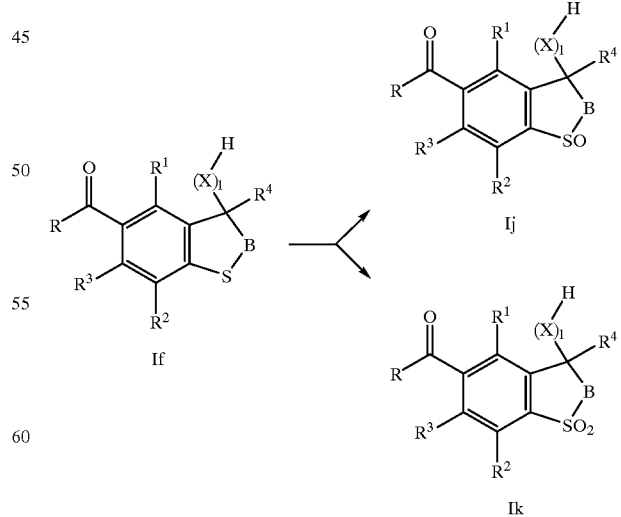

The invention also provides compounds of the formula (Ig),

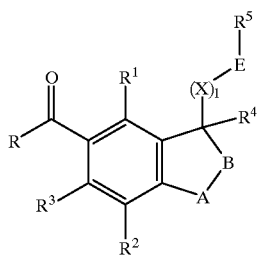

in which
R is $(C_1-C_6)$-alkyl,
$R^4$ is hydrogen,
$R^5$ is COOH, COOR, COCl, CH=NOH, CHO,
E is a bond,
l is 0
and $R^1$, $R^2$, $R^3$, A and B have the meanings given under the formula (I).

The compounds of the formula (I) according to the invention have an outstanding herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is generally immaterial whether the substances are applied pre-sowing, pre-emergence or post-emergence. Specifically, examples may be mentioned of some representatives of the monocotyledonous and dicotyledonous weed flora which can be controlled by the compounds according to the invention, without these being a restriction to certain species.

Examples of weed species on which the active compounds act efficiently are, from amongst the monocotyledons, Avena, Lolium, Alopecurus, Phalaris, Echinochloa, Digitaria, Setaria and also Cyperus species from the annual sector and from amongst the perennial species Agropyron, Cynodon, Imperata and Sorghum, and also perennial Cyperus species.

In the case of the dicotyledonous weed species, the spectrum of action extends to species such as, for example, Galium, Viola, Veronica, Lamium, Stellaria, Amaranthus, Sinapis, lpomoea, Matricaria, Abutilon and Sida from amongst the annuals, and Convolvulus, Cirsium, Rumex and Artemisia in the case of the perennial weeds.

The active ingredients according to the invention also effect outstanding control of harmful plants which occur under the specific conditions of rice growing such as, for example, Echinochloa, Sagittaria, Alisma, Eleocharis, Scirpus and Cyperus. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely.

If the active compounds are applied post-emergence to the green parts of the plants, growth also stops drastically a very short time after the treatment and the weed plants remain at the developmental stage of the point in time of application, or they die completely after a certain time, so that in this manner competition by the weeds, which is harmful to the crop plants, is eliminated at a very early point in time and in a sustained manner.

Although the compounds according to the invention have an excellent herbicidal activity against monocotyledonous and dicotyledonous weeds, crop plants of economically important crops such as, for example, wheat, barley, rye, rice, corn, sugarbeet, cotton and soya, are not damaged at all, or only to a negligible extent. For these reasons, the present compounds are highly suitable for selectively controlling undesired plant growth in plantings for agricultural use or in plantings of ornamentals.

Owing to their herbicidal and plant growth-regulatory properties, the active compounds can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested product are known.

The use of the compounds of the formula (I) according to the invention or their salts in economically important transgenic crops of useful and ornamental plants, for example of cereal, such as wheat, barley, rye, oats, millet, rice, maniok and corn, or else in crops of sugarbeet, cotton, soya, rapeseed, potato, tomato, pea and other vegetable species is preferred.

The compounds of the formula (I) can preferably be used as herbicides in crops of useful plants which are resistant or which have been made resistant by genetic engineering toward the phytotoxic effects of the herbicides.

Conventional ways of preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases of genetically engineered changes in crop plants in order to modify the starch synthesized in the plants (for example WO 92/11376, WO 92/14827, WO 91/19806), transgenic crop plants which are resistant to certain herbicides of the glufosinate-(cf., for example, EP-A 0 242 236, EP-A 0 242 246) or glyphosate-type (WO 92/00377), or of the sulfonylurea-type (EP-A 0 257 993, US. Pat. No. 5,013,659), transgenic crop plants, for example cotton, having the ability to produce *Bacillus thuringiensis* toxins (Bt toxins) which impart resistance to certain pests to the plants (EP-A 0 142 924, EP-A 0 193 259), transgenic crop plants having a modified fatty acid composition (WO 91113972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim, 2nd edition 1996, or Christou, "Trends in Plant Science" 1 (1996) 423–431).

In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product.

To this end, it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells can be regenerated to whole plants using known techniques. The transgenic plants can in principle be plants of any desired plant species, i.e. both monocotyledonous and dicotyledonous plants.

In this manner, it is possible to obtain transgenic plants which have modified properties by overexpression, suppression or inhibition of homologous (=natural) genes or gene sequences or by expression of heterologous (=foreign) genes or gene sequences.

The compounds according to the invention can preferably be used in transgenic crops which are resistant to herbicides from the group consisting of the sulfonylureas, glufosinate-ammonium or glyphosate-isopropylammonium and analogous active compounds.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants.

The invention therefore also provides for the use of the compounds according to the invention as herbicides for controlling harmful plants in transgenic crop plants.

In addition, the substances according to the invention have outstanding growth-regulating properties in crop plants. They engage in the plant metabolism in a regulating manner and can thus be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledonous and dicotyledonous crops because lodging can be reduced hereby, or prevented completely.

The compounds according to the invention can be applied in the customary formulations in the form of wettable powders, emulsifiable concentrates, sprayable solutions, dusts or granules. The invention therefore also provides herbicidal and plant growth-regulating compositions comprising compounds of the formula (I).

The compounds of the formula (I) can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes.

These individual formulation types are known in principle and are described, for example, in Winnacker-Küchler, "Chemische Technologie" [Chemical Technology], Volume 7, C. Hauser Verlag Munich, 4th edition 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation auxiliaries, such as inert materials, surfactants, solvents and other additives, are likewise known and are described, for example, in: Watkins, "Handbook of Insecticide Dust Diluents and Carriers", 2nd ed., Darland Books, Caldwell N.J., H. v. Olphen, "Introduction to Clay Colloid Chemistry"; 2nd ed., J. Wiley & Sons, N.Y.; C. Marsden, "Solvents Guide"; 2nd ed., lnterscience, N.Y. 1963; McCutcheon's "Detergents and Emulsifiers Annual", MC Publ. Corp., R'dgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag Munich, 4th edition 1986.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ethersulfates, alkanesulfonates, alkylbenzenesulfonates, sodium ligninsulfonate, sodium 2,2'-dinaphthylmethane-6,6'-disulfonate, sodium dibutyinaphthalenesulfonate or else sodium oleoylmethyltaurinate. To prepare the wettable powders, the herbicidally active compounds are finely ground, for example in customary apparatus such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth.

Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers.

Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th ed., McGraw-Hill, New York 1973, pp. 8–57.

For further details on the formulation of crop protection products, see for example G. C. Klingman, "Weed Control as a Science", John Wiley and Sons., Inc., New York, 1961, pages 81–96 and J. D. Freyer, S. A. Evans, "Weed Control Handbook", 5th ed., Blackwell Scientific Publications, Oxford, 1968, pages 101–103.

The agrochemical formulations generally contain from 0.1 to 99% by weight, in particular from 0.1 to 95% by weight, of active compound of the formula (I).

In wettable powders the concentration of active compound is, for example, from about 10 to 90% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules, the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, said formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Suitable active compounds which can be combined with the active compounds according to the invention in mixed formulations or in a tank mix are, for example, known active compounds as described, for example, in Weed Research 26, 441–445 (1986), or "The Pesticide Manual", 11th edition, The British Crop Protection Council and the Royal Soc. of Chemistry, 1997 and in the literature cited therein. For example, the following active ingredients may be mentioned as herbicides which are known from the literature and which can be combined with the compounds of the formula (I) (note: the compounds are either referred to by the "common name" in accordance with the International Organization for Standardization (ISO) or by the chemical names, if appropriate together with a customary code number): acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazine; azimsulfurone (DPX-A8947); aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, i.e. 2-chloro-N,N-di-2-propenylacetamide; CDEC, i.e. 2-chloroalkyl diethyldithiocarbamate; chlomethoxyfen; chloramben; chlorazifop-butyl; chlormesulan (ICI-A0051); chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butyl ester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone; clomazon; dimethipin; dimetrasulfuron; dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4(3-fluoropropyl)-4,5-dihydro-5-oxo-1H-tetrazol-1-yl]-phenyl] ethanesulfonamide; ethoxyfen and its esters (for example ethyl ester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentyl ester, S-23031); flumioxazin (S482); flumipropyn; flupoxam (KNW-739); fluorodifen; fluoroglycofen-ethyl; flupropacil (UBIC4243); fluridone; flurochloridone; fluroxypyr; flurtamone; fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazamethabenz-methyl; imazapyr; imazaquin and salts such as the ammonium salt; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metabenzuron; methobenzuron; metobromuron; metolachlor; metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)-phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulfentrazon (FMC-97285, F6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazol-1-carboxamide; thenylchlor (NSK-850); thiazafluron; thiazopyr (Mon-13200); thidiazimin (SN-24085); thifensulfuron-methyl; thiobencarb; tiocarbazil; tralkoxydim; tri-allate; triasulfuron; triazofenamide; tribenuronmethyl; triclopyr; tridiphane; trietazine; trifluralin; triflusulfuron and its esters (for example methyl ester, DPX66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH4127 and KIH-2023.

For use, the formulations which are present in commercially available form are, if appropriate, diluted in the customary manner, for example using water in the case of wettable powders, emulsifiable concentrates, dispersions and water-dispersible granules. Preparations in the form of dusts, granules for soil application or broadcasting and sprayable solutions are usually not further diluted with other inert substances prior to use.

The application rate of the compounds of the formula (I) required varies with the external conditions, such as temperature, humidity, the nature of the herbicide used and the like. It can vary within wide limits, for example between 0.001 and 10.0 kg/ha or more of active substance, but it is preferably between 0.005 and 5 kg/ha.

A. CHEMICAL EXAMPLES

1. Preparation of 4-{[3-chloro-5-(trifluoromethyl)-2-pyridyl]oxy}-5,8-dimethyl-6-[(2,6-dioxocyclohexyl)carbonyl]-1,2,3,4-tetrahydro-1$\lambda^6$-thiochromene-1,1-dione Step 1: 3-[(2,5-Dimethylphenyl)thio]propanoic acid 90 g (2.25 mol) of sodium hydroxide were dissolved in 500 ml of water and, with cooling at 10° C., admixed with 147.59 g of 2,5-dimethylthiophenol. Cooling was continued and 180.1 g (1.18 mol) of 3-bromopropionic acid were added below 25° C. The mixture was stirred for another 4 h at room temperature and then washed with diethyl ether (3×500 ml). The aqueous solution was made acidic using 1M HCl, and the precipitated product was filtered off and washed with water.

Yield: 205.88 g (92% of theory); colorless crystals, m.p.: 97–98° C. $R_f$=0.56 (silica gel/ethylacetate); $^1$H NMR (CDCl$_3$): δ 2.3 (s, 3H), 2.34 (s, 3H), 2.68 (t, 2H), 3.1 (t, 2H), 6.9 (d, 1H), 7.06–7.14 (2H).

Step 2: 5,8-Dimethyl-4-thiochromanone

At −10° C., 100 g (0.48 mol) of 3-[(2,5-dimethylphenyl)thio]propanoic acid were dissolved in 2200 ml of conc. sulfuric acid. The reaction solution was stirred at room temperature for 1 h and then poured onto crushed ice. The aqueous solution was extracted with a diethyl ether/hexane mixture (1:9) (6×500 ml). The combined organic phases were dried over MgSO$_4$ and concentrated completely using a rotary evaporator.

Yield: 56.63 g (62% of theory); yellowish oil, $R_f$=0.63 (silica gel/ethyl acetate); $^1$H NMR (CDCl$_3$): δ 2.3 (s, 3H), 2.6 (s, 3H), 2.97 (m, 2H), 3.2 (m, 2H), 6.9–7.1 (2H).

Step 3: 6-Bromo-5,8-dimethyl-4-thiochromanone 66.5 g (0.35 mol) of 5,8-dimethyl-4-thiochromanone, together with 118 g (0.87 mol) of aluminum chloride, were dissolved or suspended in 600 ml of methylene chloride. After 15 min of stirring, 62.2 g (0.39 mol) of bromine were slowly added dropwise, and the reaction mixture was subsequently boiled under reflux for 10 min. The reaction mixture, which was still warm, was poured into 220 ml of conc. hydrochloric acid in crushed ice. The mixture was stirred for 10 min, the methylene chloride phase was separated off and the aqueous phase was extracted with diethyl ether (3×400 ml). The combined organic phases were washed with water, dried over MgSO$_4$ and concentrated using a rotary evaporator.

Yield: 58.4 g (62% of theory); brownish crystals, m.p.: 87–88° C. (after chromatographic purification) $R_f$=0.78 (silica gel/ethyl acetate); $^1$H NMR (CDCl$_3$): δ 2.3 (s, 3H), 2.6 (s, 3H), 3.0 (m, 2H), 3.2 (m, 2H), 7.45(2H).

Step 4: 6-Bromo-5,8-dimethylspiro[thiochromane-4,2'-[1,3]dioxolane]

58.4 g (0.22 mol) of 6-bromo-5,8-dimethyl-4-thiochromanone were dissolved in 380 ml of trimethyl orthoformate, admixed with 555 g (8.9 mol) of ethanediol and 0.2 g of p-toluenesulfonic acid monohydrate and stirred at 80° C. overnight. The mixture was subsequently allowed to cool, diluted with 500 ml of diethyl ether and washed with a 1:1 mixture of 1 M aqueous sodium hydroxide solution and sat. NaCl solution (2×500 ml) and subsequently with sat. NaCl solution (300 ml). The organic phase was dried over MgSO$_4$ and concentrated using a rotary evaporator. The residue was taken up in 50 ml of heptane/diethyl ether (9:1) and stored in a cold place. The crystals which had precipitated overnight were filtered off with suction, washed with cold heptane and dried.

Yield: 46.38 g (68% of theory); brownish crystals, m.p.: 97° C.; R$_f$=0.75 (silica gel/ethyl acetate); $^1$H NMR (CDCl$_3$): δ 2.2 (s, 3H), 2.3 (m, 2H), 2.4 (s, 3H), 3.0 (m, 2H), 4.15 (m, 2H, 4.3 (m, 2H), 7.3 (s, 1H).

Step 5: 5,8-Dimethyl-4-oxo-6-thiochromanecarboxylic acid 46.38 g (0.15 mol) of 6-bromo-5,8-dimethylspiro [thiochromane-4,2'-[1,3]dioxolane] were dissolved in 500 ml of tetrahydrofuran and cooled to −65° C. 80 ml (0.2 mol) of 2.5 M n-butyllithium in hexane were subsequently slowly added dropwise such that the temperature did not exceed −55° C. The mixture was stirred for another 1 h, and 90 g of dry ice were then added a little at a time. The solution was subsequently allowed to warm to room temperature, 500 ml of hexane were added and the precipitate was filtered off with suction. The precipitate was taken up in 500 ml of water and made strongly acidic using conc. hydrochloric acid. The mixture was boiled under reflux for 1 h and then allowed to cool, and the precipitated product was filtered off with suction.

Yield: 26.18 g (75% of theory); colorless crystals, m.p.: 146–148° C. $^1$H NMR (Me$_2$SO-d6): δ 2.2 (s, 3H), 2.5 (s, 3H), 2.9 (m, 2H), 3.3 (m, 2H), 7.6 (s, 1H).

Step 6: Methyl 5,8-dimethyl-4-oxo-4-thiochromanecarboxylate 26.17 g (0.11 mol) of 5,8-dimethyl-4-oxo-6-thiochromanecarboxylic acid were dissolved in 500 ml of methanol, admixed with 3 ml of conc. sulfuric acid and boiled under reflux. At regular intervals, a total of another 3 ml of conc. sulfuric acid were added until, after 3 days, no more starting material could be detected by thin-layer chromatography (SiO$_2$, ethyl acetate). The mixture was allowed to cool, the methanol was stripped off using a rotary evaporator and the residue was taken up in 400 ml of ethyl acetate. The mixture was washed with sat. NaCl solution (2×100 ml) and sat. NaHCO$_3$ solution (2×100 ml), dried over MgSO$_4$ and concentrated using a rotary evaporator.

Yield: 24.96 g (90% of theory); brown oil, R$_f$=0.7 (silica gel/ethyl acetate);

$^1$H NMR (CDCl$_3$): δ 2.2 (s, 3H), 2.6 (s, 3H), 3.0 (m, 2H), 3.2 (m, 2H), 3.85 (s, 3H), 7.6 (s, 1H).

Step 7: Methyl 5,8-dimethyl-4-hydroxy-6-thiochromanecarboxylate 10.40 g (0.04 mol) of methyl 5,8-dimethyl-4-oxo-6-thiochromanecarboxylate were dissolved in 200 ml of ethanol and, a little at a time, admixed with 0.89 g (0.023 mol) of sodium borohydride. The mixture was subsequently stirred at room temperature for another 1 h and then concentrated using a rotary evaporator. The residue was taken up in 200 ml of ethyl acetate, washed with sat. NaCl solution (2×100 ml), dried over MgSO$_4$ and concentrated using a rotary evaporator.

Yield: 10.3 g (98% of theory); brown oil; R$_f$=0.6 (silica gel/ethyl acetate); $^1$H NMR (CDCl$_3$): δ 1.8 (m, 1H), 2.2 (s, 3H), 2.5 (m, 1H), 2.6 (s, 3H), 2.8 (m, 1H), 3.3 (m, 1H), 3.85 (s, 3H), 5.1 (s, br, 1H), 7.6 (s, 1H).

Step 8: Methyl 5,8-dimethyl-4-hydroxy-1,1-dioxo-1,2,3,4-tetrahydro-1λ$^6$-thiochromene-6-carboxylate 10 g (0.04 mol) of methyl 5,8-dimethyl-4-hydroxy-6-thiochromanecarboxylate and 4.9 g (0.06 mol) of sodium acetate were together added to 200 ml of methanol. The mixture was cooled to 0° C. and slowly admixed with a solution of 41.4 g (0.07 mol) of OXONE® (potassium peroxymonosulfate) in 200 ml of water. During the addition, the reaction temperature was kept below 6° C. The mixture was subsequently stirred at room temperature for 4 h and then diluted with 120 ml of water. The mixture was extracted with methylene chloride (3×200 ml), and the extract was dried over MgSO$_4$ and concentrated using a rotary evaporator.

Yield: 10.6 g (94% of theory); colorless crystals; m.p.: 135–136° C.; R$_f$=0.55 (silica gel/ethyl acetate); $^1$H NMR (CDCl$_3$): δ 2.5 (m, 2H), 2.6 (s, 3H), 2.7 (s, 3H), 3.2 (s, 1H), 3.9 (m, 1H), 3.9 (s, 3H), 5.1 (m, 1H), 7.55 (s, 1H).

Step 9: Methyl 4-{[3-chloro-5-(trifluoromethyl)-2-pyridyl] oxy}-5,8-dimethyl-1,1-dioxo-1,2,3,4-tetrahydro-1λ$^6$-thiochromene-6-carboxylate 0.48 g (1.7 mmol) of methyl 5,8-dimethyl-4-hydroxy-1, 1-dioxo-1,2,3,4-tetrahydro-1λ$^6$-thiochromene-6-carboxylate and 0.4 g (1.9 mmol) of 2,5-dichloro-3-(trifluoromethyl)pyridine were dissolved in 20 ml of tetrahydrofuran and subsequently admixed with 0.21 g (1.9 mmol) of potassium tert-butoxide. The mixture was stirred for 3 h and subsequently concentrated using a rotary evaporator. The residue was taken up in 100 ml of ethyl acetate, washed with sat. NaCl solution (2×20 ml), dried over MgSO$_4$ and concentrated using a rotary evaporator. The residue was purified by chromatography (silica gel, ethyl acetate: heptane=1:3).

Yield: 0.64 g (80% of theory); yellow crystals; R$_f$=0.71 (silica gel/ethyl acetate); $^1$H NMR (CDCl$_3$): δ 2.35 (s, 3H), 2.8 (m, 2H), 2.8 (s, 3H), 3.25 (s, 1H), 3.8 (m, 1H), 3.9 (s, 3H), 6.6 (m, 1H), 7.7 (s, 1H), 7.95 (m, 1H), 8.4 (m, 1H).

Step 10: 4-{[3-Chloro-5-(trifluoromethyl)-2-pyridyl]oxy}-5,8-dimethyl-1,1-dioxo-1,2,3,4-tetrahydro-1λ$^6$-thiochromene-6-carboxylic acid 0.62 g (1.3 mmol) of methyl 5,8-dimethyl-4-hydroxy-1, 1-dioxo-1,2,3,4-tetrahydro-1λ$^6$-thiochromene-6-carboxylate was dissolved in 10 ml of tetrahydrofuran and subsequently admixed with 0.17 g (4 mmol) of sodium hydroxide in 5 ml of water. The mixture was boiled under reflux for 3 h, the tetrahydrofuran was subsequently stripped off using a rotary evaporator and the residue was made acidic using 5 M HCl. The mixture was subsequently extracted with ethyl acetate and the extract was dried over MgSO$_4$ and concentrated using a rotary evaporator.

Yield: 0.56 g (93% of theory); colorless crystals; R$_f$=0.25 (silica gel/ethyl acetate); $^1$H NMR (CDCl$_3$): δ 2.35 (s, 3H), 2.8 (m, 2H), 2.8 (s, 3H), 3.25 (s, 1H), 3.8 (m, 1H), 6.6 (m, 1H), 7.9 (s, 1H), 7.95 (m, 1H), 8.4 (m, 1H).

Step 11: 3-Oxo-1-cyclohexenyl 4-{[3-chloro-5-(trifluoromethyl)-2-pyridyl]oxy}-5,8-dimethyl-1,1-dioxo-1, 2,3,4-tetrahydro-1λ$^6$-thiochromene-6-carboxylate 0.56 g (1.2 mmol) of 4-{[3-chloro-5-(trifluoromethyl)-2-pyridyl]oxy}-5,8-dimethyl-1,1-dioxo-1,2,3,4-tetrahydro-1λ$^6$-thiochromene-6-carboxylic acid in 30 ml of methylene chloride was admixed with 2 drops of N,N-dimethylformamide and 0.48 g (3.8 mmol) of oxalyl chloride, and the mixture was boiled under reflux for 3.5 h. The solvents were subsequently stripped off using a rotary evaporator and the residue was taken up in 100 ml of methylene chloride and, at 0° C., admixed with 0.15 g (1.4 mmol) of cyclohexanedione and 0.22 g (3.7 mmol) of triethylamine. The mixture was stirred at room temperature for 4 h and subsequently concentrated using a rotary evaporator, and the residue was purified by chromatography (silica gel, ethyl acetate: hexane=1:1).

Yield: 0.39 g (58% of theory); colorless crystals; $R_f$=0.69 (silica gel/ethyl acetate); $^1$H NMR (CDCl$_3$): δ 2.1 (m, 2H), 2.4 (s, 3H), 2.45 (m, 2H), 2.65 (m, 2H), 2.8 (m, 2H), 2.8 (s, 3H), 3.25 (s, 1H), 3.8 (m, 1H), 6.0 (s, 1H), 6.7 (m, 1H), 7.85 (s, 1H), 7.95 (m, 1H), 8.4 (m, 1H).

Step 12: 4-{[3-Chloro-5-(trifluoromethyl)-2-pyridyl]oxy}-5,8-dimethyl-6-[(2,6-dioxocyclohexyl)carbonyl]-1,2,3,4-tetrahydro-1λ$^6$-thiochromene-1,1-dione 0.31 g (0.57 mmol) of 3-oxo-1-cyclohexenyl 4-{[3-chloro-5-(trifluoromethyl)-2-pyridyl]oxy}-5,8-dimethyl-1,1-dioxo-1,2,3,4-tetrahydro-1λ$^6$-thiochromene-6-carboxylate, 1 drop of acetone cyanohydrin and 0.1 g (1 mmol) of triethylamine were dissolved in 15 ml of acetonitrile, and the mixture was stirred at room temperature overnight. The mixture was subsequently concentrated using a rotary evaporator, and the residue was admixed with 5 ml of water and made acidic using 5 M HCl. The precipitated product was filtered off with suction and dried.

Yield: 0.27 g (87% of theory); colorless crystals; m.p.: 128–132° C.; $R_f$=0.37 (silica gel/ethyl acetate); $^1$H NMR (CDCl$_3$): δ 2.0 (m, 2H), 2.0 (s, 3H), 2.4 (m, 2H), 2.8 (m, 2H), 2.8 (m, 2H), 2.8 (s, 3H), 3.25 (s, 1H), 3.8 (m, 1H), 6.6 (m, 1H), 7.0 (s, 1H), 7.9 (m, 1H), 8.4 (m, 1H).

2. Preparation of 6-[(2,6-dioxocyclohexyl)carbonyl]-5,8-dimethyl-4-(2-pyrimidinyloxy)-1,2,3,4-tetrahydro-1λ$^6$-thiochromene-1,1-dione 0.38 g (0.86 mmol) of 3-oxo-1-cyclohexenyl 5,8-dimethyl-4-(2-pyrimidinyloxy)-1,1-dioxo-1,2,3,4-tetrahydro-1λ$^6$-thiochromene-6-carboxylate, 1 drop of acetone cyanohydrin and 0.1 g (1 mmol) of triethylamine were dissolved in 15 ml of acetonitrile and stirred at room temperature overnight. The mixture was subsequently concentrated using a rotary evaporator, and the residue was admixed with 5 ml of water and made acidic using 5 M HCl. The precipitated product was filtered off with suction and dried.

Yield: 0.28 g (74% of theory); beige crystals; m.p.: 96–99° C.; $R_f$=0.1 (silica gel/ethyl acetate); $^1$H NMR (CDCl$_3$): δ 2.0 (m, 2H), 2.05 (s, 3H), 2.55 (m, 4H), 2.75 (s, 3H), 2.8 (m, 2H), 3.2 (m, 1H), 3.9 (m, 1H), 6.4 (m, 1H), 7.0 (s, 1H), 7.05 (t, 2H), 8.6 (d, 2H).

3. Preparation of 6-[(2,6-dioxocyclohexyl)carbonyl]-4-benzoyloxy-5,8-dimethyl-1,2,3,4-tetrahydro-1λ$^6$-thiochromene-1,1-dione Step 1: 4-Benzoyloxy-5,8-dimethyl-1,1-dioxo-1,2,3,4-tetrahydro-1λ$^6$-thiochromene-6-carboxylic acid 1.0 g (4.1 mmol) of 5,8-dimethyl-4-hydroxy-1,1-dioxo-1,2,3,4-tetrahydro-1λ$^6$-thiochromene-6-carboxylic acid, 0.58 g (4.1 mmol) of benzoyl chloride and a spatula tip of N,N-4-dimethylaminopyridine was stirred in 10 ml of pyridine overnight. The mixture was subsequently poured onto 5 M HCl in crushed ice and extracted with ethyl acetate. The organic phase was washed with 1 M HCl (2×20 ml) and sat. NaCl solution (2×40 ml), dried over MgSO$_4$ and concentrated using a rotary evaporator.

Yield: 0.81 g (52% of theory); colorless crystals; $R_f$=0.1 (silica gel/ethyl acetate); $^1$H NMR (CDCl$_3$): δ 2.4 (s, 3H), 2.7 (m, 2H), 2.8 (s, 3H), 3.2 (s, 1H), 3.9 (m, 1H), 6.4 (s, 1H), 7.4 (m, 2H), 7.6 (m, 1H), 7.8 (s, 1H), 8.0 (m, 2H).

Step 2: 3-Oxo-1-cyclohexenyl 4-benzoyloxy-5,8-dimethyl-1,1-dioxo-1,2,3,4-tetrahydro-1λ$^6$-thiochromene-6-carboxylate 0.80 g (2.1 mmol) of 4-benzoyloxy-5,8-dimethyl-1,1-dioxo-1,2,3,4-tetrahydro-1λ$^6$-thiochromene-6-carboxylic acid in 30 ml of methylene chloride was admixed with 2 drops of N,N-dimethylformamide and 1.69 g (13.3 mmol) of oxalyl chloride, and the mixture was boiled under reflux for 3.5 h. The solvents were subsequently stripped off using a rotary evaporator, and the residue was taken up in 100 ml of methylene chloride and, at 0° C., admixed with 0.25 g (2.2 mmol) of cyclohexanedione and 0.44 g (7.4 mmol) of triethylamine. The mixture was stirred at room temperature for 4 h and subsequently concentrated using a rotary evaporator, and the residue was purified by chromatography (silica gel, ethyl acetate: hexane=1:1).

Yield: 0.37 g (25% of theory); colorless crystals; $R_f$=0.7 (silica gel/ethyl acetate); $^1$H NMR (CDCl$_3$): δ 2.1 (m, 2H), 2.4 (s, 3H), 2.45 (m, 2H), 2.65 (m, 2H), 2.8 (m, 2H), 2.8 (s, 3H), 3.35 (s, 1H), 3.8 (m, 1H), 6.0 (s, 1H), 6.2 (m, 1H), 7.45 (m, 2H), 7.6 (m, 1H), 7.8 (s, 1H), 8.0 (m, 2H).

Step 3: 6-[(2,6-Dioxocydohexyl)carbonyl]-4-benzoyloxy-5,8-dimethyl-1,2,3,4-tetrahydro-1λ$^6$-thiochromene-1,1-dione 0.37 g (0.79 mmol) of 3-oxo-1-cyclohexenyl 4-benzoyloxy-5,8-dimethyl-1,1-dioxo-1,2,3,4-tetrahydro-1λ$^6$-thiochromene-6-carboxylate, 1 drop of acetone cyanohydrin and 0.14 g (1.4 mmol) of triethylamine were dissolved in 15 ml of acetonitrile, and the mixture was stirred at room temperature overnight. The mixture was subsequently concentrated using a rotary evaporator, and the residue was admixed with 5 ml of water and made acidic using 5 M HCl. The precipitated product was filtered off with suction and dried.

Yield: 0.27 g (73% of theory); colorless crystals; $R_f$=0.1 (silica gel/ethyl acetate); $^1$H NMR (CDCl$_3$): δ 2.0 (m, 2H), 2.05 (s, 3H), 2.4 (m, 4H), 2.8 (s, 3H), 2.8 (m, 2H), 3.3 (s, 1H), 3.9 (m, 1H), 6.4 (m, 1H), 7.0 (s, 1H), 7.4 (m, 2H), 7.6 (m, 1H), 8.0 (m, 2H).

The examples listed in the tables below were prepared analogously to the methods mentioned above, or they are obtainable analogously to the methods mentioned above.

The meanings of the abbreviations used in the tables are:

| | | |
|---|---|---|
| Bz = benzoyl | Me = methyl | Et = ethyl |
| Ph = phenyl | Pr = propyl | c = cyclo |
| i = iso | d = doublet | m = multiplet |
| q = quintet | s = singlet | m.p. = melting point |
| $R_t$ = Retention | | |

TABLE 1

Compounds of the formula (I) in which the substituents and the indices are as defined below:

A = SO$_2$  B = CH$_2$—CH$_2$  R$^3$ = H
R$^4$ = H  R$^6$ = OH  Q = Radical of formula (II)
Y = CH$_2$  Z = CH$_2$  w = 0
v = 1

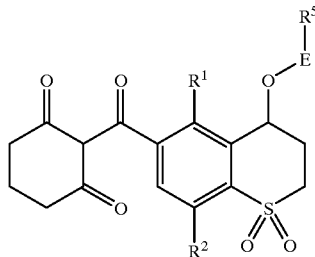

| No. | R$^1$ | R$^2$ | R$^5$ | E | Physical data |
|---|---|---|---|---|---|
| 4 | Me | Me | 2,6-dimethoxypyrimidin-4-yl (OMe, N, N, Me, OMe) | bond | $^1$H NMR(CDCl$_3$): δ2.0(m, 2H), 2.05(s, 3H), 2.55(m, 4H), 2.75 (s, 3H), 2.8(m, 2H), 3.2(s, 1H), 3.9 (m, 1H), 3.9(s, 6H), 5.8(s, 1H), 6.4 (m, 1H), 7.0(s, 1H) |
| 5 | Me | Me | 2,4,6-trimethylpyrimidin-5-yl | bond | R$_f$ = 0.1(SiO$_2$/ethyl acetate) $^1$H NMR(CDCl$_3$): δ2.0(m, 2H), 2.05(s, 3H), 2.4(s, 6H), 2.55 (m, 4H), 2.75(s, 3H), 2.8(m, 2H), 3.2 (s, 1H), 3.9(m, 1H), 3.9(s, 6H), 6.5 (m, 1H), 6.8(s, 1H), 7.0(s, 1H) |
| 6 | Me | Me | 5-chloro-3-trifluoromethyl-6-methylpyridin-2-yl | bond | m.p.: 128–130° C. $^1$H-NMR(CDCl$_3$): δ2.0(m, 2H), 2.0 (s, 3H), 2.4(m, 2H), 2.75(s, 3H), 2.8 (m, 4H), 3.2(s, 1H), 3.75(m, 1H), 6.6 (m, 1H), 7.0(s, 1H), 7.9(m, 1H) 8.35 (m, 1H) |
| 7 | Me | Me | 5-nitro-6-methylpyridin-2-yl | bond | m.p.: 185–186° C. $^1$H NMR(CDCl$_3$): δ2.0(m, 2H), 2.0(s, 3H), 2.4(m, 2H), 2.75(s, 3H), 2.8(m, 4H), 3.25(s, 1H), 3.75 (m, 1H), 6.6(m, 1H), 6.9(d, 1H), 7.0 (s, 1H), 8.4(m, 1H), 9.1(d, 1H) |
| 8 | Me | Me | 3,6-bis(trifluoromethyl)-2-methylpyridin-... | bond | m.p.: 190–195° C. $^1$H NMR(CDCl$_3$): δ1.95 (m, 2H), 2.0(s, 3H), 2.5(m, 4H), 2.75 (s, 3H), 2.8(m, 2H), 3.25(s, 1H), 3.7 (m, 1H), 6.7(m, 1H), 7.0(s, 1H), 7.45 (d, 1H), 8.1(d, 1H) |
| 9 | Me | Me | 3-chloro-2-methylpyridin-... | bond | $^1$H NMR(CDCl$_3$): δ2.0(m, 2H), 2.0(s, 3H), 2.4(m, 2H), 2.75(s, 3H), 2.8(m, 4H), 3.25(s, 1H), 3.7(m, 1H), 6.6(m, 1H), 6.9(m, 1H), 7.0(s, 1H), 7.65(m, 1H), 8.1(m, 1H) |
| 10 | Me | Me | 5-cyano-6-methylpyridin-2-yl | bond | $^1$H NMR(CDCl$_3$): δ2.0(m, 2H), 2.0(s, 3H), 2.4(m, 2H), 2.75(s, 3H), 2.8(m, 4H), 3.25(s, 1H), 3.8(m, 1H), 6.6(m, 1H), 6.75(m, 1H), 7.0(s, 1H), 7.8(m, 1H), 8.45(m, 1H) |

TABLE 1-continued

Compounds of the formula (I) in which the substituents and the indices are as defined below:

A = SO$_2$   B = CH$_2$—CH$_2$   R$^3$ = H
R$^4$ = H    R$^6$ = OH          Q = Radical of formula (II)
Y = CH$_2$   Z = CH$_2$          w = 0
v = 1

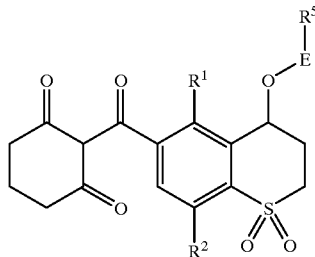

| No. | R$^1$ | R$^2$ | R$^5$ | E | Physical data |
|---|---|---|---|---|---|
| 11 | Me | Me | 2-methylpyrazinyl | bond | m.p.: 200–201° C. $^1$H NMR(CDCl$_3$): δ2.0(m, 2H), 2.0(s, 3H), 2.4(m, 2H), 2.75(s, 3H), 2.8(m, 4H), 3.25(s, 1H), 3.8(m, 1H), 6.4(m, 1H), 7.0(s, 1H), 8.15(m, 1H), 8.2(m, 1H), 8.25(m, 1H) |
| 12 | Me | Me | phenyl | CH$_2$ | $^1$H NMR(CDCl$_3$): δ2.0(m, 2H), 2.2(s, 3H), 2.4(m, 2H), 2.55(m, 1H), 2.7(s, 3H), 2.8(m, 2H), 2.9(s, 1H), 3.2(s, 1H), 3.9(m, 1H), 4.55(d, 1H), 4.65(d, 1H), 4.8(s, 1H) 6.95(s, 1H), 7.3(m, 5H) |
| 13 | Me | Me | 3-fluoro-2-methylpyridinyl | CH$_2$ | $^1$H NMR(CDCl$_3$): δ2.0(m, 2H), 2.2(s, 3H), 2.4(m, 2H), 2.55(m, 1H), 2.7(s, 3H), 2.8(m, 2H), 2.9(s, 1H), 3.2(s, 1H), 3.9(m, 1H), 4.65(m, 1H), 4.85(m, 1H), 4.8(s, 1H), 6.95 (s, 1H), 7.3(m, 1H), 7.4(m, 1H), 8.4 (m, 1H) |

TABLE 1a

Precursors of the compounds in Table 1

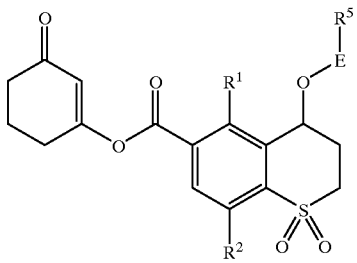

| No. | R$^1$ | R$^2$ | R$^5$ | E | Physical data |
|---|---|---|---|---|---|
| 2a | Me | Me | 2-methylpyrimidinyl | bond | $^1$H NMR(CDCl$_3$) δ2.1(m, 2H) 2.4(s, 3H), 2.45(m, 2H) 2.7 (m, 2H), 2.8(s, 3H), 2.85(m, 2H), 3.3(m, 1H), 3.9(m, 1H), 6.0(s, 1H) 6.5(m, 1H), 7.05(t, 1H), 7.8 (s, 1H), 8.6(d, 2H) |

TABLE 1a-continued

Precursors of the compounds in Table 1

| No. | R¹ | R² | R⁵ | E | Physical data |
|---|---|---|---|---|---|
| 4a | Me | Me | 2-methyl-4,6-dimethoxypyrimidin-5-yl | bond | $^1$H NMR(CDCl$_3$): δ2.15(m, 2H), 2.4(s, 3H), 2.45(m, 2H), 2.7 (m, 2H), 2.75(m, 1H), 2.8(s, 3H), 2.9(m, 1H), 3.3(m, 1H), 3.9 (m, 1H), 3.95(s, 6H), 5.8(s, 1H), 6.0(s, 1H) 6.4(m, 1H), 7.8(s, 1H) |
| 5a | Me | Me | 2,4,6-trimethylpyrimidin-5-yl | bond | $^1$H NMR(CDCl$_3$); δ2.15(m, 2H), 2.4(s, 3H), 2.45(m, 2H), 2.45 (s, 6H), 2.65(m, 2H), 2.75(m, 1H), 2.8(s, 3H), 2.9(m, 1H), 3.3 (m, 1H), 3.9(m, 1H), 6.0(s, 1H), 6.4(m, 1H), 6.8(s, 1H), 7.8(s, 1H) |
| 6a | Me | Me | 5-chloro-3-trifluoromethyl-2-methylpyridin-4-yl | bond | $^1$H NMR(CDCl$_3$): δ2.15(m, 2H), 2.4(s, 3H), 2.45(m, 2H), 2.65 (m, 2H), 2.8(s, 3H), 2.8(m, 2H), 3.25(m, 1H), 3.95(m, 1H), 6.0 (s, 1H), 6.6(m, 1H), 7.8(s, 1H), 7.9 (m, 1H), 8.4(m, 1H) |
| 7a | Me | Me | 5-nitro-2-methylpyridin-? | bond | $^1$N NMR(CDCl$_3$): δ2.15(m, 2H), 2.4(s, 3H), 2.45(m, 2H), 2.65 (m, 2H), 2.8(s, 3H), 2.85(m, 2H), 3.25(m, 1H), 3.8(m, 1H), 6.0 (s, 1H), 6.65(m, 1H), 6.85(d, 1H), 7.8(s, 1H), 8.45(m, 1H), 9.15 (m, 1H) |
| 8a | Me | Me | 3,6-bis(trifluoromethyl)-2-methylpyridin-? | bond | $^1$H NMR(CDCl$_3$): δ2.15(m, 2H), 2.4(s, 3H), 2.45(m, 2H), 2.65 (m, 2H), 2.85(s, 3H), 2.9(m, 2H), 3.25(m, 1H), 3.75(m, 1H), 6.0 (s, 1H), 6.75(m, 1H), 7.5(d, 2H), 7.8(s, 1H), 8.15(d, 1H) |
| 9a | Me | Me | 3-chloro-2-methylpyridin-? | bond | $^1$H NMR(CDCl$_3$): δ2.15(m, 2H), 2.4(s, 3H), 2.45(m, 2H), 2.65 (m, 2H), 2.8(m, 2H), 2.85(s, 3H), 3.25(m, 1H), 3.85(m, 1H), 6.0 (s, 1H), 6.6(m, 1H), 7.0(m, 1H), 7.7(m, 2H), 7.8(s, 1H), 8.15 (m, 1H) |
| 10a | Me | Me | 5-cyano-2-methylpyridin-? | bond | $^1$H NMR(CDCl$_3$): δ2.15(m, 2H), 2.4(s, 3H), 2.45(m, 2H), 2.65 (m, 2H), 2.8(m, 1H), 2.85(s, 3H), 2.95(m, 1H), 3.25(m, 1H), 3.8 (m, 1H), 6.0(s, 1H), 6.7(m, 1H), 6.85(d, 1H), 7.8(s, 1H), 8.15 (m, 1H), 8.95(m, 1H) |

TABLE 1a-continued

Precursors of the compounds in Table 1

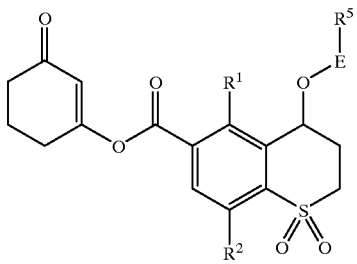

| No. | R¹ | R² | R⁵ | E | Physical data |
|---|---|---|---|---|---|
| 11a | Me | Me | 2-methylpyrazinyl | bond | ¹H NMR(CDCl₃): δ2.15(m, 2H), 2.4(s, 3H), 2.45(m, 2H), 2.65 (m, 2H), 2.8(m, 1H), 2.85(s, 3H), 2.95(m, 1H), 3.25(m, 1H), 3.8 (m, 1H), 6.0(s, 1H), 6.55(m, 1H), 7.8(s, 1H), 8.2(m, 1H), 8.25 (m, 1H) |
| 12a | Me | Me | phenyl | CH₂ | ¹H NMR(CDCl₃): δ2.15(m, 2H), 2.45(m, 2H), 2.55(s, 3H), 2.65 (m, 2H), 2.8(m, 1H), 2.75(s, 3H), 2.8(m, 1H), 3.2(m, 1H), 3.85 (m, 1H), 4.55(d, 2H), 4.7(d, 2H), 4.8(s, br, 1H), 6.0(s, 1H), 7.3 (m, 5H), 7.75(s, 1H) |
| 13a | Me | Me | 3-fluoro-2-methylpyridinyl | CH₂ | ¹H NMR(CDCl₃): δ2.15(m, 2H), 2.45(m, 2H), 2.55(s, 3H), 2.65 (m, 2H), 2.8(m, 1H), 2.75(s, 3H), 2.8(m, 1H), 3.2(m, 1H), 3.85 (m, 1H), 4.65(m, 1H), 4.85(m, 1H), 4.8(s, 1H), 6.0(s, 1H), 7.3 (m, 1H), 7.4(m, 1H), 7.8(s, 1H), 8.4(m, 1H) |

TABLE 1b

Precursors of the compounds in Table 1a

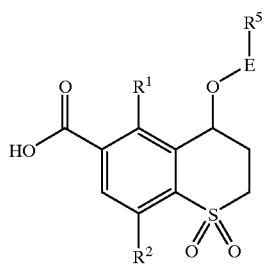

| No. | R¹ | R² | R⁵ | E | Physical data |
|---|---|---|---|---|---|
| 2b | Me | Me | 2-methylpyrimidinyl | bond | ¹H NMR(CDCl₃): δ2.4(s, 3H), 2.8(s, 3H), 2.85(m, 2H), 3.25 (m, 1H), 3.9(m, 1H), 6.5(m, 1H), 7.05 (t, 1H), 7.8(s, 1H), 8.6(d, 2H) |

TABLE 1b-continued

Precursors of the compounds in Table 1a

| No. | $R^1$ | $R^2$ | $R^5$ | E | Physical data |
|---|---|---|---|---|---|
| 4b | Me | Me | 4,6-dimethoxy-2-pyrimidinyl (OMe, OMe) | bond | $^1$H NMR(CDCl$_3$): δ2.4(s, 3H), 2.75(s, 3H), 2.75(m, 1H), 2.95 (m, 1H), 3.25(m, 1H), 3.9(m, 1H), 3.95(s, 6H), 5.8(s, 1H), 6.4(m, 1H), 7.7(s, 1H) |
| 5b | Me | Me | 2,4,6-trimethylpyrimidinyl | bond | $^1$H NMR(CDCl$_3$): δ2.35(s, 3H), 2.4(s, 6H), 2.8(s, 3H), 2.85(m, 2H), 3.25(m, 1H), 3.95(m, 1H), 6.45 (m, 1H), 6.8(s, 1H), 7.65(s, 1H) |
| 6b | Me | Me | 5-chloro-3-trifluoromethyl-2-methylpyridinyl (F$_3$C, Cl) | bond | $^1$H NMR(CDCl$_3$): δ2.35(s, 3H), 2.8(s, 3H), 2.85(m, 2H), 3.25 (m, 1H), 3.75(m, 1H), 3.9(s, 3H), 6.6 (s, 1H), 7.7(s, 1H), 7.9(m, 1H), 8.35 (m, 1H) |
| 7b | Me | Me | 5-nitro-2-methylpyridinyl (NO$_2$) | bond | $^1$H NMR(Me$_2$SO-d6): δ2.25(s, 3H), 2.7(s, 3H), 2.75(m, 2H), 3.55 (m, 1H), 3.7(m, 1H), 6.65(s, 1H), 7.15(d, 1H), 7.7(s, 1H), 8.55(m, 1H), 9.15(m, 1H) |
| 8b | Me | Me | 3,6-bis(trifluoromethyl)-2-methylpyridinyl (F$_3$C, CF$_3$) | bond | $^1$H NMR(CDCl$_3$): δ2.35(s, 3H), 2.8(s, 3H), 2.85(m, 2H), 3.25 (m, 1H), 3.75(m, 1H), 6.7(m, 1H), 7.5 (d, 2H), 7.75(s, 1H), 8.15(d, 1H) |
| 9b | Me | Me | 3-chloro-2-methylpyridinyl (Cl) | bond | $^1$H NMR(CDCl$_3$): δ2.4(s, 3H), 2.8(s, 3H), 2.8(m, 2H), 3.25(m, 1H), 3.9(m, 1H), 6.6(m, 1H), 6.95(m, 1H), 7.7(m, 1H), 7.85(s, 1H), 8.15(m, 1H) |
| 10b | Me | Me | 5-cyano-2-methylpyridinyl (CN) | bond | $^1$H NMR(CDCl$_3$): δ2.35(s, 3H), 2.75(m, 1H), 2.8(s, 3H), 2.9(m, 1H), 3.25(m, 1H), 3.8(m, 1H), 6.6(m, 1H), 6.75(d, 1H), 7.75(s, 1H), 8.1(m, 1H), 8.9(m, 1H) |
| 11b | Me | Me | 6-methylpyrazinyl | bond | $^1$H NMR(CDCl$_3$): δ2.35(s, 3H), 2.8(s, 3H), 2.8(m, 2H), 3.25(m, 1H), 3.8(m, 1H), 6.5(m, 1H), 7.75(s, 1H), 8.2(m, 1H), 8.25(m, 1H) |

TABLE 1b-continued

Precursors of the compounds in Table 1a

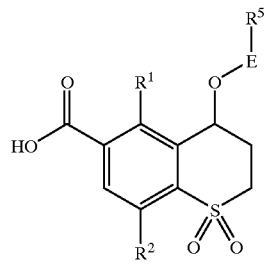

| No. | R¹ | R² | R⁵ | E | Physical data |
|---|---|---|---|---|---|
| 12b | Me | Me | (3-methylphenyl) | $CH_2$ | ¹H NMR(CDCl₃): δ2.45(s, 3H), 2.6(m, 1H), 2.75(s, 3H), 2.75 (m, 1H), 3.25(m, 1H), 3.9(m, 1H), 4.55(d, 2H), 4.7(d, 2H), 4.8 (s, br, 1H), 7.35(m, 5H), 7.75(s, 1H) |
| 13b | Me | Me | (3-fluoro-2-methylpyridyl) | $CH_2$ | ¹H NMR(CDCl₃): δ2.45(s, 3H), 2.6 (m, 1H), 2.75(s, 3H), 2.95(m, 1H), 3.25(m, 1H), 3.9(m, 1H), 4.75 (d, 2H), 4.85(d, 2H), 4.85(s, br, 1H), 7.3(m, 1H), 7.4(m, 1H), 7.6(s, 1H), 8.4(m, 1H) |

TABLE 1c

Precursors of the compounds in Table 1b

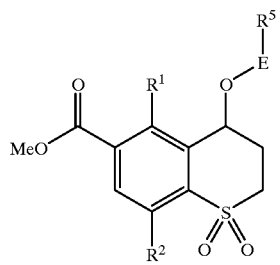

| No. | R¹ | R² | R⁵ | E | Physical data |
|---|---|---|---|---|---|
| 2c | Me | Me | (2-methylpyrimidyl) | bond | ¹H NMR(CDCl₃): δ2.35 (s, 3H) 2.8(s 3H), 2.85 (m, 2H), 3.25(m, 1H), 3.9 (m, 1H), 3.9(s, 3H), 6.5 (m, 1H), 7,05(t, 1H), 7.8 (s, 1H), 8.6(d, 2H) |
| 4c | Me | Me | (4,6-dimethoxy-2-methylpyrimidyl) | bond | ¹H NMR(CDCl₃): δ2.35 (s, 3H), 2.8(s, 3H), 2.85 (m, 2H), 3.25(m, 1H), 3.9 (m, 1H), 3.9(s, 3H), 3.95 (s, 6H), 5.8(s, 1H), 6.4(m, 1H), 7.7(s, 1H) |
| 5c | Me | Me | (2,4,6-trimethylpyrimidyl) | bond | ¹H NMR(CDCl₃): δ2.35 (s, 3H), 2.4(s, 6H), 2.8(s, 3H), 2.85(m, 2H), 3.25(m, 1H), 3.9 (s, 3H), 3.95(m, 1H), 6.45 (m, 1H), 6.8(s, 1H), 7.65 (s, 1H) |

TABLE 1c-continued

Precursors of the compounds in Table 1b

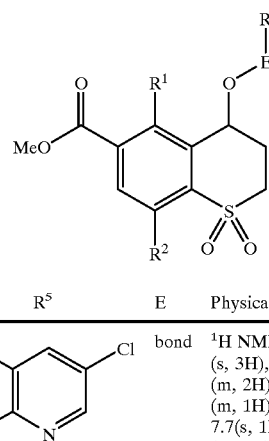

| No. | R¹ | R² | R⁵ | E | Physical data |
|---|---|---|---|---|---|
| 6c | Me | Me | 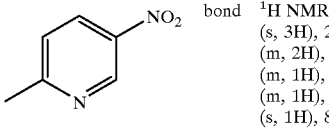 | bond | ¹H NMR(CDCl₃): δ2.35 (s, 3H), 2.8(s, 3H), 2.85 (m, 2H), 3.25(m, 1H), 3.75 (m, 1H), 3.9(s, 3H), 6.6(s, 1H), 7.7(s, 1H), 7.9(m, 1H), 8.35 (m, 1H) |
| 7c | Me | Me | 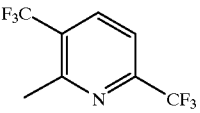 | bond | ¹H NMR(CDCl₃): δ2.35 (s, 3H), 2.8(s, 3H), 2.85 (m, 2H), 3.25(m, 1H), 3.75 (m, 1H), 3.9(s, 3H), 6.65 (m, 1H), 6.85(d, 1H), 7.7 (s, 1H), 8.45(m, 1H), 9.15 (m, 1H) |
| 8c | Me | Me | 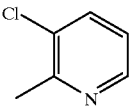 | bond | ¹H NMR(CDCl₃): δ2.35 (s, 3H), 2.8(s, 3H), 2.85 (m, 2H), 3.25(m, 1H), 3.75 (m, 1H), 3.9(s, 3H), 6.7 (m, 1H), 7.5(d, 2H), 7.75 (s, 1H), 8.15(d, 1H) |
| 9c | Me | Me | 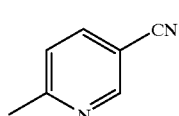 | bond | ¹H NMR(CDCl₃): δ2.4 (s, 3H), 2.8(s, 3H), 2.8(m, 2H), 3.25(m, 1H), 3.9(m, 1H), 3.9 (s, 3H), 6.6(m, 1H), 6.95 (m, 1H), 7.7(s, 1H), 7.7 (m, 1H), 8.1(m, 2H) |
| 10c | Me | Me | 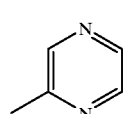 | bond | ¹H NMR(CDCl₃): δ2.3 (s, 3H), 2.8(s, 3H), 2.8(m, 2H), 3.25(m, 1H), 3.75(m, 1H), 3.9 (s, 3H), 6.6(m, 1H), 6.8(d, 1H), 7.7(s, 1H), 8.15(m, 1H), 8.55 (m, 1H) |
| 11c | Me | Me | 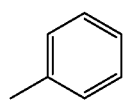 | bond | ¹H NMR(CDCl₃): δ2.35 (s, 3H), 2.8(s, 3H), 2.8(m, 2H), 3.25(m, 1H), 3.8(m, 1H), 3.9 (s, 3H), 6.5(m, 1H), 7.7(s, 1H), 8.15(m, 1H), 8.25(m, 1H) |
| 12c | Me | Me | 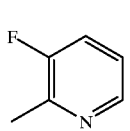 | CH₂ | ¹H NMR(CDCl₃): δ2.45 (s, 3H), 2.6(m, 1H), 2.75 (s, 3H), 2.75(m, 1H), 3.25 (m, 1H), 3.9(m, 1H), 3.9 (s, 3H), 4.55(d, 2H), 4.7 (d, 2H), 4.8(s, br, 1H), 7.35 (m, 5H), 7.6(s, 1H) |
| 13c | Me | Me |  | CH₂ | ¹H NMR(CDCl₃): δ2.45 (s, 3H), 2.6(m, 1H), 2.75 (s, 3H), 2.95(m, 1H), 3.25 (m, 1H), 3.85(s, 3H), 3.9 (m, 1H), 4.75(d, 2H), 4.85 (d, 2H), 4.85(s, br, 1H), 7.3 (m, 1H), 7.4(m, 1H), 7.6 (s, 1H), 8.4(m, 1H) |

TABLE 2

Compounds of the formula (I) according to the invention in which the substituents and indices are as defined below:

A = SO$_2$    B = CH$_2$—CH$_2$    E = bond
R$^1$ = CH$_3$    R$^2$ = CH$_3$    R$^3$ = H
R$^4$ = H    R$^5$ = (3-R$^D$, 5-R$^E$, 2-methylpyridinyl)    R$^6$ = OH
R$^7$ = R$^A$, R$^B$    (X)$_h$ = O    Y = CH$_2$
Z = CH$_2$    v = 1    Q = formula (II)

| No. | R$^A$ | R$^B$ | R$^C$ | R$^D$ | R$^E$ |
|---|---|---|---|---|---|
| 14 | H | H | Bz | H | H |
| 15 | H | Me | Bz | H | H |
| 16 | Me | Me | Bz | H | H |
| 17 | H | H | PhC(O)CH$_2$ | H | H |
| 18 | H | Me | PhC(O)CH$_2$ | H | H |
| 19 | Me | Me | PhC(O)CH$_2$ | H | H |
| 20 | H | H | 4-Me—PhC(O) | H | H |
| 21 | H | Me | 4-Me—PhC(O) | H | H |
| 22 | Me | Me | 4-Me—PhC(O) | H | H |
| 23 | H | H | MeSO$_2$ | H | H |
| 24 | H | Me | MeSO$_2$ | H | H |
| 25 | Me | Me | MeSO$_2$ | H | H |
| 26 | H | H | EtSO$_2$ | H | H |
| 27 | H | Me | EtSO$_2$ | H | H |
| 28 | Me | Me | EtSO$_2$ | H | H |
| 29 | H | H | PrSO$_2$ | H | H |
| 30 | H | Me | PrSO$_2$ | H | H |
| 31 | Me | Me | PrSO$_2$ | H | H |
| 32 | H | H | PhSO$_2$ | H | H |
| 33 | H | Me | PhSO$_2$ | H | H |
| 34 | Me | Me | PhSO$_2$ | H | H |
| 35 | H | H | 4-Me—PhSO$_2$ | H | H |
| 36 | H | Me | 4-Me—PhSO$_2$ | H | H |
| 37 | Me | Me | 4-Me—PhSO$_2$ | H | H |
| 38 | H | H | Bz | H | NO$_2$ |
| 39 | H | Me | Bz | H | NO$_2$ |
| 40 | Me | Me | Bz | H | NO$_2$ |
| 41 | H | H | PhC(O)CH$_2$ | H | NO$_2$ |
| 42 | H | Me | PhC(O)CH$_2$ | H | NO$_2$ |
| 43 | Me | Me | PhC(O)CH$_2$ | H | NO$_2$ |
| 44 | H | H | 4-Me—PhC(O) | H | NO$_2$ |
| 45 | H | Me | 4-Me—PhC(O) | H | NO$_2$ |
| 46 | Me | Me | 4-Me—PhC(O) | H | NO$_2$ |
| 47 | H | H | MeSO$_2$ | H | NO$_2$ |
| 48 | H | Me | MeSO$_2$ | H | NO$_2$ |
| 49 | Me | Me | MeSO$_2$ | H | NO$_2$ |
| 50 | H | H | EtSO$_2$ | H | NO$_2$ |
| 51 | H | Me | EtSO$_2$ | H | NO$_2$ |
| 52 | Me | Me | EtSO$_2$ | H | NO$_2$ |
| 53 | H | H | PrSO$_2$ | H | NO$_2$ |
| 54 | H | Me | PrSO$_2$ | H | NO$_2$ |
| 55 | Me | Me | PrSO$_2$ | H | NO$_2$ |
| 56 | H | H | PhSO$_2$ | H | NO$_2$ |
| 57 | H | Me | PhSO$_2$ | H | NO$_2$ |
| 58 | Me | Me | PhSO$_2$ | H | NO$_2$ |
| 59 | H | H | 4-Me—PhSO$_2$ | H | NO$_2$ |
| 60 | H | Me | 4-Me—PhSO$_2$ | H | NO$_2$ |
| 61 | Me | Me | 4-Me—PhSO$_2$ | H | NO$_2$ |
| 62 | H | H | Bz | H | CN |
| 63 | H | Me | Bz | H | CN |
| 64 | Me | Me | Bz | H | CN |
| 65 | H | H | PhC(O)CH$_2$ | H | CN |
| 66 | H | Me | PhC(O)CH$_2$ | H | CN |
| 67 | Me | Me | PhC(O)CH$_2$ | H | CN |
| 68 | H | H | 4-Me—PhC(O) | H | CN |
| 69 | H | Me | 4-Me—PhC(O) | H | CN |
| 70 | Me | Me | 4-Me—PhC(O) | H | CN |
| 71 | H | H | MeSO$_2$ | H | CN |
| 72 | H | Me | MeSO$_2$ | H | CN |
| 73 | Me | Me | MeSO$_2$ | H | CN |
| 74 | H | H | EtSO$_2$ | H | CN |
| 75 | H | Me | EtSO$_2$ | H | CN |
| 76 | Me | Me | EtSO$_2$ | H | CN |
| 77 | H | H | PrSO$_2$ | H | CN |
| 78 | H | Me | PrSO$_2$ | H | CN |
| 79 | Me | Me | PrSO$_2$ | H | CN |
| 80 | H | H | PhSO$_2$ | H | CN |
| 81 | H | Me | PhSO$_2$ | H | CN |
| 82 | Me | Me | PhSO$_2$ | H | CN |
| 83 | H | H | 4-Me—PhSO$_2$ | H | CN |
| 84 | H | Me | 4-Me—PhSO$_2$ | H | CN |
| 85 | Me | Me | 4-Me—PhSO$_2$ | H | CN |
| 86 | H | H | Bz | Cl | H |
| 87 | H | Me | Bz | Cl | H |
| 88 | Me | Me | Bz | Cl | H |
| 89 | H | H | PhC(O)CH$_2$ | Cl | H |
| 90 | H | Me | PhC(O)CH$_2$ | Cl | H |
| 91 | Me | Me | PhC(O)CH$_2$ | Cl | H |
| 92 | H | H | 4-Me—PhC(O) | Cl | H |
| 93 | H | Me | 4-Me—PhC(O) | Cl | H |
| 94 | Me | Me | 4-Me—PhC(O) | Cl | H |
| 95 | H | H | MeSO$_2$ | Cl | H |
| 96 | H | Me | MeSO$_2$ | Cl | H |
| 97 | Me | Me | MeSO$_2$ | Cl | H |
| 98 | H | H | EtSO$_2$ | Cl | H |
| 99 | H | Me | EtSO$_2$ | Cl | H |
| 100 | Me | Me | EtSO$_2$ | Cl | H |
| 101 | H | H | PrSO$_2$ | Cl | H |
| 102 | H | Me | PrSO$_2$ | Cl | H |
| 103 | Me | Me | PrSO$_2$ | Cl | H |
| 104 | H | H | PhSO$_2$ | Cl | H |
| 105 | H | Me | PhSO$_2$ | Cl | H |
| 106 | Me | Me | PhSO$_2$ | Cl | H |
| 107 | H | H | 4-Me—PhSO$_2$ | Cl | H |
| 108 | H | Me | 4-Me—PhSO$_2$ | Cl | H |
| 109 | Me | Me | 4-Me—PhSO$_2$ | Cl | H |
| 110 | H | H | Bz | Cl | CF$_3$ |
| 111 | H | Me | Bz | Cl | CF$_3$ |
| 112 | Me | Me | Bz | Cl | CF$_3$ |
| 113 | H | H | PhC(O)CH$_2$ | Cl | CF$_3$ |
| 114 | H | Me | PhC(O)CH$_2$ | Cl | CF$_3$ |
| 115 | Me | Me | PhC(O)CH$_2$ | Cl | CF$_3$ |
| 116 | H | H | 4-Me—PhC(O) | Cl | CF$_3$ |
| 117 | H | Me | 4-Me—PhC(O) | Cl | CF$_3$ |
| 118 | Me | Me | 4-Me—PhC(O) | Cl | CF$_3$ |
| 119 | H | H | MeSO$_2$ | Cl | CF$_3$ |
| 120 | H | Me | MeSO$_2$ | Cl | CF$_3$ |
| 121 | Me | Me | MeSO$_2$ | Cl | CF$_3$ |
| 122 | H | H | EtSO$_2$ | Cl | CF$_3$ |
| 123 | H | Me | EtSO$_2$ | Cl | CF$_3$ |
| 124 | Me | Me | EtSO$_2$ | Cl | CF$_3$ |
| 125 | H | H | PrSO$_2$ | Cl | CF$_3$ |
| 126 | H | Me | PrSO$_2$ | Cl | CF$_3$ |
| 127 | Me | Me | PrSO$_2$ | Cl | CF$_3$ |
| 128 | H | H | PhSO$_2$ | Cl | CF$_3$ |
| 129 | H | Me | PhSO$_2$ | Cl | CF$_3$ |
| 130 | Me | Me | PhSO$_2$ | Cl | CF$_3$ |
| 131 | H | H | 4-Me—PhSO$_2$ | Cl | CF$_3$ |
| 132 | H | Me | 4-Me—PhSO$_2$ | Cl | CF$_3$ |
| 133 | Me | Me | 4-Me—PhSO$_2$ | Cl | CF$_3$ |
| 134 | H | H | Bz | H | CF$_3$ |

TABLE 2-continued

Compounds of the formula (I) according to the invention in which the substituents and indices are as defined below:

| | | | | | |
|---|---|---|---|---|---|
| 135 | H | Me | Bz | H | CF$_3$ |
| 136 | Me | Me | Bz | H | CF$_3$ |
| 137 | H | H | PhC(O)CH$_2$ | H | CF$_3$ |
| 138 | H | Me | PhC(O)CH$_2$ | H | CF$_3$ |
| 139 | Me | Me | PhC(O)CH$_2$ | H | CF$_3$ |
| 140 | H | H | 4-Me—PhC(O) | H | CF$_3$ |
| 141 | H | Me | 4-Me—PhC(O) | H | CF$_3$ |
| 142 | Me | Me | 4-Me—PhC(O) | H | CF$_3$ |
| 143 | H | H | MeSO$_2$ | H | CF$_3$ |
| 144 | H | Me | MeSO$_2$ | H | CF$_3$ |
| 145 | Me | Me | MeSO$_2$ | H | CF$_3$ |
| 146 | H | H | EtSO$_2$ | H | CF$_3$ |
| 147 | H | Me | EtSO$_2$ | H | CF$_3$ |
| 148 | Me | Me | EtSO$_2$ | H | CF$_3$ |
| 149 | H | H | PrSO$_2$ | H | CF$_3$ |
| 150 | H | Me | PrSO$_2$ | H | CF$_3$ |
| 151 | Me | Me | PrSO$_2$ | H | CF$_3$ |
| 152 | H | H | PhSO$_2$ | H | CF$_3$ |
| 153 | H | Me | PhSO$_2$ | H | CF$_3$ |
| 154 | Me | Me | PhSO$_2$ | H | CF$_3$ |
| 155 | H | H | 4-Me—PhSO$_2$ | H | CF$_3$ |
| 156 | H | Me | 4-Me—PhSO$_2$ | H | CF$_3$ |
| 157 | Me | Me | 4-Me—PhSO$_2$ | H | CF$_3$ |

TABLE 3

Compounds of the formula (I) according to the invention in which the substituents and indices are as defined below:

| | | | | | |
|---|---|---|---|---|---|
| A = | SO$_2$ | B = | CH$_2$—CH$_2$ | R$^1$ = | CH$_3$ |
| R$^2$ = | CH$_3$ | R$^3$ = | H | R$^4$ = | H |
| R$^5$ = | (pyridyl) | (X)$_l$ = | O | E = | bond |

Q = formula (III) where G$^1$–G$^2$ is NR$^{10}$COR$^{11}$

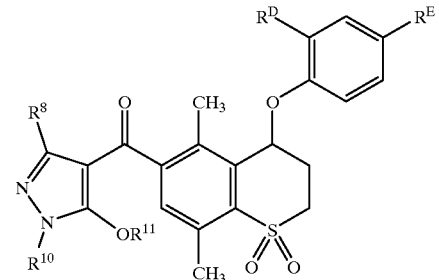

| No. | R$^8$ | R$^{10}$ | R$^{11}$ | R$^D$ | R$^E$ |
|---|---|---|---|---|---|
| 158 | H | Et | Bz | H | H |
| 159 | Me | Me | Bz | H | H |
| 160 | H | Et | 4-Me—PhC(O) | H | H |
| 161 | Me | Me | 4-Me—PhC(O) | H | H |
| 162 | H | Et | MeSO$_2$ | H | H |
| 163 | Me | Me | MeSO$_2$ | H | H |
| 164 | H | Et | EtSO$_2$ | H | H |
| 165 | Me | Me | EtSO$_2$ | H | H |
| 166 | H | Et | PrSO$_2$ | H | H |
| 167 | Me | Me | PrSO$_2$ | H | H |
| 168 | H | Et | PhSO$_2$ | H | H |
| 169 | Me | Me | PhSO$_2$ | H | H |
| 170 | H | Et | 4-Me—PhSO$_2$ | H | H |
| 171 | Me | Me | 4-Me—PhSO$_2$ | H | H |
| 172 | H | Et | Bz | H | NO$_2$ |
| 173 | Me | Me | Bz | H | NO$_2$ |
| 174 | H | Et | 4-Me—PhC(O) | H | NO$_2$ |
| 175 | Me | Me | 4-Me—PhC(O) | H | NO$_2$ |
| 176 | H | Et | MeSO$_2$ | H | NO$_2$ |
| 177 | Me | Me | MeSO$_2$ | H | NO$_2$ |
| 178 | H | Et | EtSO$_2$ | H | NO$_2$ |
| 179 | Me | Me | EtSO$_2$ | H | NO$_2$ |
| 180 | H | Et | PrSO$_2$ | H | NO$_2$ |
| 181 | Me | Me | PrSO$_2$ | H | NO$_2$ |
| 182 | H | Et | PhSO$_2$ | H | NO$_2$ |
| 183 | Me | Me | PhSO$_2$ | H | NO$_2$ |
| 184 | H | Et | 4-Me—PhSO$_2$ | H | NO$_2$ |
| 185 | Me | Me | 4-Me—PhSO$_2$ | H | NO$_2$ |
| 186 | H | Et | Bz | H | CN |
| 187 | Me | Me | Bz | H | CN |
| 188 | H | Et | 4-Me—PhC(O) | H | CN |
| 189 | Me | Me | 4-Me—PhC(O) | H | CN |
| 190 | H | Et | MeSO$_2$ | H | CN |
| 191 | Me | Me | MeSO$_2$ | H | CN |
| 192 | H | Et | EtSO$_2$ | H | CN |
| 193 | Me | Me | EtSO$_2$ | H | CN |
| 194 | H | Et | PrSO$_2$ | H | CN |
| 195 | Me | Me | PrSO$_2$ | H | CN |
| 196 | H | Et | PhSO$_2$ | H | CN |
| 197 | Me | Me | PhSO$_2$ | H | CN |
| 198 | H | Et | 4-Me—PhSO$_2$ | H | CN |
| 199 | Me | Me | 4-Me—PhSO$_2$ | H | CN |
| 200 | H | Et | Bz | Cl | H |
| 201 | Me | Me | Bz | Cl | H |
| 202 | H | Et | 4-Me—PhC(O) | Cl | H |
| 203 | Me | Me | 4-Me—PhC(O) | Cl | H |
| 204 | H | Et | MeSO$_2$ | Cl | H |
| 205 | Me | Me | MeSO$_2$ | Cl | H |
| 206 | H | Et | EtSO$_2$ | Cl | H |
| 207 | Me | Me | EtSO$_2$ | Cl | H |
| 208 | H | Et | PrSO$_2$ | Cl | H |
| 209 | Me | Me | PrSO$_2$ | Cl | H |
| 210 | H | Et | PhSO$_2$ | Cl | H |
| 211 | Me | Me | PhSO$_2$ | Cl | H |
| 212 | H | Et | 4-Me—PhSO$_2$ | Cl | H |
| 213 | Me | Me | 4-Me—PhSO$_2$ | Cl | H |
| 214 | H | Et | Bz | Cl | CF$_3$ |
| 215 | Me | Me | Bz | Cl | CF$_3$ |
| 216 | H | Et | 4-Me—PhC(O) | Cl | CF$_3$ |
| 217 | Me | Me | 4-Me—PhC(O) | Cl | CF$_3$ |
| 218 | H | Et | MeSO$_2$ | Cl | CF$_3$ |
| 219 | Me | Me | MeSO$_2$ | Cl | CF$_3$ |
| 220 | H | Et | EtSO$_2$ | Cl | CF$_3$ |
| 221 | Me | Me | EtSO$_2$ | Cl | CF$_3$ |
| 222 | H | Et | PrSO$_2$ | Cl | CF$_3$ |
| 223 | Me | Me | PrSO$_2$ | Cl | CF$_3$ |
| 224 | H | Et | PhSO$_2$ | Cl | CF$_3$ |
| 225 | Me | Me | PhSO$_2$ | Cl | CF$_3$ |
| 226 | H | Et | 4-Me—PhSO$_2$ | Cl | CF$_3$ |
| 227 | Me | Me | 4-Me—PhSO$_2$ | Cl | CF$_3$ |
| 228 | H | Et | Bz | H | CF$_3$ |
| 229 | Me | Me | Bz | H | CF$_3$ |
| 230 | H | Et | 4-Me—PhC(O) | H | CF$_3$ |
| 231 | Me | Me | 4-Me—PhC(O) | H | CF$_3$ |
| 232 | H | Et | MeSO$_2$ | H | CF$_3$ |
| 233 | Me | Me | MeSO$_2$ | H | CF$_3$ |
| 234 | H | Et | EtSO$_2$ | H | CF$_3$ |
| 235 | Me | Me | EtSO$_2$ | H | CF$_3$ |
| 236 | H | Et | PrSO$_2$ | H | CF$_3$ |
| 237 | Me | Me | PrSO$_2$ | H | CF$_3$ |
| 238 | H | Et | PhSO$_2$ | H | CF$_3$ |
| 239 | Me | Me | PhSO$_2$ | H | CF$_3$ |
| 240 | H | Et | 4-Me—PhSO$_2$ | H | CF$_3$ |
| 241 | Me | Me | 4-Me—PhSO$_2$ | H | CF$_3$ |

TABLE 4

Compounds of the formula (I) according to the invention in which the substituents are as defined below:

A = SO$_2$   B = CH$_2$—CH$_2$   R$^3$ = H
R$^4$ = H    R$^5$ = 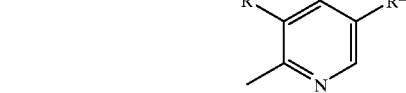   (X)$_1$ = O
E = bond    Q = formula (III) where G$^1$–G$^2$ is OCR$^9$
R$^9$ = c-Pr

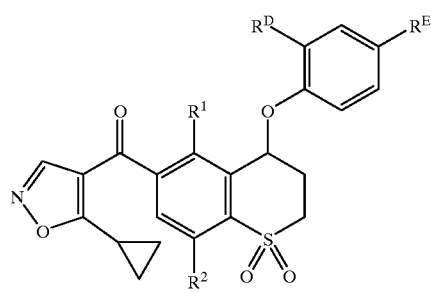

| No. | R$^1$ | R$^2$ | R$^D$ | R$^E$ |
|---|---|---|---|---|
| 242 | H | H | H | H |
| 243 | Me | H | H | H |
| 244 | Me | Me | H | H |
| 245 | Cl | H | H | H |
| 246 | Cl | Me | H | H |
| 247 | Cl | Cl | H | H |
| 248 | Me | Cl | H | H |
| 249 | H | H | H | NO$_2$ |
| 250 | Me | H | H | NO$_2$ |
| 251 | Me | Me | H | NO$_2$ |
| 252 | Cl | H | H | NO$_2$ |
| 253 | Cl | Me | H | NO$_2$ |
| 254 | Cl | Cl | H | NO$_2$ |
| 255 | Me | Cl | H | NO$_2$ |
| 256 | H | H | H | CN |
| 257 | Me | H | H | CN |
| 258 | Me | Me | H | CN |
| 259 | Cl | H | H | CN |
| 260 | Cl | Me | H | CN |
| 261 | Cl | Cl | H | CN |
| 262 | Me | Cl | H | CN |
| 263 | H | H | Cl | H |
| 264 | Me | H | Cl | H |
| 265 | Me | Me | Cl | H |
| 266 | Cl | H | Cl | H |
| 267 | Cl | Me | Cl | H |
| 268 | Cl | Cl | Cl | H |
| 269 | Me | Cl | Cl | H |
| 270 | H | H | Cl | CF$_3$ |
| 271 | Me | H | Cl | CF$_3$ |
| 272 | Me | Me | Cl | CF$_3$ |
| 273 | Cl | H | Cl | CF$_3$ |
| 274 | Cl | Me | Cl | CF$_3$ |
| 275 | Cl | Cl | Cl | CF$_3$ |
| 276 | Me | Cl | Cl | CF$_3$ |
| 277 | H | H | H | CF$_3$ |
| 278 | Me | H | H | CF$_3$ |
| 279 | Me | Me | H | CF$_3$ |
| 280 | Cl | H | H | CF$_3$ |
| 281 | Cl | Me | H | CF$_3$ |
| 282 | Cl | Cl | H | CF$_3$ |
| 283 | Me | Cl | H | CF$_3$ |

TABLE 5

Compounds of the formula (I) according to the invention in which the substituents are as defined below:

A = SO$_2$   B = CH$_2$—CH$_2$   R$^3$ = H
R$^5$ = 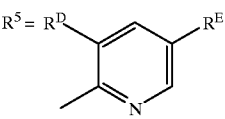
R$^4$ = H    Q = formula (III) where G$^1$–G$^2$ is SCR$^2$   (X)$_1$ = O
E = bond
R$^9$ = c-Pr

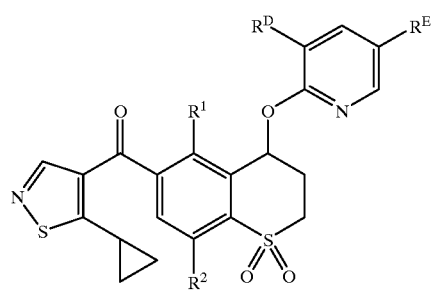

| No. | R$^1$ | R$^2$ | R$^D$ | R$^E$ |
|---|---|---|---|---|
| 284 | H | H | H | H |
| 285 | Me | H | H | H |
| 286 | Me | Me | H | H |
| 287 | Cl | H | H | H |
| 288 | Cl | Me | H | H |
| 289 | Cl | Cl | H | H |
| 290 | Me | Cl | H | H |
| 291 | H | H | H | NO$_2$ |
| 292 | Me | H | H | NO$_2$ |
| 293 | Me | Me | H | NO$_2$ |
| 294 | Cl | H | H | NO$_2$ |
| 295 | Cl | Me | H | NO$_2$ |
| 296 | Cl | Cl | H | NO$_2$ |
| 297 | Me | Cl | H | NO$_2$ |
| 298 | H | H | H | CN |
| 299 | Me | H | H | CN |
| 300 | Me | Me | H | CN |
| 301 | Cl | H | H | CN |
| 302 | Cl | Me | H | CN |
| 303 | Cl | Cl | H | CN |
| 304 | Me | Cl | H | CN |
| 305 | H | H | Cl | H |
| 306 | Me | H | Cl | H |
| 307 | Me | Me | Cl | H |
| 308 | Cl | H | Cl | H |
| 309 | Cl | Me | Cl | H |
| 310 | Cl | Cl | Cl | H |
| 311 | Me | Cl | Cl | H |
| 312 | H | H | Cl | CF$_3$ |
| 313 | Me | H | Cl | CF$_3$ |
| 314 | Me | Me | Cl | CF$_3$ |
| 315 | Cl | H | Cl | CF$_3$ |
| 316 | Cl | Me | Cl | CF$_3$ |
| 317 | Cl | Cl | Cl | CF$_3$ |
| 318 | Me | Cl | Cl | CF$_3$ |
| 319 | H | H | H | CF$_3$ |
| 320 | Me | H | H | CF$_3$ |
| 321 | Me | Me | H | CF$_3$ |
| 322 | Cl | H | H | CF$_3$ |
| 323 | Cl | Me | H | CF$_3$ |
| 324 | Cl | Cl | H | CF$_3$ |
| 325 | Me | Cl | H | CF$_3$ |

TABLE 6

Compounds of the formula (I) according to the invention in which the substituents are as defined below:

A = SO$_2$     B = CH$_2$—CH$_2$     R$^3$ = H
R$^5$ = 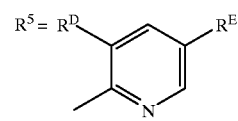
R$^4$ = H     (X)$_1$ = O
E = bond     Q = formula (IV)     R$^9$ = c-Pr

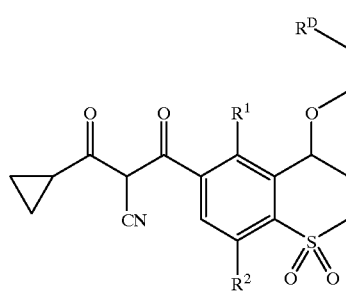

| No. | R$^1$ | R$^2$ | R$^D$ | R$^E$ |
|---|---|---|---|---|
| 326 | H | H | H | H |
| 327 | Me | H | H | H |
| 328 | Me | Me | H | H |
| 329 | Cl | H | H | H |
| 330 | Cl | Me | H | H |
| 331 | Cl | Cl | H | H |
| 332 | Me | Cl | H | H |
| 333 | H | H | H | NO$_2$ |
| 334 | Me | H | H | NO$_2$ |
| 335 | Me | Me | H | NO$_2$ |
| 336 | Cl | H | H | NO$_2$ |
| 337 | Cl | Me | H | NO$_2$ |
| 338 | Cl | Cl | H | NO$_2$ |
| 339 | Me | Cl | H | NO$_2$ |
| 340 | H | H | H | CN |
| 341 | Me | H | H | CN |
| 342 | Me | Me | H | CN |
| 343 | Cl | H | H | CN |
| 344 | Cl | Me | H | CN |
| 345 | Cl | Cl | H | CN |
| 346 | Me | Cl | H | CN |
| 347 | H | H | Cl | H |
| 348 | Me | H | Cl | H |
| 349 | Me | Me | Cl | H |
| 350 | Cl | H | Cl | H |
| 351 | Cl | Me | Cl | H |
| 352 | Cl | Cl | Cl | H |
| 353 | Me | Cl | Cl | H |
| 354 | H | H | Cl | CF$_3$ |
| 355 | Me | H | Cl | CF$_3$ |
| 356 | Me | Me | Cl | CF$_3$ |
| 357 | Cl | H | Cl | CF$_3$ |
| 358 | Cl | Me | Cl | CF$_3$ |
| 359 | Cl | Cl | Cl | CF$_3$ |
| 360 | Me | Cl | Cl | CF$_3$ |
| 361 | H | H | H | CF$_3$ |
| 362 | Me | H | H | CF$_3$ |
| 363 | Me | Me | H | CF$_3$ |
| 364 | Cl | H | H | CF$_3$ |
| 365 | Cl | Me | H | CF$_3$ |
| 366 | Cl | Cl | H | CF$_3$ |
| 367 | Me | Cl | H | CF$_3$ |

TABLE 7

Compounds of the formula (I) according to the invention in which the substituents and indices are as defined below:

A = SO$_2$     E = bond     R$^1$ = CH$_3$
R$^2$ = CH$_3$     R$^3$ = H     R$^4$ = H
R$^5$ = 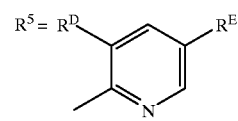     Q = Radical of formula (II)     R$^6$ = OH
R$^7$ = R$^A$, R$^B$     (X)$_1$ = O     Y = CH$_2$
Z = CH$_2$     v = 1

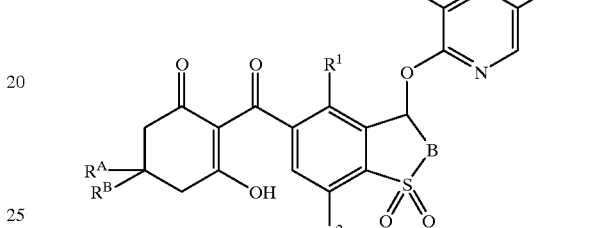

| No. | R$^A$ | R$^B$ | R$^1$ | R$^2$ | B | R$^D$ | R$^E$ |
|---|---|---|---|---|---|---|---|
| 368 | H | H | H | H | CH$_2$CH$_2$ | H | H |
| 369 | Me | H | H | H | CH$_2$CH$_2$ | H | H |
| 370 | Me | Me | H | H | CH$_2$CH$_2$ | H | H |
| 371 | H | H | Me | H | CH$_2$CH$_2$ | H | H |
| 372 | Me | H | Me | H | CH$_2$CH$_2$ | H | H |
| 373 | Me | Me | Me | H | CH$_2$CH$_2$ | H | H |
| 374 | H | H | Cl | H | CH$_2$CH$_2$ | H | H |
| 375 | Me | H | Cl | H | CH$_2$CH$_2$ | H | H |
| 376 | Me | Me | Cl | H | CH$_2$CH$_2$ | H | H |
| 377 | H | H | H | Me | CH$_2$CH$_2$ | H | H |
| 378 | Me | H | H | Me | CH$_2$CH$_2$ | H | H |
| 379 | Me | Me | H | Me | CH$_2$CH$_2$ | H | H |
| 380 | H | H | Me | Me | CH$_2$CH$_2$ | H | H |
| 381 | Me | H | Me | Me | CH$_2$CH$_2$ | H | H |
| 382 | Me | Me | Me | Me | CH$_2$CH$_2$ | H | H |
| 383 | H | H | Me | Cl | CH$_2$CH$_2$ | H | H |
| 384 | Me | H | Me | Cl | CH$_2$CH$_2$ | H | H |
| 385 | Me | Me | Me | Cl | CH$_2$CH$_2$ | H | H |
| 386 | H | H | Cl | Me | CH$_2$CH$_2$ | H | H |
| 387 | Me | H | Cl | Me | CH$_2$CH$_2$ | H | H |
| 388 | Me | Me | Cl | Me | CH$_2$CH$_2$ | H | H |
| 389 | H | H | H | Cl | CH$_2$CH$_2$ | H | H |
| 390 | Me | H | H | Cl | CH$_2$CH$_2$ | H | H |
| 391 | Me | Me | H | Cl | CH$_2$CH$_2$ | H | H |
| 392 | H | H | Cl | Cl | CH$_2$CH$_2$ | H | H |
| 393 | Me | H | Cl | Cl | CH$_2$CH$_2$ | H | H |
| 394 | Me | Me | Cl | Cl | CH$_2$CH$_2$ | H | H |
| 395 | H | H | H | H | CH$_2$CH$_2$ | H | NO$_2$ |
| 396 | Me | H | H | H | CH$_2$CH$_2$ | H | NO$_2$ |
| 397 | Me | Me | H | H | CH$_2$CH$_2$ | H | NO$_2$ |
| 398 | H | H | Me | H | CH$_2$CH$_2$ | H | NO$_2$ |
| 399 | Me | H | Me | H | CH$_2$CH$_2$ | H | NO$_2$ |
| 400 | Me | Me | Me | H | CH$_2$CH$_2$ | H | NO$_2$ |
| 401 | H | H | Cl | H | CH$_2$CH$_2$ | H | NO$_2$ |
| 402 | Me | H | Cl | H | CH$_2$CH$_2$ | H | NO$_2$ |
| 403 | Me | Me | Cl | H | CH$_2$CH$_2$ | H | NO$_2$ |
| 404 | H | H | H | Me | CH$_2$CH$_2$ | H | NO$_2$ |
| 405 | Me | H | H | Me | CH$_2$CH$_2$ | H | NO$_2$ |
| 406 | Me | Me | H | Me | CH$_2$CH$_2$ | H | NO$_2$ |
| 407 | H | H | Me | Me | CH$_2$CH$_2$ | H | NO$_2$ |
| 408 | Me | H | Me | Me | CH$_2$CH$_2$ | H | NO$_2$ |
| 409 | Me | Me | Me | Me | CH$_2$CH$_2$ | H | NO$_2$ |
| 410 | H | H | Me | Cl | CH$_2$CH$_2$ | H | NO$_2$ |
| 411 | Me | H | Me | Cl | CH$_2$CH$_2$ | H | NO$_2$ |
| 412 | Me | Me | Me | Cl | CH$_2$CH$_2$ | H | NO$_2$ |
| 413 | H | H | Cl | Me | CH$_2$CH$_2$ | H | NO$_2$ |
| 414 | Me | H | Cl | Me | CH$_2$CH$_2$ | H | NO$_2$ |

TABLE 7-continued

Compounds of the formula (I) according to the invention in which the substituents and indices are as defined below:

A = SO$_2$ E = bond R$^1$ = CH$_3$
R$^2$ = CH$_3$ R$^3$ = H R$^4$ = H

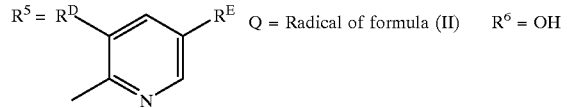

Q = Radical of formula (II) R$^6$ = OH

R$^7$ = R$^A$, R$^B$ (X)$_l$ = O Y = CH$_2$
Z = CH$_2$ v = 1

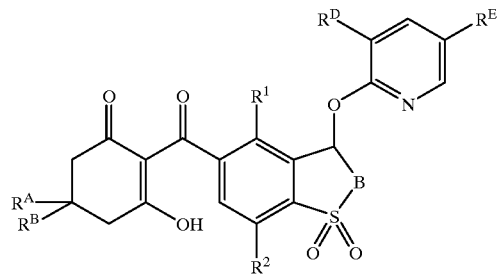

| No. | R$^A$ | R$^B$ | R$^1$ | R$^2$ | B | R$^D$ | R$^E$ |
|---|---|---|---|---|---|---|---|
| 415 | Me | Me | Cl | Me | CH$_2$CH$_2$ | H | NO$_2$ |
| 416 | H | H | H | Cl | CH$_2$CH$_2$ | H | NO$_2$ |
| 417 | Me | H | H | Cl | CH$_2$CH$_2$ | H | NO$_2$ |
| 418 | Me | Me | H | Cl | CH$_2$CH$_2$ | H | NO$_2$ |
| 419 | H | H | Cl | Cl | CH$_2$CH$_2$ | H | NO$_2$ |
| 420 | Me | H | Cl | Cl | CH$_2$CH$_2$ | H | NO$_2$ |
| 421 | Me | Me | Cl | Cl | CH$_2$CH$_2$ | H | NO$_2$ |
| 422 | H | H | H | H | CH$_2$CH$_2$ | H | CN |
| 423 | Me | H | H | H | CH$_2$CH$_2$ | H | CN |
| 424 | Me | Me | H | H | CH$_2$CH$_2$ | H | CN |
| 425 | H | H | Me | H | CH$_2$CH$_2$ | H | CN |
| 426 | Me | H | Me | H | CH$_2$CH$_2$ | H | CN |
| 427 | Me | Me | Me | H | CH$_2$CH$_2$ | H | CN |
| 428 | H | H | Cl | H | CH$_2$CH$_2$ | H | CN |
| 429 | Me | H | Cl | H | CH$_2$CH$_2$ | H | CN |
| 430 | Me | Me | Cl | H | CH$_2$CH$_2$ | H | CN |
| 431 | H | H | H | Me | CH$_2$CH$_2$ | H | CN |
| 432 | Me | H | H | Me | CH$_2$CH$_2$ | H | CN |
| 433 | Me | Me | H | Me | CH$_2$CH$_2$ | H | CN |
| 434 | H | H | Me | Me | CH$_2$CH$_2$ | H | CN |
| 435 | Me | H | Me | Me | CH$_2$CH$_2$ | H | CN |
| 436 | Me | Me | Me | Me | CH$_2$CH$_2$ | H | CN |
| 437 | H | H | Me | Cl | CH$_2$CH$_2$ | H | CN |
| 438 | Me | H | Me | Cl | CH$_2$CH$_2$ | H | CN |
| 439 | Me | Me | Me | Cl | CH$_2$CH$_2$ | H | CN |
| 440 | H | H | Cl | Me | CH$_2$CH$_2$ | H | CN |
| 441 | Me | H | Cl | Me | CH$_2$CH$_2$ | H | CN |
| 442 | Me | Me | Cl | Me | CH$_2$CH$_2$ | H | CN |
| 443 | H | H | H | Cl | CH$_2$CH$_2$ | H | CN |
| 444 | Me | H | H | Cl | CH$_2$CH$_2$ | H | CN |
| 445 | Me | Me | H | Cl | CH$_2$CH$_2$ | H | CN |
| 446 | H | H | Cl | Cl | CH$_2$CH$_2$ | H | CN |
| 447 | Me | H | Cl | Cl | CH$_2$CH$_2$ | H | CN |
| 448 | Me | Me | Cl | Cl | CH$_2$CH$_2$ | H | CN |
| 449 | H | H | H | H | CH$_2$CH$_2$ | Cl | H |
| 450 | Me | H | H | H | CH$_2$CH$_2$ | Cl | H |
| 451 | Me | Me | H | H | CH$_2$CH$_2$ | Cl | H |
| 452 | H | H | Me | H | CH$_2$CH$_2$ | Cl | H |
| 453 | Me | H | Me | H | CH$_2$CH$_2$ | Cl | H |
| 454 | Me | Me | Me | H | CH$_2$CH$_2$ | Cl | H |
| 455 | H | H | Cl | H | CH$_2$CH$_2$ | Cl | H |
| 456 | Me | H | Cl | H | CH$_2$CH$_2$ | Cl | H |
| 457 | Me | Me | Cl | H | CH$_2$CH$_2$ | Cl | H |
| 458 | H | H | H | Me | CH$_2$CH$_2$ | Cl | H |
| 459 | Me | H | H | Me | CH$_2$CH$_2$ | Cl | H |
| 460 | Me | Me | H | Me | CH$_2$CH$_2$ | Cl | H |
| 461 | H | H | Me | Me | CH$_2$CH$_2$ | Cl | H |

TABLE 7-continued

Compounds of the formula (I) according to the invention in which the substituents and indices are as defined below:

A = SO$_2$ E = bond R$^1$ = CH$_3$
R$^2$ = CH$_3$ R$^3$ = H R$^4$ = H

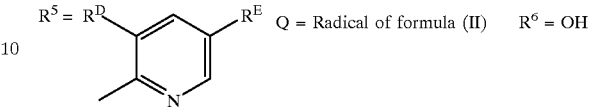

Q = Radical of formula (II) R$^6$ = OH

R$^7$ = R$^A$, R$^B$ (X)$_l$ = O Y = CH$_2$
Z = CH$_2$ v = 1

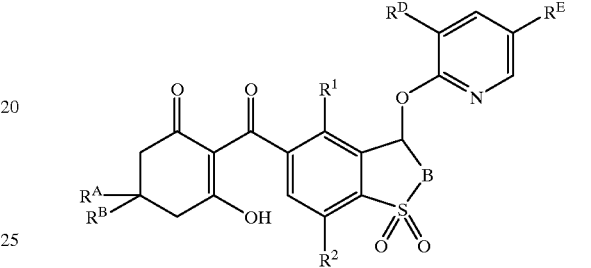

| No. | R$^A$ | R$^B$ | R$^1$ | R$^2$ | B | R$^D$ | R$^E$ |
|---|---|---|---|---|---|---|---|
| 462 | Me | H | Me | Me | CH$_2$CH$_2$ | Cl | H |
| 463 | Me | Me | Me | Me | CH$_2$CH$_2$ | Cl | H |
| 464 | H | H | Me | Cl | CH$_2$CH$_2$ | Cl | H |
| 465 | Me | H | Me | Cl | CH$_2$CH$_2$ | Cl | H |
| 466 | Me | Me | Me | Cl | CH$_2$CH$_2$ | Cl | H |
| 467 | H | H | Cl | Me | CH$_2$CH$_2$ | Cl | H |
| 468 | Me | H | Cl | Me | CH$_2$CH$_2$ | Cl | H |
| 469 | Me | Me | Cl | Me | CH$_2$CH$_2$ | Cl | H |
| 470 | H | H | H | Cl | CH$_2$CH$_2$ | Cl | H |
| 471 | Me | H | H | Cl | CH$_2$CH$_2$ | Cl | H |
| 472 | Me | Me | H | Cl | CH$_2$CH$_2$ | Cl | H |
| 473 | H | H | Cl | Cl | CH$_2$CH$_2$ | Cl | H |
| 474 | Me | H | Cl | Cl | CH$_2$CH$_2$ | Cl | H |
| 475 | Me | Me | Cl | Cl | CH$_2$CH$_2$ | Cl | H |
| 476 | H | H | H | H | CH$_2$CH$_2$ | Cl | CF$_3$ |
| 477 | Me | H | H | H | CH$_2$CH$_2$ | Cl | CF$_3$ |
| 478 | Me | Me | H | H | CH$_2$CH$_2$ | Cl | CF$_3$ |
| 479 | H | H | Me | H | CH$_2$CH$_2$ | Cl | CF$_3$ |
| 480 | Me | H | Me | H | CH$_2$CH$_2$ | Cl | CF$_3$ |
| 481 | Me | Me | Me | H | CH$_2$CH$_2$ | Cl | CF$_3$ |
| 482 | H | H | Cl | H | CH$_2$CH$_2$ | Cl | CF$_3$ |
| 483 | Me | H | Cl | H | CH$_2$CH$_2$ | Cl | CF$_3$ |
| 484 | Me | Me | Cl | H | CH$_2$CH$_2$ | Cl | CF$_3$ |
| 485 | H | H | H | Me | CH$_2$CH$_2$ | Cl | CF$_3$ |
| 486 | Me | H | H | Me | CH$_2$CH$_2$ | Cl | CF$_3$ |
| 487 | Me | Me | H | Me | CH$_2$CH$_2$ | Cl | CF$_3$ |
| 488 | H | H | Me | Me | CH$_2$CH$_2$ | Cl | CF$_3$ |
| 489 | Me | H | Me | Me | CH$_2$CH$_2$ | Cl | CF$_3$ |
| 490 | Me | Me | Me | Me | CH$_2$CH$_2$ | Cl | CF$_3$ |
| 491 | H | H | Me | Cl | CH$_2$CH$_2$ | Cl | CF$_3$ |
| 492 | Me | H | Me | Cl | CH$_2$CH$_2$ | Cl | CF$_3$ |
| 493 | Me | Me | Me | Cl | CH$_2$CH$_2$ | Cl | CF$_3$ |
| 494 | H | H | Cl | Me | CH$_2$CH$_2$ | Cl | CF$_3$ |
| 495 | Me | H | Cl | Me | CH$_2$CH$_2$ | Cl | CF$_3$ |
| 496 | Me | Me | Cl | Me | CH$_2$CH$_2$ | Cl | CF$_3$ |
| 497 | H | H | H | Cl | CH$_2$CH$_2$ | Cl | CF$_3$ |
| 498 | Me | H | H | Cl | CH$_2$CH$_2$ | Cl | CF$_3$ |
| 499 | Me | Me | H | Cl | CH$_2$CH$_2$ | Cl | CF$_3$ |
| 500 | H | H | Cl | Cl | CH$_2$CH$_2$ | Cl | CF$_3$ |
| 501 | Me | H | Cl | Cl | CH$_2$CH$_2$ | Cl | CF$_3$ |
| 502 | Me | Me | Cl | Cl | CH$_2$CH$_2$ | Cl | CF$_3$ |
| 503 | H | H | H | H | CH$_2$CH$_2$ | H | CF$_3$ |
| 504 | Me | H | H | H | CH$_2$CH$_2$ | H | CF$_3$ |
| 505 | Me | Me | H | H | CH$_2$CH$_2$ | H | CF$_3$ |
| 506 | H | H | Me | H | CH$_2$CH$_2$ | H | CF$_3$ |
| 507 | Me | H | Me | H | CH$_2$CH$_2$ | H | CF$_3$ |
| 508 | Me | Me | Me | H | CH$_2$CH$_2$ | H | CF$_3$ |

TABLE 7-continued

Compounds of the formula (I) according to the invention in which the substituents and indices are as defined below:

| | | |
|---|---|---|
| A = SO$_2$ | E = bond | R$^1$ = CH$_3$ |
| R$^2$ = CH$_3$ | R$^3$ = H | R$^4$ = H |
| R$^5$ = 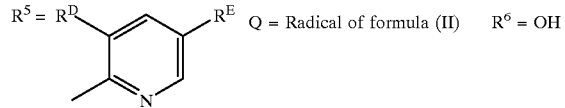 | Q = Radical of formula (II) | R$^6$ = OH |
| R$^7$ = R$^A$, R$^B$ | (X)$_1$ = O | Y = CH$_2$ |
| Z = CH$_2$ | v = 1 | |

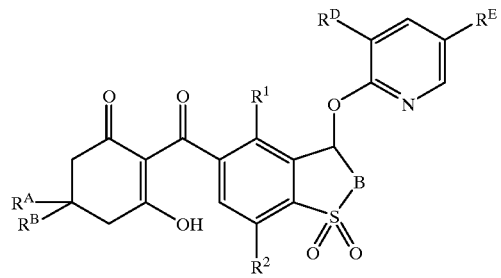

| No. | R$^A$ | R$^B$ | R$^1$ | R$^2$ | B | R$^D$ | R$^E$ |
|---|---|---|---|---|---|---|---|
| 509 | H | H | Cl | H | CH$_2$CH$_2$ | H | CF$_3$ |
| 510 | Me | H | Cl | H | CH$_2$CH$_2$ | H | CF$_3$ |
| 511 | Me | Me | Cl | H | CH$_2$CH$_2$ | H | CF$_3$ |
| 512 | H | H | H | Me | CH$_2$CH$_2$ | H | CF$_3$ |
| 513 | Me | H | H | Me | CH$_2$CH$_2$ | H | CF$_3$ |
| 514 | Me | Me | H | Me | CH$_2$CH$_2$ | H | CF$_3$ |
| 515 | H | H | Me | Me | CH$_2$CH$_2$ | H | CF$_3$ |
| 516 | Me | H | Me | Me | CH$_2$CH$_2$ | H | CF$_3$ |
| 517 | Me | Me | Me | Me | CH$_2$CH$_2$ | H | CF$_3$ |
| 518 | H | H | Me | Cl | CH$_2$CH$_2$ | H | CF$_3$ |
| 519 | Me | H | Me | Cl | CH$_2$CH$_2$ | H | CF$_3$ |
| 520 | Me | Me | Me | Cl | CH$_2$CH$_2$ | H | CF$_3$ |
| 521 | H | H | Cl | Me | CH$_2$CH$_2$ | H | CF$_3$ |
| 522 | Me | H | Cl | Me | CH$_2$CH$_2$ | H | CF$_3$ |
| 523 | Me | Me | Cl | Me | CH$_2$CH$_2$ | H | CF$_3$ |
| 524 | H | H | H | Cl | CH$_2$CH$_2$ | H | CF$_3$ |
| 525 | Me | H | H | Cl | CH$_2$CH$_2$ | H | CF$_3$ |
| 526 | Me | Me | H | Cl | CH$_2$CH$_2$ | H | CF$_3$ |
| 527 | H | H | Cl | Cl | CH$_2$CH$_2$ | H | CF$_3$ |
| 528 | Me | H | Cl | Cl | CH$_2$CH$_2$ | H | CF$_3$ |
| 529 | Me | Me | Cl | Cl | CH$_2$CH$_2$ | H | CF$_3$ |
| 530 | H | H | H | H | CH$_2$CH$_2$CH$_2$ | H | H |
| 531 | Me | H | H | H | CH$_2$CH$_2$CH$_2$ | H | H |
| 532 | Me | Me | H | H | CH$_2$CH$_2$CH$_2$ | H | H |
| 533 | H | H | Me | H | CH$_2$CH$_2$CH$_2$ | H | H |
| 534 | Me | H | Me | H | CH$_2$CH$_2$CH$_2$ | H | H |
| 535 | Me | Me | Me | H | CH$_2$CH$_2$CH$_2$ | H | H |
| 536 | H | H | Cl | H | CH$_2$CH$_2$CH$_2$ | H | H |
| 537 | Me | H | Cl | H | CH$_2$CH$_2$CH$_2$ | H | H |
| 538 | Me | Me | Cl | H | CH$_2$CH$_2$CH$_2$ | H | H |
| 539 | H | H | H | Me | CH$_2$CH$_2$CH$_2$ | H | H |
| 540 | Me | H | H | Me | CH$_2$CH$_2$CH$_2$ | H | H |
| 541 | Me | Me | H | Me | CH$_2$CH$_2$CH$_2$ | H | H |
| 542 | H | H | Me | Me | CH$_2$CH$_2$CH$_2$ | H | H |
| 543 | Me | H | Me | Me | CH$_2$CH$_2$CH$_2$ | H | H |
| 544 | Me | Me | Me | Me | CH$_2$CH$_2$CH$_2$ | H | H |
| 545 | H | H | Me | Cl | CH$_2$CH$_2$CH$_2$ | H | H |
| 546 | Me | H | Me | Cl | CH$_2$CH$_2$CH$_2$ | H | H |
| 547 | Me | Me | Me | Cl | CH$_2$CH$_2$CH$_2$ | H | H |
| 548 | H | H | Cl | Me | CH$_2$CH$_2$CH$_2$ | H | H |
| 550 | Me | H | Cl | Me | CH$_2$CH$_2$CH$_2$ | H | H |
| 551 | Me | Me | Cl | Me | CH$_2$CH$_2$CH$_2$ | H | H |
| 552 | H | H | H | Cl | CH$_2$CH$_2$CH$_2$ | H | H |
| 553 | Me | H | H | Cl | CH$_2$CH$_2$CH$_2$ | H | H |
| 554 | Me | Me | H | Cl | CH$_2$CH$_2$CH$_2$ | H | H |
| 555 | H | H | Cl | Cl | CH$_2$CH$_2$CH$_2$ | H | H |
| 556 | Me | H | Cl | Cl | CH$_2$CH$_2$CH$_2$ | H | H |
| 557 | Me | Me | Cl | Cl | CH$_2$CH$_2$CH$_2$ | H | H |
| 558 | H | H | H | H | CH$_2$CH$_2$CH$_2$ | H | NO$_2$ |
| 559 | Me | H | H | H | CH$_2$CH$_2$CH$_2$ | H | NO$_2$ |
| 560 | Me | Me | H | H | CH$_2$CH$_2$CH$_2$ | H | NO$_2$ |
| 561 | H | H | Me | H | CH$_2$CH$_2$CH$_2$ | H | NO$_2$ |
| 562 | Me | H | Me | H | CH$_2$CH$_2$CH$_2$ | H | NO$_2$ |
| 563 | Me | Me | Me | H | CH$_2$CH$_2$CH$_2$ | H | NO$_2$ |
| 564 | H | H | Cl | H | CH$_2$CH$_2$CH$_2$ | H | NO$_2$ |
| 565 | Me | H | Cl | H | CH$_2$CH$_2$CH$_2$ | H | NO$_2$ |
| 566 | Me | Me | Cl | H | CH$_2$CH$_2$CH$_2$ | H | NO$_2$ |
| 567 | H | H | H | Me | CH$_2$CH$_2$CH$_2$ | H | NO$_2$ |
| 568 | Me | H | H | Me | CH$_2$CH$_2$CH$_2$ | H | NO$_2$ |
| 569 | Me | Me | H | Me | CH$_2$CH$_2$CH$_2$ | H | NO$_2$ |
| 570 | H | H | Me | Me | CH$_2$CH$_2$CH$_2$ | H | NO$_2$ |
| 571 | Me | H | Me | Me | CH$_2$CH$_2$CH$_2$ | H | NO$_2$ |
| 572 | Me | Me | Me | Me | CH$_2$CH$_2$CH$_2$ | H | NO$_2$ |
| 573 | H | H | Me | Cl | CH$_2$CH$_2$CH$_2$ | H | NO$_2$ |
| 574 | Me | H | Me | Cl | CH$_2$CH$_2$CH$_2$ | H | NO$_2$ |
| 575 | Me | Me | Me | Cl | CH$_2$CH$_2$CH$_2$ | H | NO$_2$ |
| 576 | H | H | Cl | Me | CH$_2$CH$_2$CH$_2$ | H | NO$_2$ |
| 577 | Me | H | Cl | Me | CH$_2$CH$_2$CH$_2$ | H | NO$_2$ |
| 578 | Me | Me | Cl | Me | CH$_2$CH$_2$CH$_2$ | H | NO$_2$ |
| 579 | H | H | H | Cl | CH$_2$CH$_2$CH$_2$ | H | NO$_2$ |
| 580 | Me | H | H | Cl | CH$_2$CH$_2$CH$_2$ | H | NO$_2$ |
| 581 | Me | Me | H | Cl | CH$_2$CH$_2$CH$_2$ | H | NO$_2$ |
| 582 | H | H | Cl | Cl | CH$_2$CH$_2$CH$_2$ | H | NO$_2$ |
| 583 | Me | H | Cl | Cl | CH$_2$CH$_2$CH$_2$ | H | NO$_2$ |
| 584 | Me | Me | Cl | Cl | CH$_2$CH$_2$CH$_2$ | H | NO$_2$ |
| 585 | H | H | H | H | CH$_2$CH$_2$CH$_2$ | Cl | H |
| 586 | Me | H | H | H | CH$_2$CH$_2$CH$_2$ | Cl | H |
| 587 | Me | Me | H | H | CH$_2$CH$_2$CH$_2$ | Cl | H |
| 588 | H | H | Me | H | CH$_2$CH$_2$CH$_2$ | Cl | H |
| 589 | Me | H | Me | H | CH$_2$CH$_2$CH$_2$ | Cl | H |
| 590 | Me | Me | Me | H | CH$_2$CH$_2$CH$_2$ | Cl | H |
| 591 | H | H | Cl | H | CH$_2$CH$_2$CH$_2$ | Cl | H |
| 592 | Me | H | Cl | H | CH$_2$CH$_2$CH$_2$ | Cl | H |
| 593 | Me | Me | Cl | H | CH$_2$CH$_2$CH$_2$ | Cl | H |
| 594 | H | H | H | Me | CH$_2$CH$_2$CH$_2$ | Cl | H |
| 595 | Me | H | H | Me | CH$_2$CH$_2$CH$_2$ | Cl | H |
| 596 | Me | Me | H | Me | CH$_2$CH$_2$CH$_2$ | Cl | H |
| 597 | H | H | Me | Me | CH$_2$CH$_2$CH$_2$ | Cl | H |
| 598 | Me | H | Me | Me | CH$_2$CH$_2$CH$_2$ | Cl | H |
| 599 | Me | Me | Me | Me | CH$_2$CH$_2$CH$_2$ | Cl | H |
| 600 | H | H | Me | Cl | CH$_2$CH$_2$CH$_2$ | Cl | H |
| 601 | Me | H | Me | Cl | CH$_2$CH$_2$CH$_2$ | Cl | H |
| 602 | Me | Me | Me | Cl | CH$_2$CH$_2$CH$_2$ | Cl | H |
| 603 | H | H | Cl | Me | CH$_2$CH$_2$CH$_2$ | Cl | H |

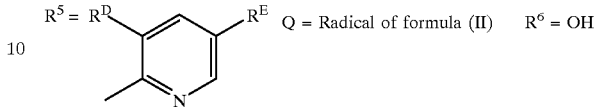

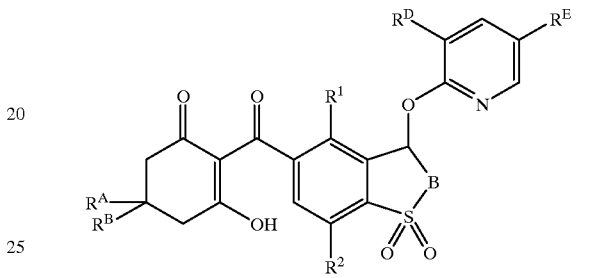

TABLE 7-continued

Compounds of the formula (I) according to the invention in which the substituents and indices are as defined below:

A = SO$_2$     E = bond     R$^1$ = CH$_3$
R$^2$ = CH$_3$  R$^3$ = H    R$^4$ = H R$^5$ = 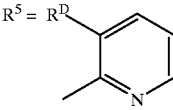

Q = Radical of formula (II)    R$^6$ = OH

R$^7$ = R$^A$, R$^B$    (X)$_1$ = O    Y = CH$_2$
Z = CH$_2$              v = 1

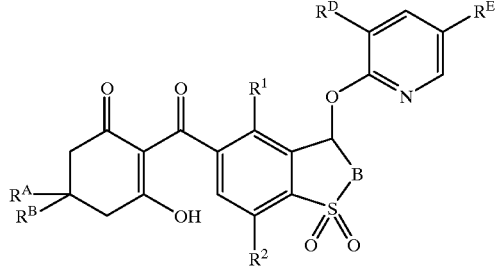

| No. | R$^A$ | R$^B$ | R$^1$ | R$^2$ | B | R$^D$ | R$^E$ |
|---|---|---|---|---|---|---|---|
| 604 | Me | H | Cl | Me | CH$_2$CH$_2$CH$_2$ | Cl | H |
| 605 | Me | Me | Cl | Me | CH$_2$CH$_2$CH$_2$ | Cl | H |
| 606 | H | H | H | Cl | CH$_2$CH$_2$CH$_2$ | Cl | H |
| 607 | Me | H | H | Cl | CH$_2$CH$_2$CH$_2$ | Cl | H |
| 608 | Me | Me | H | Cl | CH$_2$CH$_2$CH$_2$ | Cl | H |
| 609 | H | H | Cl | Cl | CH$_2$CH$_2$CH$_2$ | Cl | H |
| 610 | Me | H | Cl | Cl | CH$_2$CH$_2$CH$_2$ | Cl | H |
| 611 | Me | Me | Cl | Cl | CH$_2$CH$_2$CH$_2$ | Cl | H |
| 612 | H | H | H | H | CH$_2$CH$_2$CH$_2$ | Cl | CF$_3$ |
| 613 | Me | H | H | H | CH$_2$CH$_2$CH$_2$ | Cl | CF$_3$ |
| 614 | Me | Me | H | H | CH$_2$CH$_2$CH$_2$ | Cl | CF$_3$ |
| 615 | H | H | Me | H | CH$_2$CH$_2$CH$_2$ | Cl | CF$_3$ |
| 616 | Me | H | Me | H | CH$_2$CH$_2$CH$_2$ | Cl | CF$_3$ |
| 617 | Me | Me | Me | H | CH$_2$CH$_2$CH$_2$ | Cl | CF$_3$ |
| 618 | H | H | Cl | H | CH$_2$CH$_2$CH$_2$ | Cl | CF$_3$ |
| 619 | Me | H | Cl | H | CH$_2$CH$_2$CH$_2$ | Cl | CF$_3$ |
| 620 | Me | Me | Cl | H | CH$_2$CH$_2$CH$_2$ | Cl | CF$_3$ |
| 621 | H | H | H | Me | CH$_2$CH$_2$CH$_2$ | Cl | CF$_3$ |
| 622 | Me | H | H | Me | CH$_2$CH$_2$CH$_2$ | Cl | CF$_3$ |
| 623 | Me | Me | H | Me | CH$_2$CH$_2$CH$_2$ | Cl | CF$_3$ |
| 624 | H | H | Me | Me | CH$_2$CH$_2$CH$_2$ | Cl | CF$_3$ |
| 625 | Me | H | Me | Me | CH$_2$CH$_2$CH$_2$ | Cl | CF$_3$ |
| 626 | Me | Me | Me | Me | CH$_2$CH$_2$CH$_2$ | Cl | CF$_3$ |
| 627 | H | H | Me | Cl | CH$_2$CH$_2$CH$_2$ | Cl | CF$_3$ |
| 628 | Me | H | Me | Cl | CH$_2$CH$_2$CH$_2$ | Cl | CF$_3$ |
| 629 | Me | Me | Me | Cl | CH$_2$CH$_2$CH$_2$ | Cl | CF$_3$ |
| 630 | H | H | Cl | Me | CH$_2$CH$_2$CH$_2$ | Cl | CF$_3$ |
| 631 | Me | H | Cl | Me | CH$_2$CH$_2$CH$_2$ | Cl | CF$_3$ |
| 632 | Me | Me | Cl | Me | CH$_2$CH$_2$CH$_2$ | Cl | CF$_3$ |
| 633 | H | H | H | Cl | CH$_2$CH$_2$CH$_2$ | Cl | CF$_3$ |
| 634 | Me | H | H | Cl | CH$_2$CH$_2$CH$_2$ | Cl | CF$_3$ |
| 635 | Me | Me | H | Cl | CH$_2$CH$_2$CH$_2$ | Cl | CF$_3$ |
| 636 | H | H | Cl | Cl | CH$_2$CH$_2$CH$_2$ | Cl | CF$_3$ |
| 637 | Me | H | Cl | Cl | CH$_2$CH$_2$CH$_2$ | Cl | CF$_3$ |
| 638 | Me | Me | Cl | Cl | CH$_2$CH$_2$CH$_2$ | Cl | CF$_3$ |
| 639 | H | H | H | H | CH$_2$CH$_2$CH$_2$ | H | CF$_3$ |
| 640 | Me | H | H | H | CH$_2$CH$_2$CH$_2$ | H | CF$_3$ |
| 641 | Me | Me | H | H | CH$_2$CH$_2$CH$_2$ | H | CF$_3$ |
| 642 | H | H | Me | H | CH$_2$CH$_2$CH$_2$ | H | CF$_3$ |
| 643 | Me | H | Me | H | CH$_2$CH$_2$CH$_2$ | H | CF$_3$ |
| 644 | Me | Me | Me | H | CH$_2$CH$_2$CH$_2$ | H | CF$_3$ |

TABLE 7-continued

Compounds of the formula (I) according to the invention in which the substituents and indices are as defined below:

A = SO$_2$     E = bond     R$^1$ = CH$_3$
R$^2$ = CH$_3$  R$^3$ = H    R$^4$ = H R$^5$ = 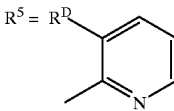

Q = Radical of formula (II)    R$^6$ = OH

R$^7$ = R$^A$, R$^B$    (X)$_1$ = O    Y = CH$_2$
Z = CH$_2$              v = 1

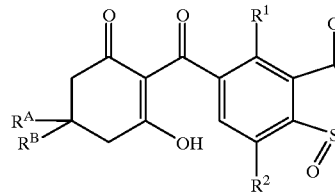

| No. | R$^A$ | R$^B$ | R$^1$ | R$^2$ | B | R$^D$ | R$^E$ |
|---|---|---|---|---|---|---|---|
| 645 | H | H | Cl | H | CH$_2$CH$_2$CH$_2$ | H | CF$_3$ |
| 646 | Me | H | Cl | H | CH$_2$CH$_2$CH$_2$ | H | CF$_3$ |
| 647 | Me | Me | Cl | H | CH$_2$CH$_2$CH$_2$ | H | CF$_3$ |
| 648 | H | H | H | Me | CH$_2$CH$_2$CH$_2$ | H | CF$_3$ |
| 649 | Me | H | H | Me | CH$_2$CH$_2$CH$_2$ | H | CF$_3$ |
| 650 | Me | Me | H | Me | CH$_2$CH$_2$CH$_2$ | H | CF$_3$ |
| 651 | H | H | Me | Me | CH$_2$CH$_2$CH$_2$ | H | CF$_3$ |
| 652 | Me | H | Me | Me | CH$_2$CH$_2$CH$_2$ | H | CF$_3$ |
| 653 | Me | Me | Me | Me | CH$_2$CH$_2$CH$_2$ | H | CF$_3$ |
| 654 | H | H | Me | Cl | CH$_2$CH$_2$CH$_2$ | H | CF$_3$ |
| 655 | Me | H | Me | Cl | CH$_2$CH$_2$CH$_2$ | H | CF$_3$ |
| 656 | Me | Me | Me | Cl | CH$_2$CH$_2$CH$_2$ | H | CF$_3$ |
| 657 | H | H | Cl | Me | CH$_2$CH$_2$CH$_2$ | H | CF$_3$ |
| 658 | Me | H | Cl | Me | CH$_2$CH$_2$CH$_2$ | H | CF$_3$ |
| 659 | Me | Me | Cl | Me | CH$_2$CH$_2$CH$_2$ | H | CF$_3$ |
| 660 | H | H | H | Cl | CH$_2$CH$_2$CH$_2$ | H | CF$_3$ |
| 661 | Me | H | H | Cl | CH$_2$CH$_2$CH$_2$ | H | CF$_3$ |
| 662 | Me | Me | H | Cl | CH$_2$CH$_2$CH$_2$ | H | CF$_3$ |
| 663 | H | H | Cl | Cl | CH$_2$CH$_2$CH$_2$ | H | CF$_3$ |
| 664 | Me | H | Cl | Cl | CH$_2$CH$_2$CH$_2$ | H | CF$_3$ |
| 665 | Me | Me | Cl | Cl | CH$_2$CH$_2$CH$_2$ | H | CF$_3$ |

TABLE 8

Compounds of the formula (I) according to the invention in which the substituents and indices are as defined below:

| A = | SO$_2$ | B = | CH$_2$CH$_2$ | R$^1$ = | CH$_3$ |
|---|---|---|---|---|---|
| R$^2$ = | CH$_3$ | R$^3$ = | H | Q = | Radical of formula (II) |
| R$^6$ = | OH | Y = | CH$_2$ | Z = | CH$_2$ |
| v = | 1 | w = | 0 | | |

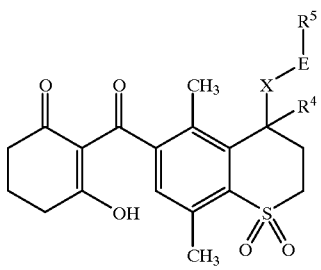

| No. | (X)$_1$ | E | R$^4$ | R$^5$ | Physical data |
|---|---|---|---|---|---|
| 666 | O | bond | H | phenyl | |
| 667 | O | bond | H | 4-nitrophenyl | |
| 668 | O | bond | H | 4-chlorophenyl | |
| 669 | O | bond | H | 3-pyridyl | |
| 670 | O | bond | H | 5-trifluoromethyl-2-pyridyl | |
| 671 | O | bond | H | 2-methyl-1-pyrrolyl | |
| 672 | O | bond | H | 4-methyl-2-thienyl | |
| 673 | O | bond | H | 3-methylthio-2-pyridyl | |
| 674 | O | bond | H | 5-methylaminocarbonyl-2-pyridyl | |
| 675 | O | bond | H | 1,2,3-thidiazol-4-yl | m.p. 192–196° C. |
| 676 | O | bond | H | 4,6-dimethoxy-1,3,5-triazin-2-yl | |
| 677 | S | bond | H | phenyl | |
| 678 | S | bond | H | 4-nitrophenyl | |
| 679 | S | bond | H | 4-chlorophenyl | |
| 680 | S | bond | H | 2-pyridyl | m.p. 212–215° C. |
| 681 | S | bond | H | 5-nitro-2-pyridyl | |
| 682 | S | bond | H | 2-pyrimidinyl | m.p. 270° C. |
| 683 | S | bond | H | 4,6-dimethyl-2-pyrimidinyl | |
| 684 | S | bond | H | 4,6-dimethoxy-2-pyrimidinyl | |
| 685 | S | bond | H | 2-pyrazinyl | |
| 686 | S | bond | H | 1,2,3-thidiazol-4-yl | |
| 687 | S | bond | H | 4,6-dimethoxy-1,3,5-triazin-2-yl | |
| 688 | NH | bond | H | phenyl | |
| 689 | NH | bond | H | 4-nitrophenyl | |
| 690 | NH | bond | H | 4-chlorophenyl | |
| 691 | NH | bond | H | pyridyl | |
| 692 | NH | bond | H | 5-nitro-2-pyridyl | |
| 693 | NH | bond | H | 2-pyrimidinyl | |
| 694 | NH | bond | H | 4,6-dimethyl-2-pyrimidinyl | |
| 695 | NH | bond | H | 4,6-dimethoxy-2-pyrimidinyl | |
| 696 | NH | bond | H | 2-pyrazinyl | |
| 697 | NH | bond | H | 1,2,3-thidiazol-4-yl | |
| 698 | NH | bond | H | 4,6-dimethoxy-1,3,5-triazine-2-yl | |
| 699 | NMe | bond | H | phenyl | |
| 700 | NMe | bond | H | 4-nitrophenyl | |
| 701 | NMe | bond | H | 4-chlorophenyl | |
| 702 | NMe | bond | H | pyridyl | |
| 703 | NMe | bond | H | 5-nitro-2-pyridyl | |
| 704 | NMe | bond | H | 2-pyrimidinyl | |
| 705 | NMe | bond | H | 4,6-dimethyl-2-pyrimidinyl | |
| 706 | NMe | bond | H | 4,6-dimethoxy-2-pyrimidinyl | |
| 707 | NMe | bond | H | 2-pyrazinyl | |
| 708 | NMe | bond | H | 1,2,3-thidiazol-4-yl | |
| 709 | NMe | bond | H | 4,6-dimethoxy-1,3,5-triazin-2-yl | |
| 710 | NCHO | bond | H | phenyl | |
| 711 | NCHO | bond | H | 4-nitrophenyl | |
| 712 | NCHO | bond | H | 4-chlorophenyl | |
| 713 | NCHO | bond | H | pyridyl | |
| 714 | NCHO | bond | H | 5-nitro-2-pyridyl | |
| 715 | NCHO | bond | H | 2-pyrimidinyl | |
| 716 | NCHO | bond | H | 4,6-dimethyl-2-pyrimidinyl | |
| 717 | NCHO | bond | H | 4,6-dimethoxy-2-pyrimidinyl | |
| 718 | NCHO | bond | H | 2-pyrazinyl | |
| 719 | NCHO | bond | H | 1,2,3-thidiazol-4-yl | |
| 720 | NCHO | bond | H | 4,6-dimethoxy-1,3,5-triazin-2-yl | |

TABLE 8-continued

Compounds of the formula (I) according to the invention in which the substituents and indices are as defined below:

| | | | | |
|---|---|---|---|---|
| 721 | O | CH₂ | H | 2-chloro-4-nitro-phenyl |
| 722 | O | CH₂ | H | 4-nitrophenyl |
| 723 | O | CH₂ | H | 4-chlorophenyl |
| 724 | O | CH₂ | H | pyridyl |
| 725 | O | CH₂ | H | 5-nitro-2-pyridyl |
| 726 | O | CH₂ | H | 2-pyrimidinyl |
| 727 | O | CH₂ | H | 4,6-dimethyl-2-pyrimidinyl |
| 728 | O | CH₂ | H | 4,6-dimethoxy-2-pyrimidinyl |
| 729 | O | CH₂ | H | 2-pyrazinyl |
| 730 | O | CH₂ | H | 1,2,3-thidiazol-4-yl |
| 731 | O | CH₂ | H | 4,6-dimethoxy-1,3,5-triazin-2-yl |
| 732 | S | CH₂ | H | phenyl |
| 733 | S | CH₂ | H | 4-nitrophenyl |
| 734 | S | CH₂ | H | 4-chlorophenyl |
| 735 | S | CH₂ | H | pyridyl |
| 736 | S | CH₂ | H | 5-nitro-2-pyridyl |
| 737 | S | CH₂ | H | 2-pyrimidinyl |
| 738 | S | CH₂ | H | 4,6-dimethyl-2-pyrimidinyl |
| 739 | S | CH₂ | H | 4,6-dimethoxy-2-pyrimidinyl |
| 740 | S | CH₂ | H | 2-pyrazinyl |
| 741 | S | CH₂ | H | 1,2,3-thidiazol-4-yl |
| 742 | S | CH₂ | H | 4,6-dimethoxy-1,3,5-triazin-2-yl |
| 743 | NH | CH₂ | H | phenyl |
| 744 | NH | CH₂ | H | 4-nitrophenyl |
| 745 | NH | CH₂ | H | 4-chlorophenyl |
| 746 | NH | CH₂ | H | pyridyl |
| 747 | NH | CH₂ | H | 5-nitro-2-pyridyl |
| 748 | NH | CH₂ | H | 2-pyrimidinyl |
| 749 | NH | CH₂ | H | 4,6-dimethyl-2-pyrimidinyl |
| 750 | NH | CH₂ | H | 4,6-dimethoxy-2-pyrimidinyl |
| 751 | NH | CH₂ | H | 2-pyrazinyl |
| 752 | NH | CH₂ | H | 1,2,3-thidiazol-4-yl |
| 753 | NH | CH₂ | H | 4,6-dimethoxy-1,3,5-triazin-2-yl |
| 754 | NMe | CH₂ | H | phenyl |
| 755 | NMe | CH₂ | H | 4-nitrophenyl |
| 756 | NMe | CH₂ | H | 4-chlorophenyl |
| 757 | NMe | CH₂ | H | pyridyl |
| 758 | NMe | CH₂ | H | 5-nitro-2-pyridyl |
| 759 | NMe | CH₂ | H | 2-pyrimidinyl |
| 760 | NMe | CH₂ | H | 4,6-dimethyl-2-pyrimidinyl |
| 761 | NMe | CH₂ | H | 4,6-dimethoxy-2-pyrimidinyl |
| 762 | NMe | CH₂ | H | 2-pyrazinyl |
| 763 | NMe | CH₂ | H | 1,2,3-thidiazol-4-yl |
| 764 | NMe | CH₂ | H | 4,6-dimethoxy-1,3,5-triazin-2-yl |
| 765 | NCHO | CH₂ | H | phenyl |
| 766 | NCHO | CH₂ | H | 4-nitrophenyl |
| 767 | NCHO | CH₂ | H | 4-chlorophenyl |
| 768 | NCHO | CH₂ | H | pyridyl |
| 769 | NCHO | CH₂ | H | 5-nitro-2-pyridyl |
| 770 | NCHO | CH₂ | H | 2-pyrimidinyl |
| 771 | NCHO | CH₂ | H | 4,6-dimethyl-2-pyrimidinyl |
| 772 | NCHO | CH₂ | H | 4,6-dimethoxy-2-pyrimidinyl |
| 773 | NCHO | CH₂ | H | 2-pyrazinyl |
| 774 | NCHO | CH₂ | H | 1,2,3-thidiazol-4-yl |
| 775 | NCHO | CH₂ | H | 4,6-dimethoxy-1,3,5-triazin-2-yl |
| 776 | O | C(O) | H | 3-difluoromethoxyphenyl |
| 777 | O | C(O) | H | 4-nitrophenyl |
| 778 | O | C(O) | H | 4-chlorophenyl |
| 779 | O | C(O) | H | pyridyl |
| 780 | O | C(O) | H | 5-nitro-2-pyridyl |
| 781 | O | C(O) | H | 2-pyrimidinyl |
| 782 | O | C(O) | H | 4,6-dimethyl-2-pyrimidinyl |
| 783 | O | C(O) | H | 4,6-dimethoxy-2-pyrimidinyl |
| 784 | O | C(O) | H | 2-pyrazinyl |
| 785 | O | C(O) | H | 1,2,3-thidiazol-4-yl |
| 786 | O | C(O) | H | 4,6-dimethoxy-1,3,5-triazin-2-yl |
| 787 | S | C(O) | H | phenyl |
| 788 | S | C(O) | H | 4-nitrophenyl |
| 789 | S | C(O) | H | 4-chlorophenyl |
| 790 | S | C(O) | H | pyridyl |
| 791 | S | C(O) | H | 5-nitro-2-pyridyl |
| 792 | S | C(O) | H | 2-pyrimidinyl |
| 793 | S | C(O) | H | 4,6-dimethyl-2-pyrimidinyl |
| 794 | S | C(O) | H | 4,6-dimethoxy-2-pyrimidinyl |
| 795 | S | C(O) | H | 2-pyrazinyl |
| 796 | S | C(O) | H | 1,2,3-thidiazol-4-yl |

TABLE 8-continued

Compounds of the formula (I) according to the invention in which the substituents and indices are as defined below:

| | | | | |
|---|---|---|---|---|
| 797 | S | C(O) | H | 4,6-dimethoxy-1,3,5-triazin-2-yl |
| 798 | NH | C(O) | H | phenyl |
| 799 | NH | C(O) | H | 4-nitrophenyl |
| 800 | NH | C(O) | H | 4-chlorophenyl |
| 801 | NH | C(O) | H | pyridyl |
| 802 | NH | C(O) | H | 5-nitro-2-pyridyl |
| 803 | NH | C(O) | H | 2-pyrimidinyl |
| 804 | NH | C(O) | H | 4,6-dimethyl-2-pyrimidinyl |
| 805 | NH | C(O) | H | 4,6-dimethoxy-2-pyrimidinyl |
| 806 | NH | C(O) | H | 2-pyrazinyl |
| 807 | NH | C(O) | H | 1,2,3-thidiazol-4-yl |
| 808 | NH | C(O) | H | 4,6-dimethoxy-1,3,5-triazin-2-yl |
| 809 | NMe | C(O) | H | phenyl |
| 810 | NMe | C(O) | H | 4-nitrophenyl |
| 811 | NMe | C(O) | H | 4-chlorophenyl |
| 812 | NMe | C(O) | H | pyridyl |
| 813 | NMe | C(O) | H | 5-nitro-2-pyridyl |
| 814 | NMe | C(O) | H | 2-pyrimidinyl |
| 815 | NMe | C(O) | H | 4,6-dimethyl-2-pyrimidinyl |
| 816 | NMe | C(O) | H | 4,6-dimethoxy-2-pyrimidinyl |
| 817 | NMe | C(O) | H | 2-pyrazinyl |
| 818 | NMe | C(O) | H | 1,2,3-thidiazol-4-yl |
| 819 | NMe | C(O) | H | 4,6-dimethoxy-1,3,5-triazin-2-yl |
| 820 | NCHO | C(O) | H | phenyl |
| 821 | NCHO | C(O) | H | 4-nitrophenyl |
| 822 | NCHO | C(O) | H | 4-chlorophenyl |
| 823 | NCHO | C(O) | H | pyridyl |
| 824 | NCHO | C(O) | H | 5-nitro-2-pyridyl |
| 825 | NCHO | C(O) | H | 2-pyrimidinyl |
| 826 | NCHO | C(O) | H | 4,6-dimethyl-2-pyrimidinyl |
| 827 | NCHO | C(O) | H | 4,6-dimethoxy-2-pyrimidinyl |
| 828 | NCHO | C(O) | H | 2-pyrazinyl |
| 829 | NCHO | C(O) | H | 1,2,3-thidiazol-4-yl |
| 830 | NCHO | C(O) | H | 4,6-dimethoxy-1,3,5-triazin-2-yl |
| 831 | O | $SO_2$ | H | phenyl |
| 832 | O | $SO_2$ | H | 4-nitrophenyl |
| 833 | O | $SO_2$ | H | 4-chlorophenyl |
| 834 | O | $SO_2$ | H | pyridyl |
| 835 | O | $SO_2$ | H | 5-nitro-2-pyridyl |
| 836 | O | $SO_2$ | H | 2-pyrimidinyl |
| 837 | O | $SO_2$ | H | 4,6-dimethyl-2-pyrimidinyl |
| 838 | O | $SO_2$ | H | 4,6-dimethoxy-2-pyrimidinyl |
| 839 | O | $SO_2$ | H | 2-pyrazinyl |
| 840 | O | $SO_2$ | H | 1,2,3-thidiazol-4-yl |
| 841 | O | $SO_2$ | H | 4,6-dimethoxy-1,3,5-triazin-2-yl |
| 842 | NH | $SO_2$ | H | phenyl |
| 843 | NH | $SO_2$ | H | 4-nitrophenyl |
| 844 | NH | $SO_2$ | H | 4-chlorophenyl |
| 845 | NH | $SO_2$ | H | pyridyl |
| 846 | NH | $SO_2$ | H | 5-nitro-2-pyridyl |
| 847 | NH | $SO_2$ | H | 2-pyrimidinyl |
| 848 | NH | $SO_2$ | H | 4,6-dimethyl-2-pyrimidinyl |
| 849 | NH | $SO_2$ | H | 4,6-dimethoxy-2-pyrimidinyl |
| 850 | NH | $SO_2$ | H | 2-pyrazinyl |
| 851 | NH | $SO_2$ | H | 1,2,3-thidiazol-4-yl |
| 852 | NH | $SO_2$ | H | 4,6-dimethoxy-1,3,5-triazin-2-yl |
| 853 | NMe | $SO_2$ | H | phenyl |
| 854 | NMe | $SO_2$ | H | 4-nitrophenyl |
| 855 | NMe | $SO_2$ | H | 4-chlorophenyl |
| 856 | NMe | $SO_2$ | H | pyridyl |
| 857 | NMe | $SO_2$ | H | 5-nitro-2-pyridyl |
| 858 | NMe | $SO_2$ | H | 2-pyrimidinyl |
| 859 | NMe | $SO_2$ | H | 4,6-dimethyl-2-pyrimidinyl |
| 860 | NMe | $SO_2$ | H | 4,6-dimethoxy-2-pyrimidinyl |
| 861 | NMe | $SO_2$ | H | 2-pyrazinyl |
| 862 | NMe | $SO_2$ | H | 1,2,3-thidiazol-4-yl |
| 863 | NMe | $SO_2$ | H | 4,6-dimethoxy-1,3,5-triazin-2-yl |
| 864 | O | $CH_2$ | Me | phenyl |
| 865 | O | $CH_2$ | Me | 4-nitrophenyl |
| 866 | O | $CH_2$ | Me | 4-chlorophenyl |
| 867 | O | $CH_2$ | Me | pyridyl |
| 868 | O | $CH_2$ | Me | 5-nitro-2-pyridyl |
| 869 | O | $CH_2$ | Me | 2-pyrimidinyl |
| 870 | O | $CH_2$ | Me | 4,6-dimethyl-2-pyrimidinyl |
| 871 | O | $CH_2$ | Me | 4,6-dimethoxy-2-pyrimidinyl |
| 872 | O | $CH_2$ | Me | 2-pyrazinyl |

TABLE 8-continued

Compounds of the formula (I) according to the invention in which the substituents and indices are as defined below:

| 873 | O | CH₂ | Me | 1,2,3-thidiazol-4-yl |
| 874 | O | CH₂ | Me | 4,6-dimethoxy-1,3,5-triazin-2-yl |
| 875 | S | CH₂ | Me | phenyl |
| 876 | S | CH₂ | Me | 4-nitrophenyl |
| 877 | S | CH₂ | Me | 4-chlorophenyl |
| 878 | S | CH₂ | Me | pyridyl |
| 879 | S | CH₂ | Me | 5-nitro-2-pyridyl |
| 880 | S | CH₂ | Me | 2-pyrimidinyl |
| 881 | S | CH₂ | Me | 4,6-dimethyl-2-pyrimidinyl |
| 882 | S | CH₂ | Me | 4,6-dimethoxy-2-pyrimidinyl |
| 883 | S | CH₂ | Me | 2-pyrazinyl |
| 884 | S | CH₂ | Me | 1,2,3-thidiazol-4-yl |
| 885 | S | CH₂ | Me | 4,6-dimethoxy-1,3,5-triazin-2-yl |
| 886 | NH | CH₂ | Me | phenyl |
| 887 | NH | CH₂ | Me | 4-nitrophenyl |
| 888 | NH | CH₂ | Me | 4-chlorophenyl |
| 889 | NH | CH₂ | Me | pyridyl |
| 890 | NH | CH₂ | Me | 5-nitro-2-pyridyl |
| 891 | NH | CH₂ | Me | 2-pyrimidinyl |
| 892 | NH | CH₂ | Me | 4,6-dimethyl-2-pyrimidinyl |
| 893 | NH | CH₂ | Me | 4,6-dimethoxy-2-pyrimidinyl |
| 894 | NH | CH₂ | Me | 2-pyrazinyl |
| 895 | NH | CH₂ | Me | 1,2,3-thidiazol-4-yl |
| 896 | NH | CH₂ | Me | 4,6-dimethoxy-1,3,5-triazin-2-yl |
| 897 | NMe | CH₂ | Me | phenyl |
| 898 | NMe | CH₂ | Me | 4-nitrophenyl |
| 899 | NMe | CH₂ | Me | 4-chlorophenyl |
| 900 | NMe | CH₂ | Me | pyridyl |
| 901 | NMe | CH₂ | Me | 5-nitro-2-pyridyl |
| 902 | NMe | CH₂ | Me | 2-pyrimidinyl |
| 903 | NMe | CH₂ | Me | 4,6-dimethyl-2-pyrimidinyl |
| 904 | NMe | CH₂ | Me | 4,6-dimethoxy-2-pyrimidinyl |
| 905 | NMe | CH₂ | Me | 2-pyrazinyl |
| 906 | NMe | CH₂ | Me | 1,2,3-thidiazol-4-yl |
| 907 | NMe | CH₂ | Me | 4,6-dimethoxy-1,3,5-triazin-2-yl |
| 908 | NCHO | CH₂ | Me | phenyl |
| 909 | NCHO | CH₂ | Me | 4-nitrophenyl |
| 910 | NCHO | CH₂ | Me | 4-chlorophenyl |
| 911 | NCHO | CH₂ | Me | pyridyl |
| 912 | NCHO | CH₂ | Me | 5-nitro-2-pyridyl |
| 913 | NCHO | CH₂ | Me | 2-pyrimidinyl |
| 914 | NCHO | CH₂ | Me | 4,6-dimethyl-2-pyrimidinyl |
| 915 | NCHO | CH₂ | Me | 4,6-dimethoxy-2-pyrimidinyl |
| 916 | NCHO | CH₂ | Me | 2-pyrazinyl |
| 917 | NCHO | CH₂ | Me | 1,2,3-thidiazol-4-yl |
| 918 | NCHO | CH₂ | Me | 4,6-dimethoxy-1,3,5-triazin-2-yl |
| 919 | O | C(O) | Me | phenyl |
| 920 | O | C(O) | Me | 4-nitrophenyl |
| 921 | O | C(O) | Me | 4-chlorophenyl |
| 922 | O | C(O) | Me | pyridyl |
| 923 | O | C(O) | Me | 5-nitro-2-pyridyl |
| 924 | O | C(O) | Me | 2-pyrimidinyl |
| 925 | O | C(O) | Me | 4,6-dimethyl-2-pyrimidinyl |
| 926 | O | C(O) | Me | 4,6-dimethoxy-2-pyrimidinyl |
| 927 | O | C(O) | Me | 2-pyrazinyl |
| 928 | O | C(O) | Me | 1,2,3-thidiazol-4-yl |

TABLE 8-continued

Compounds of the formula (I) according to the invention in which the substituents and indices are as defined below:

| | | | | |
|---|---|---|---|---|
| 929 | O | C(O) | Me | 4,6-dimethoxy-1,3,5-triazin-2-yl |
| 930 | S | C(O) | Me | phenyl |
| 931 | S | C(O) | Me | 4-nitrophenyl |
| 932 | S | C(O) | Me | 4-chlorophenyl |
| 933 | S | C(O) | Me | pyridyl |
| 934 | S | C(O) | Me | 5-nitro-2-pyridyl |
| 935 | S | C(O) | Me | 2-pyrimidinyl |
| 936 | S | C(O) | Me | 4,6-dimethyl-2-pyrimidinyl |
| 937 | S | C(O) | Me | 4,6-dimethoxy-2-pyrimidinyl |
| 938 | S | C(O) | Me | 2-pyrazinyl |
| 939 | S | C(O) | Me | 1,2,3-thidiazol-4-yl |
| 940 | S | C(O) | Me | 4,6-dimethoxy-1,3,5-triazin-2-yl |
| 941 | NH | C(O) | Me | phenyl |
| 942 | NH | C(O) | Me | 4-nitrophenyl |
| 943 | NH | C(O) | Me | 4-chlorophenyl |
| 944 | NH | C(O) | Me | pyridyl |
| 945 | NH | C(O) | Me | 5-nitro-2-pyridyl |
| 946 | NH | C(O) | Me | 2-pyrimidinyl |
| 947 | NH | C(O) | Me | 4,6-dimethyl-2-pyrimidinyl |
| 948 | NH | C(O) | Me | 4,6-dimethoxy-2-pyrimidinyl |
| 949 | NH | C(O) | Me | 2-pyrazinyl |
| 950 | NH | C(O) | Me | 1,2,3-thidiazol-4-yl |
| 951 | NH | C(O) | Me | 4,6-dimethoxy-1,3,5-triazin-2-yl |
| 952 | NMe | C(O) | Me | phenyl |
| 953 | NMe | C(O) | Me | 4-nitrophenyl |
| 954 | NMe | C(O) | Me | 4-chlorophenyl |
| 955 | NMe | C(O) | Me | pyridyl |
| 956 | NMe | C(O) | Me | 5-nitro-2-pyridyl |
| 957 | NMe | C(O) | Me | 2-pyrimidinyl |
| 958 | NMe | C(O) | Me | 4,6-dimethyl-2-pyrimidinyl |
| 959 | NMe | C(O) | Me | 4,6-dimethoxy-2-pyrimidinyl |
| 960 | NMe | C(O) | Me | 2-pyrazinyl |
| 961 | NMe | C(O) | Me | 1,2,3-thidiazol-4-yl |
| 962 | NMe | C(O) | Me | 4,6-dimethoxy-1,3,5-triazin-2-yl |
| 963 | NCHO | C(O) | Me | phenyl |
| 964 | NCHO | C(O) | Me | 4-nitrophenyl |
| 965 | NCHO | C(O) | Me | 4-chlorophenyl |
| 966 | NCHO | C(O) | Me | pyridyl |
| 967 | NCHO | C(O) | Me | 5-nitro-2-pyridyl |
| 968 | NCHO | C(O) | Me | 2-pyrimidinyl |
| 969 | NCHO | C(O) | Me | 4,6-dimethyl-2-pyrimidinyl |
| 970 | NCHO | C(O) | Me | 4,6-dimethoxy-2-pyrimidinyl |
| 971 | NCHO | C(O) | Me | 2-pyrazinyl |
| 972 | NCHO | C(O) | Me | 1,2,3-thidiazol-4-yl |
| 973 | NCHO | C(O) | Me | 4,6-dimethoxy-1,3,5-triazin-2-yl |

TABLE 9

Compounds of the formula (I) according to the invention in which the substituents and indices are as defined below:

| | | | | | |
|---|---|---|---|---|---|
| A = | SO$_2$ | E = | bond | R$^1$ = | CH$_3$ |
| R$^2$ = | CH$_3$ | R$^3$ = | H | R$^4$ = | H |
| R$^5$ = | 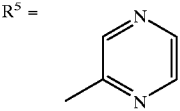 | Q = | radical of formula (II) | | |
| (X)$_1$ = | O | Y = | CH$_2$ | Z = | CH$_2$ |
| v = | 1 | w = | 0 | | |

TABLE 9-continued

Compounds of the formula (I) according to the invention in which the substituents and indices are as defined below:

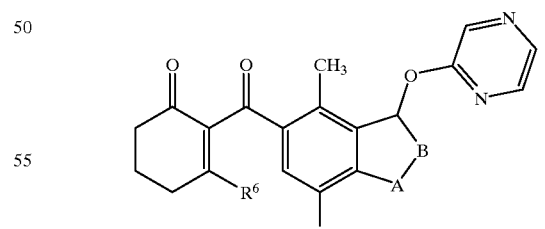

| No. | R$^6$ | A | B |
|---|---|---|---|
| 974 | OBz | SO$_2$ | CH$_2$CH$_2$ |
| 975 | SH | SO$_2$ | CH$_2$CH$_2$ |
| 976 | SPh | SO$_2$ | CH$_2$CH$_2$ |
| 977 | Cl | SO$_2$ | CH$_2$CH$_2$ |
| 978 | OH | SO | CH$_2$CH$_2$ |
| 979 | SH | SO | CH$_2$CH$_2$ |

TABLE 9-continued

Compounds of the formula (I) according to the invention in which the substituents and indices are as defined below:

| | | | |
|---|---|---|---|
| 980 | SPh | SO | CH$_2$CH$_2$ |
| 981 | Cl | SO | CH$_2$CH$_2$ |
| 982 | OH | S | CH$_2$CH$_2$ |
| 983 | SH | S | CH$_2$CH$_2$ |
| 984 | SPh | S | CH$_2$CH$_2$ |
| 985 | Cl | S | CH$_2$CH$_2$ |
| 986 | OH | CH$_2$ | CH$_2$CH$_2$ |
| 987 | SH | CH$_2$ | CH$_2$CH$_2$ |
| 988 | SPh | CH$_2$ | CH$_2$CH$_2$ |
| 989 | Cl | CH$_2$ | CH$_2$CH$_2$ |
| 990 | OH | NHSO$_2$Me | CH$_2$CH$_2$ |
| 991 | SH | NHSO$_2$Me | CH$_2$CH$_2$ |
| 992 | SPh | NHSO$_2$Me | CH$_2$CH$_2$ |
| 993 | Cl | NHSO$_2$Me | CH$_2$CH$_2$ |
| 994 | OH | O | CH$_2$CH$_2$ |
| 995 | SH | O | CH$_2$CH$_2$ |
| 996 | SPh | O | CH$_2$CH$_2$ |
| 997 | Cl | O | CH$_2$CH$_2$ |
| 998 | OH | NH | CH$_2$CH$_2$ |
| 999 | SH | NH | CH$_2$CH$_2$ |
| 1000 | SPh | NH | CH$_2$CH$_2$ |
| 1001 | Cl | NH | CH$_2$CH$_2$ |
| 1002 | OH | SO$_2$ | CH$_2$CH$_2$CH$_2$ |
| 1003 | SH | SO$_2$ | CH$_2$CH$_2$CH$_2$ |
| 1004 | SPh | SO$_2$ | CH$_2$CH$_2$CH$_2$ |
| 1005 | Cl | SO$_2$ | CH$_2$CH$_2$CH$_2$ |
| 1006 | OH | SO | CH$_2$CH$_2$CH$_2$ |
| 1007 | SH | SO | CH$_2$CH$_2$CH$_2$ |
| 1008 | SPh | SO | CH$_2$CH$_2$CH$_2$ |
| 1009 | Cl | SO | CH$_2$CH$_2$CH$_2$ |
| 1010 | OH | S | CH$_2$CH$_2$CH$_2$ |
| 1011 | SH | S | CH$_2$CH$_2$CH$_2$ |
| 1012 | SPh | S | CH$_2$CH$_2$CH$_2$ |
| 1013 | Cl | S | CH$_2$CH$_2$CH$_2$ |
| 1014 | OH | CH$_2$ | CH$_2$CH$_2$CH$_2$ |
| 1015 | SH | CH$_2$ | CH$_2$CH$_2$CH$_2$ |
| 1016 | SPh | CH$_2$ | CH$_2$CH$_2$CH$_2$ |
| 1017 | Cl | CH$_2$ | CH$_2$CH$_2$CH$_2$ |
| 1018 | OH | NHSO$_2$Me | CH$_2$CH$_2$CH$_2$ |
| 1019 | SH | NHSO$_2$Me | CH$_2$CH$_2$CH$_2$ |
| 1020 | SPh | NHSO$_2$Me | CH$_2$CH$_2$CH$_2$ |
| 1021 | Cl | NHSO$_2$Me | CH$_2$CH$_2$CH$_2$ |
| 1022 | OH | O | CH$_2$CH$_2$CH$_2$ |
| 1023 | SH | O | CH$_2$CH$_2$CH$_2$ |
| 1024 | SPh | O | CH$_2$CH$_2$CH$_2$ |
| 1025 | Cl | O | CH$_2$CH$_2$CH$_2$ |
| 1026 | OH | NH | CH$_2$CH$_2$CH$_2$ |
| 1027 | SH | NH | CH$_2$CH$_2$CH$_2$ |
| 1028 | SPh | NH | CH$_2$CH$_2$CH$_2$ |
| 1029 | Cl | NH | CH$_2$CH$_2$CH$_2$ |
| 1030 | OH | SO$_2$ | CH=CH |
| 1031 | SH | SO$_2$ | CH=CH |
| 1032 | SPh | SO$_2$ | CH=CH |
| 1033 | Cl | SO$_2$ | CH=CH |
| 1034 | OH | SO | CH=CH |
| 1035 | SH | SO | CH=CH |
| 1036 | SPh | SO | CH=CH |
| 1037 | Cl | SO | CH=CH |
| 1038 | OH | S | CH=CH |
| 1039 | SH | S | CH=CH |
| 1040 | SPh | S | CH=CH |
| 1041 | Cl | S | CH=CH |
| 1042 | OH | CH$_2$ | CH=CH |
| 1043 | SH | CH$_2$ | CH=CH |
| 1044 | SPh | CH$_2$ | CH=CH |
| 1045 | Cl | CH$_2$ | CH=CH |
| 1046 | OH | NHSO$_2$Me | CH=CH |
| 1047 | SH | NHSO$_2$Me | CH=CH |
| 1048 | SPh | NHSO$_2$Me | CH=CH |
| 1049 | Cl | NHSO$_2$Me | CH=CH |
| 1050 | OH | O | CH=CH |
| 1051 | SH | O | CH=CH |
| 1052 | SPh | O | CH=CH |
| 1053 | Cl | O | CH=CH |
| 1054 | OH | NH | CH=CH |
| 1055 | SH | NH | CH=CH |
| 1056 | SPh | NH | CH=CH |
| 1057 | Cl | NH | CH=CH |

TABLE 10

Compounds of the formula (I) according to the invention in which the substituents and indices are as defined below:

| | | | | | |
|---|---|---|---|---|---|
| A = | SO$_2$ | B = | CH$_2$—CH$_2$ | R$^3$ = | H |
| R$^4$ = | H | Y = | CH$_2$ | Z = | CH$_2$ |
| R$^7$ = | R$^A$, R$^B$, R$^C$, R$^D$ | I = | 1 | v = | 1 |
| Q = | radical of formula (II) | | | | |

TABLE 10-continued

Compounds of the formula (I) according to the invention in which the substituents and indices are as defined below:

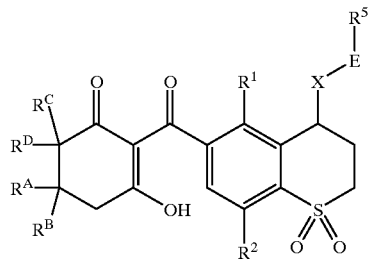

| No. | $R^A, R^B$ | $R^C, R^D$ | $R^1$ | $R^2$ | X | E | $R^5$ | Physical data |
|---|---|---|---|---|---|---|---|---|
| 1058 | H, H | H, H | H | H | S | bond | 2-pyridyl | $^1$H NMR (CDCl$_3$): δ 2.1 (m, 2H), 2.4 (m, 2H), 2.7 (m, 2H), 2.8 (m, 1H), 3.05 (m, 1H), 3.4 (m, 1H), 3.9 (m, 1H), 5.62 (m, 1H), 7.1 (m, 1H), 7.18 (d, 1H), 7.65 (m, 1H), 7.7 (s, 1H), 7.95 (m, 1H), 8.5 (m, 1H) |
| 1059 | H, H | H, H | Me | Me | S | bond | 2-methyl-1,3,4-thiadiazol-5-yl | $^1$H NMR (CDCl$_3$): δ 2.05 (m, 2H), 2.35 (s, 3H), 2.45 (m, 2H), 2.7 (m, 2H), 2.75 (m, 3H), 2.8 (s, 3H), 2.95 (m, 3H), 3.45 (m, 1H), 4.15 (m, 1H), 5.7 (m, 1H), 6.96 (s, 1H) |
| 1060 | H, H | H, H | H | H | S | bond | 2-pyrimidinyl | m.p. 133° C. |
| 1061 | H, H | H, H | Me | Me | O | bond | 3-cyano-2-pyridyl | m.p. 232–238° C. |
| 1062 | Me, Me | H, H | Me | Me | O | bond | 3-cyano-2-pyridyl | m.p. 141–144° C. |
| 1063 | H, H | H, H | Me | Me | O | bond | 3-nitro-phenyl | m.p. 158° C. |
| 1064 | Me, Me | H, H | Me | Me | O | bond | 4,6-dimethoxy-2-pyrimidinyl | m.p. 133–136° C. |
| 1065 | H, H | Me, Me | Me | Me | O | bond | 2-pyrimidinyl | $^1$H NMR (CDCl$_3$): δ 1.3 (m, 2H), 1.9 (m, 2H), 2.05 (s, 3H), 2.38 (s, 3H), 2.8 (m, 4H), 3.2 (m, 1H), 3.9 (m, 1H), 6.45 (m, 1H), 6.98 (s, 1H), 7.05 (m, 1H), 8.6 (m, 1H) |
| 1066 | H, H | H, H | Me | Me | O | bond | Ph | $^1$H NMR (CDCl$_3$): δ 1.95 (s, 3H), 2.1 (m, 2H), 2.6 (m, 4H), 2.7 (s, 3H), 2.7 (m, 2H), 3.15 (m, 1H), 3.5 (m, 1H), 3.65 (s, 2H), 6.1 (m, 1H), 6.98 (s, 1H), 7.3 (m, 5H) |
| 1067 | H, H | H, H | Me | Me | O | bond | 3-fluoro-4-nitro-phenyl | m.p. 236–238° C. |

TABLE 11

Compounds of the formula (I) according to the invention in which the substituents and indices are as defined below:

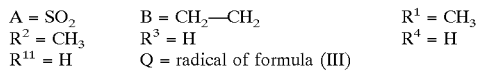

A = SO$_2$   B = CH$_2$—CH$_2$   $R^1$ = CH$_3$
$R^2$ = CH$_3$   $R^3$ = H   $R^4$ = H
$R^{11}$ = H   Q = radical of formula (III)

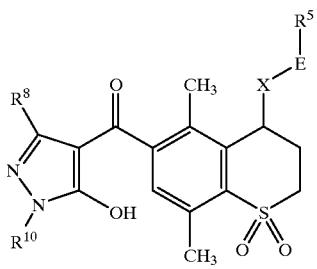

| No. | $R^8$ | $R^{10}$ | X | E | $R^5$ | Physical data |
|---|---|---|---|---|---|---|
| 1068 | Me | Me | O | bond | 3-nitro-6-pyridyl | m.p. 149° C. |
| 1069 | Me | Me | O | bond | 3-fluoro-4-nitro-phenyl | m.p. 159° C. |
| 1070 | Me | Me | O | bond | 2-nitrophenyl | m.p. 165° C. |
| 1071 | Me | Me | S | bond | 2-pyrimidinyl | $^1$H NMR(CDCl$_3$): δ1.75 (s, 3H), 2.1(s, 3H), 2.8(s, 3H), 2.8(m, 1H), 2.95(m, 1H), 3.4(m, 1H), 3.65(s, 3H), 4.2(m, 1H), 5.45(m, 1H), 7.1(t, 1H), 7.25 (2, 1H), 8.6(d, 2H) |
| 1072 | Me | Me | O | bond | 2-pyrimidinyl | $^1$H NMR(CDCl$_3$): δ1.75 (s, 3H), 2.12(s, 3H), 2.8 |

TABLE 11-continued

Compounds of the formula (I) according to the invention in which the substituents and indices are as defined below:

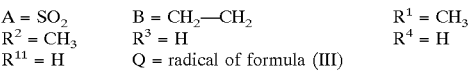

A = SO$_2$   B = CH$_2$—CH$_2$   $R^1$ = CH$_3$
$R^2$ = CH$_3$   $R^3$ = H   $R^4$ = H
$R^{11}$ = H   Q = radical of formula (III)

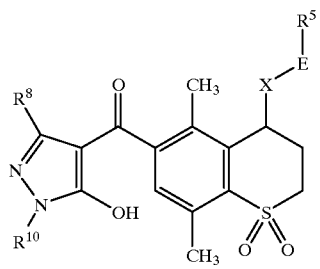

| No. | $R^8$ | $R^{10}$ | X | E | $R^5$ | Physical data |
|---|---|---|---|---|---|---|
| | | | | | | (s, 3H), 2.82(m, 2H), 3.3 (m, 1H), 3.95(m, 1H), 6.45(m, 1H), 7.05(t, 1H), 7.22(s, 1H), 7.32(s, 1H), 8.6(d, 2H) |
| 1073 | Me | Me | O | bond | 4,6-dimethyl-2-pyrimidinyl | $^1$H NMR(CDCl$_3$): δ1.75 (s, 3H), 2.12(s, 3H), 2.45 (s, 6H), 2.8(s, 3H), 2.82 (m, 2H), 3.25(m, 1H), 3.98(m, 1H), 6.45(m, 1H), 6.78(s, 1H), 7.2(s, 1H), 7.45(s, 1H) |
| 1074 | H | Et | O | bond | 1,4-diazinyl | $^1$H NMR(CDCl$_3$): δ1.45 (t, 3H), 2.2(s, 3H), 2.85 |

TABLE 11-continued

Compounds of the formula (I) according to the invention in which the substituents and indices are as defined below:

| A = SO$_2$ | B = CH$_2$—CH$_2$ | R$^1$ = CH$_3$ |
|---|---|---|
| R$^2$ = CH$_3$ | R$^3$ = H | R$^4$ = H |
| R$^{11}$ = H | Q = radical of formula (III) | |

| No. | R$^8$ | R$^{10}$ | X | E | R$^5$ | Physical data |
|---|---|---|---|---|---|---|
| 1075 | H | Ethyl | O | bond | 2-pyrimidinyl | $^1$H NMR(CDCl$_3$): δ1.45 (t, 3H), 2.25(s, 3H), 2.82 (s, 3H), 2.85(m, 2H), 3.25(m, 1H), 3.95(m, 1H), 4.05(quartett, 2H), 6.45(m, 1H), 7.05(m, 1H), 7.35(s, 1H), 7.38(s, 1H), 8.6(m, 2H) |

(preceding entry physical data: (s, 3H), 2.85(m, 2H), 3.3 (m, 1H), 3.85(m, 1H), 4.05(quartett, 2H), 6.5 (m, 1H), 7.35(s, 1H), 7.4 (s, 1H), 8.15(m, 1H), 8.25(m, 2H))

TABLE 12

Compounds of the formula (I) according to the invention in which the substituents and indices are as defined below:

| A = SO$_2$ | B = CH$_2$—CH$_2$ | E = bond |
|---|---|---|
| R$^1$ = CH$_3$ | R$^2$ = CH$_3$ | R$^3$ = H |
| R$^4$ = H | R$^6$ = OH | Y = CH$_2$ |
| Z = CH$_2$ | Q = radical of formula (II) | I = 0 |
| v = 1 | w = 0 | |

| No. | R$^5$ | Physical data |
|---|---|---|
| 1076 | 1-pyrazolyl | m.p. 213–218° C. |
| 1077 | 1,2,3-triazol-2-yl | $^1$H NMR(CDCl$_3$): δ1.8(s, 3H), 2.05(m, 2H), 2.42(m, 2H), 2.78(m, 3H), 2.8(s, 3H), 3.08 (m, 1H), 3.2(m, 1H), 3.6(m, 1H), 6.15(m, 1H), 7.02(s, 1H), 7.65(s, 2H) |
| 1078 | 1,2,3-triazol-1-yl | |
| 1079 | 3-methyl-pyrazol-1-yl | |
| 1080 | 1,2,4-triazol-1-yl | |
| 1081 | 3-trifluoromethyl-pyrazol-1-yl | R$_f$ = 0.33(SiO$_2$; ethyl acetate) |
| 1082 | 3,5-dimethyl-pyrazol-1-yl | m.p. 176–181° C. |

TABLE 12-continued

Compounds of the formula (I) according to the invention in which the substituents and indices are as defined below:

A = SO₂         B = CH₂—CH₂           E = bond
R¹ = CH₃        R² = CH₃              R³ = H
R⁴ = H          R⁶ = OH               Y = CH₂
Z = CH₂         Q = radical of formula (II)   I = 0
v = 1           w = 0

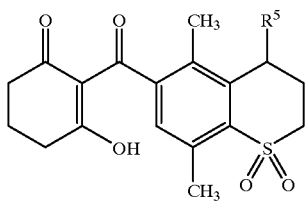

| No. | R⁵ | Physical data |
|---|---|---|
| 1083 | 4-methyl-pyrazol-1-yl | m.p. 138–142° C. |
| 1084 | 4-brom-pyrazol-1-yl | R_f = 0.26(SiO₂; ethyl acetate) |
| 1085 | 1-pyrrolyl | |
| 1086 | 1-imidazolyl | |
| 1087 | 2-nitro-imidazol-1-yl | |
| 1088 | 4-nitro-imidazol-1-yl | m.p. 162–172° C. |
| 1089 | 2-cyano-pyrrol-1-yl | |
| 1090 | 2-methyl-4-nitro-imidazol-1-yl | |
| 1091 | O—N=cyclopentylidene | ¹H NMR(CDCl₃): δ1.75(m, 4H), 2.05(m, 2H), 2.4(m, 5H), 2.65(m, 2H), 2.75(s, 3H), 2.8 (m, 3H), 3.2(m, 1H), 3.75(m, 1H), 5.3(m, 1H), 6.95(s, 1H) |
| 1092 | O—N=cyclohexylidene | R_f = 0.31(SiO₂; ethyl acetate) |
| 1093 | O—N=CHCH₃ | R_f = 0.25/0.33(Cis/trans); (SiO₂; ethyl acetate) |
| 1094 | O—N=C(CH₃)₂ | R_f = 0.36(SiO₂; ethyl acetate) |
| 1095 | O—N=C(CH₃)CH₂CH₃ | R_f = 0.39(SiO₂; ethyl acetate) |
| 1096 | P(O)(OEt)₂ | ¹H NMR(CDCl₃): δ1.2(t, 3H), 1.3(t, 3H), 2.03 (m, 2H), 2.35(s, 3H), 2.42(m, 2H), 2.75(s, 3H), 2.75(m, 4H), 3.38(m, 1H), 3.8–4.25(m, 6H), 6.9 (s, 1H) |
| 1097 | P(O)(OMe)₂ | |
| 1098 | P(O)(O-i-Pr)₂ | |
| 1099 | P(O)(O-c-Pr)₂ | |
| 1100 | OH | ¹H NMR(CDCl₃): δ2.05(m, 2H), 2.25(s, 3H), 2.3(m, 2H), 2.55(m, 2H), 2.65(s, 3H), 2.65 (m, 2H), 3.2(m, 1H), 3.85(m, 1H), 5.0(m, 1H), 6.9(s, 1H) |

TABLE 13

Compounds of the formula (I) according to the invention in which the substituents and indices are as defined below:

A = SO$_2$  B = CH$_2$—CH$_2$  R$^1$ = CH$_3$
R$^2$ = CH$_3$  R$^3$ = H  R$^4$ = H
Q = Radical of formula (III) wherein G$^1$–G$^2$ is OCR$^9$
R$^4$ = c-Pr

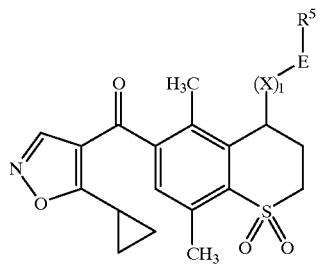

| Nr. | I | x | E | R$^5$ | Physical data |
|---|---|---|---|---|---|
| 1101 | 1 | 0 | bond | 1,4-diazinyl | $^1$H NMR(CDCl$_3$): δ1.2–1.4(m, 4H), 2.18(s, 3H), 2.61(m, 1H), 2.81(s, 3H), 2.85(m, 2H), 3.35(m, 1H), 3.85 (m, 1H), 6.52(m, 1H), 7.35(s, 1H), 8.18 (m, 2H), 8.25(m, 2H) |
| 1102 | 1 | 0 | bond | 4,6-dimethoxy-2-pyrimidinyl | $^1$H NMR(CDCl$_3$): δ1.2–1.4(m, 4H), 2.25(s, 3H), 2.45(m, 1H), 2.8(s, 3H), 2.8(m, 1H), 2.8–3.2(m, 2H), 3.3 (m, 1H), 3.95(m, 1H), 3.95(s, 6H), 6.4 (m, 1H), 7.3(s, 1H), 8.2(s, 1H) |
| 1103 | 1 | 0 | bond | 2-pyrimidinyl | |
| 1104 | 0 | | bond | 1-pyrazolyl | |
| 1105 | 0 | | bond | 1,2,3-triazol-2-yl | |

TABLE 14

Compounds of the formula (I) according to the invention in which the substituents and indices are as defined below:

A = SO$_2$  B = CH$_2$—CH$_2$  R$^1$ = CH$_3$
R$^2$ = CH$_3$  R$^3$ = H  R$^4$ = H
Q = radical of formula (IV)  R$^5$ = c-Pr

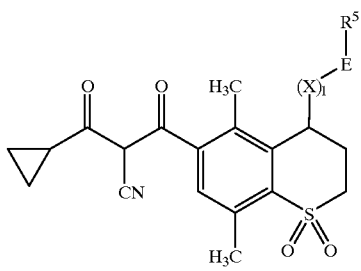

| Nr. | I | x | E | R$^5$ | Physical data |
|---|---|---|---|---|---|
| 1106 | 1 | 0 | bond | 1,4-diazinyl | $^1$H NMR(CDCl$_3$): δ1.3(m, 2H), 1.42(m, 2H), 2.22(s, 3H), 2.38 (m, 1H), 2.82(m, 3H), 3.3(m, 1H), 3.8(m, 1H), 6.5(m, 1H), 7.42(s, 1H), 8.2(m, 1H), 8.25(m, 2H), 8.25(s, 1H) |
| 1107 | 1 | 0 | bond | 2-pyrimidinyl | |
| 1108 | 0 | | bond | 1-pyrazolyl | |

TABLE 15

Compounds of the formula (I) according to the invention in which the substituents and indices are as defined below:

A = SO$_2$  B = CH$_2$—CH$_2$  E = bond
R$^1$ = CH$_3$  R$^2$ = CH$_3$  R$^3$ = H
R$^4$ = H  R$^6$ = OH  Y = CH$_2$
Z = CH$_2$  Q = radical of formula (II)  I = 0
v = 1  w = 0

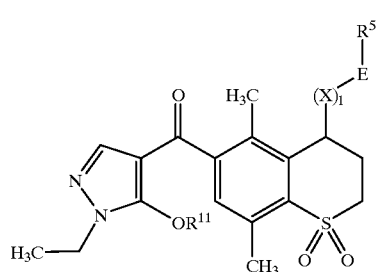

| Nr. | I | x | E | R$^5$ | R$^{11}$ |
|---|---|---|---|---|---|
| 1109 | 1 | 0 | bond | 1,4-diazinyl | Bz |
| 1110 | 1 | 0 | bond | 1,4-diazinyl | 4-Me—PhC(O) |
| 1111 | 1 | 0 | bond | 1,4-diazinyl | MeSO$_2$ |
| 1112 | 1 | 0 | bond | 1,4-diazinyl | EtSO$_2$ |
| 1113 | 1 | 0 | bond | 1,4-diazinyl | PrSO$_2$ |
| 1114 | 1 | 0 | bond | 1,4-diazinyl | PhSO$_2$ |
| 1115 | 1 | 0 | bond | 1,4-diazinyl | 4-Me—PhSO$_2$ |
| 1116 | 1 | 0 | bond | 2-pyrimidinyl | Bz |
| 1117 | 1 | 0 | bond | 2-pyrimidinyl | 4-Me—PhC(O) |
| 1118 | 1 | 0 | bond | 2-pyrimidinyl | MeSO$_2$ |

TABLE 15-continued

Compounds of the formula (I) according to the invention in which the substituents and indices are as defined below:

A = SO₂          B = CH₂—CH₂       E = bond
R¹ = CH₃        R² = CH₃           R³ = H
R⁴ = H          R⁶ = OH            Y = CH₂
Z = CH₂         Q = radical of formula (II)   I = 0
v = 1           w = 0

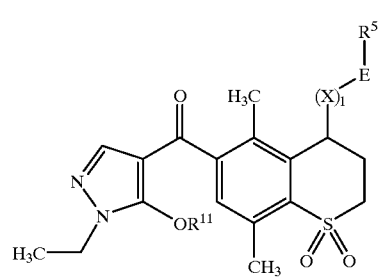

| Nr. | I | x | E | R⁵ | R¹¹ |
|---|---|---|---|---|---|
| 1119 | 1 | 0 | bond | 2-pyrimidinyl | EtSO₂ |
| 1120 | 1 | 0 | bond | 2-pyrimidinyl | PrSO₂ |
| 1121 | 1 | 0 | bond | 2-pyrimidinyl | PhSO₂ |
| 1122 | 1 | 0 | bond | 2-pyrimidinyl | 4-Me—PhSO₂ |
| 1123 |   | 0 | bond | 1-pyrazolyl | Bz |
| 1124 |   | 0 | bond | 1-pyrazolyl | 4-Me—PhC(O) |
| 1125 |   | 0 | bond | 1-pyrazolyl | MeSO₂ |
| 1126 |   | 0 | bond | 1-pyrazolyl | EtSO₂ |
| 1127 |   | 0 | bond | 1-pyrazolyl | PrSO₂ |
| 1128 |   | 0 | bond | 1-pyrazolyl | PhSO₂ |
| 1129 |   | 0 | bond | 1-pyrazolyl | 4-Me—PhSO₂ |

TABLE 16

Compounds of the formula (I) according to the invention in which the substituents and indices are as defined below:

A = SO₂              B = CH₂—CH₂        R¹ = CH₃
R² = CH₃             R³ = H              R⁴ = H
R⁷ = H               Y = CH₂             Z = CH₂
Q = radical of formula (II)              v = 1

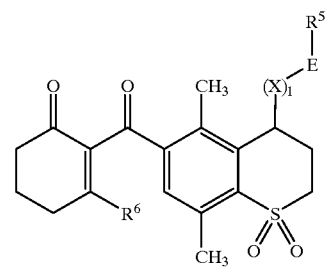

| Nr. | I | x | E | R⁵ | R⁶ |
|---|---|---|---|---|---|
| 1130 | 1 | 0 | bond | 1,4-diazinyl | MeS |
| 1131 | 1 | 0 | bond | 1,4-diazinyl | EtS |
| 1132 | 1 | 0 | bond | 1,4-diazinyl | PrS |
| 1133 | 1 | 0 | bond | 1,4-diazinyl | MeSO₂ |
| 1134 | 1 | 0 | bond | 1,4-diazinyl | EtSO₂ |
| 1135 | 1 | 0 | bond | 2-pyrimidinyl | MeS |
| 1136 | 1 | 0 | bond | 2-pyrimidinyl | EtS |
| 1137 | 1 | 0 | bond | 2-pyrimidinyl | PrS |
| 1138 | 1 | 0 | bond | 2-pyrimidinyl | MeSO₂ |
| 1139 | 1 | 0 | bond | 2-pyrimidinyl | EtSO₂ |
| 1140 |   | 0 | bond | 1-pyrazolyl | MeS |
| 1141 |   | 0 | bond | 1-pyrazolyl | EtS |
| 1142 |   | 0 | bond | 1-pyrazolyl | PrS |
| 1143 |   | 0 | bond | 1-pyrazolyl | MeSO₂ |
| 1144 |   | 0 | bond | 1-pyrazolyl | EtSO₂ |

TABLE 17

Compounds of the formula (I) according to the invention in which the substituents and indices are as defined below:

A = SO$_2$    B = CH$_2$    R$^3$ = H
R$^4$ = H    R$^6$ = OH    Y = CH$_2$
Z = CH$_2$    v = 1    w = 0
Q = radical of formula (II)

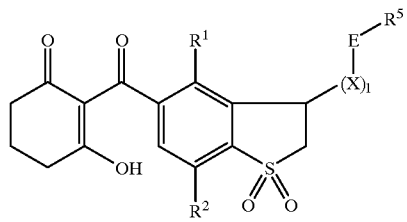

| No. | R$^1$ | R$^2$ | l | x | E | R$^5$ | Physical data |
|---|---|---|---|---|---|---|---|
| 1145 | Me | Me | 0 |   | bond | 1-pyrazolyl | $^1$H NMR(CDCl$_3$): δ1.9(m, 3H), 2.05 (m, 2H), 2.42(m, 2H), 2.65(s, 3H), 2.8(m, 2H), 3.65(m, 1H), 3.98 (m, 1H), 6.25(m, 1H), 6.28(m, 1H), 7.1(s, 1H), 7.2(m, 1H), 7.59(m, 1H) |
| 1146 | Me | Me | 0 |   | bond | 1,2,3-pyrazol-1-yl |   |
| 1147 | Me | Me | 1 | O | bond | Ph | $^1$H NMR(CDCl$_3$): δ2.05(m, 2H), 2.18(s, 3H), 2.42(m, 2H), 2.6 (m, 2H), 2.8(m, 2H), 3.65(m, 2H), 4.58(s, 2H), 5.38(m, 1H), 7.01 (s, 1H), 7.35(m, 5H) |
| 1148 | Me | Me | 1 | O | bond | 2-pyrimidinyl |   |
| 1149 | Me | Me | 1 | O | bond | 1,4-diazinyl |   |
| 1150 | Me | Me | 1 | O | bond | 3-cyano-2-pyridyl |   |
| 1151 | Me | H | 0 |   | bond | 1-pyrazolyl |   |
| 1152 | Me | H | 0 |   | bond | 1,2,4-pyrazol-1-yl |   |
| 1153 | Me | H | 1 | O | bond | Ph |   |
| 1154 | Me | H | 1 | O | bond | 2-pyrimidinyl |   |
| 1155 | Me | H | 1 | O | bond | 1,4-diazinyl |   |
| 1156 | Me | H | 1 | O | bond | 3-cyano-2-pyridyl |   |
| 1157 | Me | Cl | 0 |   | bond | 1-pyrazolyl |   |
| 1158 | Me | Cl | 0 |   | bond | 1,2,4-pyrazol-1-yl |   |
| 1159 | Me | Cl | 1 | O | bond | Ph |   |
| 1160 | Me | Cl | 1 | O | bond | 2-pyrimidinyl |   |
| 1161 | Me | Cl | 1 | O | bond | 1,4-diazinyl |   |
| 1162 | Me | Cl | 1 | O | bond | 3-cyano-2-pyridyl |   |
| 1163 | Cl | Cl | 0 |   | bond | 1-pyrazolyl |   |
| 1164 | Cl | Cl | 0 |   | bond | 1,2,4-pyrazol-1-yl |   |
| 1165 | Cl | Cl | 1 | O | bond | Ph |   |
| 1166 | Cl | Cl | 1 | O | bond | 2-pyrimidinyl |   |
| 1167 | Cl | Cl | 1 | O | bond | 1,4-diazinyl |   |
| 1168 | Cl | Cl | 1 | O | bond | 3-cyano-2-pyridyl |   |
| 1169 | Cl | H | 0 |   | bond | 1-pyrazolyl |   |
| 1170 | Cl | H | 0 |   | bond | 1,2,4-pyrazol-1-yl |   |
| 1171 | Cl | H | 1 | O | bond | Ph |   |
| 1172 | Cl | H | 1 | O | bond | 2-pyrimidinyl |   |
| 1173 | Cl | H | 1 | O | bond | 1,4-diazinyl |   |
| 1174 | Cl | H | 1 | O | bond | 3-cyano-2-pyridyl |   |

FORMULATION EXAMPLES

1. Dusting Agent

A dusting agent is obtained by mixing 10 parts by weight of a compound of the formula (I) and 90 parts by weight of talc as inert substance and comminuting the mixture in a hammer mill.

2. Dispersible Powder

A wettable powder which is readily dispersible in water is obtained by mixing 25 parts by weight of the compound of the formula (1), 64 parts by weight of kaolin-containing quartz as inert substance, 10 parts by weight of potassium lignosulfonate and 1 part by weight of sodium oleoylmethyltaurinate as wetting agent and dispersant and grinding the mixture in a pinned-disk mill.

3. Dispersion Concentrate

A dispersion concentrate which is readily dispersible in water is obtained by mixing 20 parts by weight of a compound of the formula (I), 6 parts by weight of alkylphenol polyglycol ether (®Triton X 207), 3 parts by weight of isotridecanol polyglycol ether (8 EO) and 71 parts by weight of paraffinic mineral oil (boiling range, for example, approx. 255 to above 277° C.) and grinding the mixture in a ball mill to a fineness of below 5 microns.

4. Emulsifiable Concentrate

An emulsifiable concentrate is obtained from 15 parts by weight of a compound of the formula (I), 75 parts by weight of cyclohexanone as solvent and 10 parts by weight of ethoxylated nonylphenol as emulsifier.

5. Water-dispersible Granules

Water-dispersible granules are obtained by mixing 75 parts by weight of a compound of the formula (I),
10 parts by weight of calcium lignosulfonate,
5 parts by weight of sodium lauryl sulfate,
3 parts by weight of polyvinyl alcohol and
7 parts by weight of kaolin,
grinding the mixture in a pinned-disk mill and granulating the powder in a fluidized bed by spraying on water as granulation liquid.

Water-dispersible granules are also obtained by homogenizing and precomminuting, on a colloid mill,
25 parts by weight of a compound of the formula (I),
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water, subsequently grinding the mixture in a bead mill and atomizing and drying the resulting suspension in a spray tower by means of a single-substance nozzle.

C. BIOLOGICAL EXAMPLES

1. Pre-emergence Effect on Weeds

Seeds of mono- and dicotyledonous weed plants are placed in sandy loam soil in cardboard pots and covered with the soil. The compounds according to the invention which were formulated in the form of wettable powders or emulsion concentrates are then applied to the surface of the cover soil in the form of aqueous suspensions or emulsions at an application rate of 600 to 800 l of water/ha (converted), at a dosage of 1 kg of active substance or less per hectare. After the treatment, the pots are placed in a greenhouse and kept under good growth conditions for the weeds. After the test plants have emerged, the damage to the plants or the negative effects on the emergence was scored visually after a test period of 3 to 4 weeks by comparison with untreated controls. Here, the compounds of Example Nos. 7 and 11, for example, show at least 80% activity against Stellaria media, Avena fatua, Lolium multiflorum and Setaria viridis. The compounds of Example Nos. 2, 3, 4, 7, 11 and 12 show at least 90% activity against Amaranthus retroflexus, Sinapis arvensis and Setaria viridis. The compounds of Example Nos. 1, 2, 6, 7 a [lacuna] show 100% activity against Amaranthus retroflexus and Stellaria media.

2. Post-emergence Effect on Weeds

Seeds of mono- and dicotyledonous weeds are placed in sandy loam soil in cardboard pots, covered with soil and grown in a greenhouse under good growth conditions. Two to three weeks after sowing, the test plants are treated at the three-leaf stage. The compounds according to the invention which were formulated as wettable powders or emulsion concentrates are sprayed at a dosage of 1 kg of active substance or less per hectare (converted) onto the green parts of the plants at an application rate of 600 to 800 l of water/ha (converted). After the test plants had remained in the greenhouse for 3 to 4 weeks under ideal growth conditions, the effect of the preparations is scored by comparison with untreated controls. The agents according to the invention also have good herbicidal activity post-emergence against a broad spectrum of economically important weed grasses and broad-leaved weeds. The compounds of Example Nos. 3, 9, 10, 11 and 12, for example, have at least 90% activity against Sinapis arvensis. The compounds of Example Nos. 1, 4, 7 and 10 show at least 80% activity against Stellaria media and Setaria viridis. The compounds of Example Nos. 6 and 9 show at least 80% activity against Avena fatua and Amaranthus retroflexus.

3. Effect on Harmful Plants in Rice

Typical harmful plants in rice crops are grown in a greenhouse under paddy rice conditions (dammed height of water: 2–3 cm). After the treatment with the formulated compounds according to the invention at a dosage of 1 kg of active substance or less per hectare (converted), the test plants are set up in the greenhouse under optimum growth conditions and are maintained in this way throughout the entire test period. About three weeks after the application, evaluation is carried out by visual scoring of the damage to the plants by comparison with untreated controls. The compounds according to the invention show very good herbicidal activity against harmful plants. The compounds of Example Nos. 2, 4, 7, 11 and 12, for example, show at least 80% activity against Cyperus iria and Echinocloa crus-galli.

4. Tolerance by Crop Plants

In further greenhouse experiments, seeds of a relatively large number of crop plants and weeds are placed in sandy loam soil and covered with soil. Some of the pots are treated immediately as described under Section 1, while the remainder are placed in a greenhouse until the plants have developed two to three leaves, and then sprayed with various dosages of the substance of the formula (I) according to the invention, as described in Section 2. Four to five weeks after the application, and after the plants have remained in the greenhouse, visual scoring shows that the compounds according to the invention generally leave dicotyledonous crops such as, for example, soya and sugarbeet undamaged, or virtually undamaged, when employed pre- and post-emergence, even when high dosages of active compound are used. Moreover, some substances also leave gramineous crops unharmed, for example barley, wheat and rice. Some of the compounds of the formula (I) display a high selectivity and are therefore suitable for controlling undesirable plant growth in agricultural crops.

What is claimed is:

1. A compound of the formula (I)

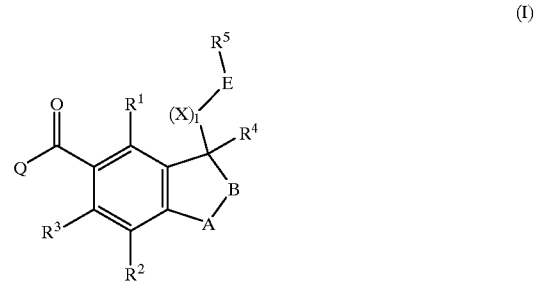

in which

Q is a radical of the formula (II), (III) or (IV)

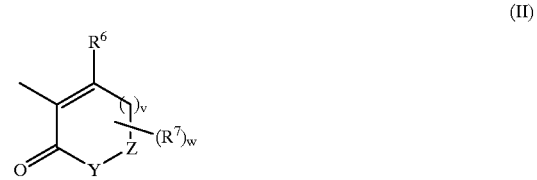

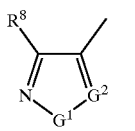

(III)

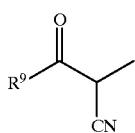

(IV)

$R^1$, $R^2$, $R^3$ independently of one another are hydrogen, hydroxyl, thio, amino, cyano, nitro, halogen or an unsubstituted or substituted hydrocarbon radical which may or may not contain one or more additional, identical or different, heteroatoms selected from the group consisting of oxygen, sulfur, nitrogen, fluorine, chlorine, bromine and iodine;

$R^4$ is hydrogen, cyano, alkyl, alkenyl, alkynyl, cycloalkyl, alkoxylcarbonyl, phenyl, where the six last-mentioned groups are unsubstituted or substituted by one or more identical or different radicals selected from the group consisting of halogen, nitro, cyano, alkyl, cycloalkyl, alkenyl, alkynyl, alkoxy and alkylthio;

$R^5$ is heteroaryl, heterocyclyl or aryl which is unsubstituted or mono- or polysubstituted by identical or different radicals, or is a radical selected from the group consisting of $-O-N=CR^lR^m$, $-P(=O)(OR^i)(R^j)$, $-P(=O)(OR^j)(OR^k)$ or

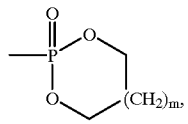

or, if E is a bond and l is zero and Q is other than a radical formula II where $G^1-G^2$ is $NR^\circ COR''$, then $R^5$ is also hydroxyl, A is a divalent unit selected from the group consisting of O, S, SO, and $SO_2$;

B is a chain which has two carbon atoms, which is saturated or contains one or more multiple bonds and which is unsubstituted or substituted by alkyl, haloalkyl, alkoxy, haloalkoxy or by an unsubstituted or alkyl-, haloalkyl-, alkoxy-, haloalkoxy-, halogen-, cyano- or nitro-substituted phenyl radical;

E is a bond, a one- to six-membered chain which is saturated or contains one or more multiple bonds and which consists of divalent units selected from the group consisting of C, $CR^c$, $CR^cR^d$, N, $NR^c$, S, SO, $SO_2$, O and CO;

X is a divalent unit selected from the group consisting of O, S and $NR^e$;

$R^6$ is alklylthio, haloalkylthio, alkylsulfinyl, haloalkylsulfinyl, alkylsulfonyl, haloalkylsulfonyl, cyano, cyanato, thiocyanato, halogen or $OR^f$;

Y is a divalent unit selected from the group consisting of O, S, NH, N-alkyl or $CHR^7$;

$R^7$ is hydrogen, tetrahydropyran-3-yl, tetrahydropyran-4-yl, tetrahydrothiopyran-3-yl, alkyl, cycloalkyl, alkoxy, alkoxyalkyl, alkylcarbonyl, alkoxycarbonyl, alkylthio, phenyl, where the hydrocarbon moiety of the eight last-mentioned radicals is unsubstituted or substituted by one or more identical or different radicals selected from the group consisting of halogen, alkylthio and alkyloxy, or two radicals $R^7$ which are attached to a joint carbon atom form a chain selected from the group consisting of $OCH_2CH_2O$, $OCH_2CH_2CH_2O$, $SCH_2CH_2S$ and $SCH_2CH_2CH_2S$, this chain being unsubstiuted or substituted by one to four methyl groups, or two radicals $R^7$ which are attached to directly adjacent carbon atoms form a bond or together with the carbon atoms that carry them form an unsubstituted or substituted 3- to 6-membered ring;

Z is a bond, a divalent unit selected from the group consisting of O, S, SO, $SO_2$, NH, N-alkyl or $CHR^7$, where Y and Z shoul not simultaneously be a divalent unit which contains an oxygen, nitrogen or sulfur atom as chain member;

$G^1-G^2$ is a divalent unit selected from the group consisting of $OCR^9$, $SCR^9$ and $NR^{10}COR^{11}$, where the attachment to the ring system is to be carried out such that the carbon atom of this divalent unit is in each case attached to the carbon atom of the ring system via a double bond;

$R^8$ is hydrogen, alkyl or alkoxycarbonyl;

$R^9$ is hydrogen, alkyl, cycloalkyl, haloalkyl or halocycloalkyl;

$R^{10}$ is hydrogen, alkyl, alkenyl, alkynyl, cycloalkyl, phenyl, benzyl, where the six last-mentioned groups are unsubstituted or substituted by one or more identical or different radicals selected from the group consisting of halogen, cyano, nitro and alkoxy;

$R^{11}$ is hydrogen, formyl, alkyl, haloalkyl, alkoxyalkyl or a group $L-R^{12}$;

L is a divalent unit selected from the group consisting of $SO_2$, CO, $CHR^gCO$ or $CR^gR^h$;

$R^{12}$ is alkyl, haloalkyl, alkoxy, haloalkoxy, alkylamino, dialkylamino, cycloalkyl or is phenyl which is unsubstituted or substituted by one or more identical or different radicals selected from the group consisting of cyano, nitro, alkyl, alkoxy, haloalkyl and haloalkoxy;

$R^c$ and $R^d$ independently of one another are hydrogen, halogen, nitro, cyano, alkyl, haloalkyl, cycloalkyl, alkenyl, haloalkenyl, alkynyl, haloalkynyl, alkoxy, haloalkoxy, alkylthio, haloalkylthio, alkylcarbonyl, haloalkylcarbonyl, alkoxycarbonyl, haloalkoxycarbonyl, aminocarbonyl, alkylaminocarbonyl, dialkylaminocarbonyl, haloalkylcarbonylamino, alkylcarbonyl-N-alkylamino, alkylsulfonyl, alkylsulfinyl, alkylsulfonylamino, haloalkylsulfonyl, haloalkylsulfinyl, alkylsulfonylamino and alkylsulfonyl-N-alkylamino;

$R^e$ is hydrogen, formyl, alkyl, cycloalkyl, alkenyl, alkynyl, alkylcarbonyl and alkylsulfonyl, where the hydrocarbon moiety of the six last-mentioned radicals may be unsubstituted or substituted by one or more identical or different radicals selected from the group consisting of halogen, nitro, cyano, alkyl, cycloalkyl, alkenyl, alkynyl, alkoxy and alkylthio;

$R^f$ is hydrogen, alkyl, haloalkyl, alkoxyalkyl, formyl, alkylcarbonyl, alkoxycarbonyl, alkylaminocarbonyl, dialkylaminocarbonyl, alkylsulfonyl, haloalkylsulfonyl, benzoyl or phenylsulfonyl, where the aromatic moiety of the two last-mentioned radicals is unsubstituted or substituted by one or more identical or different radicals selected from the group consisting of alkyl, haloalkyl, alkoxy, haloalkoxy, halogen, cyano and nitro;

$R^g$ and $R^h$ independently of one another are hydrogen or alkyl;

$R^i$ and $R^k$ independently of one another are hydrogen or $R^j$;

$R^j$ is alkyl, alkenyl, haloalkyl, haloalkenyl, phenyl, benzyl, where these six abovementioned radicals are unsubstittded or substituted by one or more identical or different radicals selected from the group consisting of halogen, cyano, nitro, $(C_1–C_4)$-alkyl, $(C_1–C_4)$-alkoxy, halogen-$(C_1–C_4)$-alkyl or halo-$(C_1–C_4)$-alkoxy;

$R^l$ and $R^m$ independently of one another are hydrogen or alkyl, alkenyl, alkynyl, haloalkyl, haloalkenyl or haloalkynyl which is substituted by one or more identical or different radicals $R^1$, or $R^l$ and $R^m$ together with the carbon atom to which they are attached form a 3-, 4-, 5-, 6-, 7- or 8-membered saturated or partially unsaturated ring which may or may not contain one to three heteroatoms selected from the group consisting of oxygen, sulfur and nitrogen and which is unsubstituted or substituted by one or more identical or different radicals $R^1$;

$R^{10}$ is hydrogen, alkyl, alkenyl, alkynyl, cycloalkyl, phenyl, benzyl, where the six last-mentioned groups are unsubstituted or substituted by one or more identical or different radicals selected from the group consisting of halogen, cyano, nitro and alkoxy;

$R^{11}$ is hydrogen, formyl, alkyl, haloalkyl, alkoxyalkyl or a group L-$R^{12}$;

L is a divalent unit selected from the group consisting of $SO_2$, CO, $CHR^gCO$ or $CR^gR^h$;

$R^{12}$ is alkyl, haloalkyl, alkoxy, haloalkoxy, alkylamino, dialkylamino, cycloalkyl or is phenyl which is unsubstituted or substituted by one or more identical or different radicals selected from the group consisting of cyano, nitro, alkyl, alkoxy, haloalkyl and haloalkoxy;

$R^c$ and $R^d$ independently of one another are hydrogen, halogen, nitro, cyano, alkyl, haloalkyl, cycloalkyl, alkenyl, haloalkenyl, alkynyl, haloalkynyl, alkoxy, haloalkoxy, alkylthio, haloalkylthio, alkylcardonyl, haloalkylcarbonyl, alkoxycarbonyl, haloalkoxycarbonyl, aminocarbonyl, alkylaminocarbonyl, dialkylaminocarbonyl, haloalkylcarbonylamino, alkylcarbonyl-N-alkylamino, alkylsulfonyl, alkylsulfinyl, alkylsulfonylamino, haloalkylsulfonyl, haloalkylsulfinyl, alkylsulfonylamino and alkylsulfonyl-N-alkylamino;

l is 0 or 1;

m is 0, 1 or 2;

n is 0, 1, 2 or 3;

v is 1 or 2;

w is 0, 1, 2, 3 or 4, with the proviso that d) the compound 4-[2-tetrahydrofuryl]methyloxy-5,8-dimethyl-6-[(2,6-dioxocyclohexyl)carbonyl]-1,2,3,4-tetrahydro-1$\lambda^6$-thiochromene-1,1-dione is not embraced by the above definition and e) in $R^5$ aryl is not phenyl if E is methylene and $G^1$ in $G^1$–$G^2$ is sulfur.

2. The compound as claimed in claim 1 in which $R^1$, $R^2$, $R^3$ independently of one another are hydrogen, alkyl, alkenyl, alkynyl, cycloalkyl, cycloalkenyl, cycloalkylalkyl, cycloalkyalkenyl, cycloalkylalkynyl, aryl, arylalkyl, arylalkenyl, arylalkynyl, heteroaryl, heteroarylalkyl, heteroarylalkenyl, heteroarylalkynyl, heterocyclyl, heterocyclylalkyl, heterocyclylalkenyl, heterocyclylalkynyl, hydroxyl, alkoxy, alkenyloxy, alkynyloxy, cycloalkoxy, cycloalkylalkoxy, cycloalkylalkenyloxy, cycloalkylalkynyloxy, cycloalkenyloxy, aryloxy, arylalkoxy, arylalkenyloxy, arylalkynyloxy, heterroaryloxy, heteroarylalkoxy, heteroarylalkenyloxy, heteroarylalkynyloxy, heterocyclyloxy, heterocyclylalkoxy, heterocyclylalkenyloxy, heterocyclylalkynyloxy, thio, alkylthio, alkenylthio, alkynylthio, cycloalkylthio, cycloalkylalkylthio, cycloalkylalkenylthio, cycloalkylalkylthio, cycloalkenylthio, arylthio, arylalkylthio, arylalkenylthio, arylalkynylthio, heteroarylthio, heteroarylalkylthio, heteroarylalkenylthio, heteroarylalkynylthio, heterocyclylthio, heterocyclylalkylthio, heterocyclylalkenylthio, heterocyclylalkynylthio, amino, unsubstituted or substituted mono- or dialkylamino, unsubstituted or substituted mono- or diarylamino, unsubstituted or substituted mono- or diheteroarylamino, unsubstituted or substituted N-alkyl-N-arylamino, unsubsfituted or substituted N-alkyl-N-heteroarylamino, alkenylamino, alkynylamino, cycloalkylamino, cycloalkenylamino, heterocyclylalkylamino, heterocyclyl-alkenylamino, alkylsulfonyl, alkenylsulfonyl, alkynylsulfonyl, cycloalkylsulfonyl, cycloalkylalkylsulfonyl, cycloalkylalkenylsulfonyl, cycloalkylalkynylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynyl-sulfonyl, heterocyclylsulfonyl, heterocyclylalkylsulfonyl, heterocyclylalkenylsulfonyl, heterocyclylalkynylsulfonyl, alkylsulfinyl, alkenylsulfinyl, alkynylsulfinyl, cycloalkylsulfinyl, cycloalkylalkyl-sulfinyl, cycloalkylalkenylsulfinyl, cycloalkylalkynylsulfinyl, arylsulfinyl, arylalkylsulfinyl, arylalkenylsulfinyl, arylalkynylsulfinyl, heteroarylsulfinyl, heteroarylalkylsulfinyl, heteroarylalkenylsulfinyl, heteroarylalkynylsulfinyl, heterocyclylsulfinyl, arylalkylsulfinyl, heterocyclalkenylsulfinyl, heterocylylalkynylsulfinyl, aminosulfonyl, unsubstituted or substituted mono- or dialkylaminosulfonyl, unsubstituted or substituted mono- or diarylaminosulfonyl, unsubstituted or substituted mono or diheteroarylaminosulfonyl, unsubstituted or substituted N-alkyl-N-arylaminosulfonyl, unsubstituted or substituted N-alkyl-N-heteroarylaminosulfonyl, alkylsulfonyloxy, alkenylsulfonyloxy, alkynylsulfonyloxy, cycloalkyl-sulfonyloxy, cycloalkylalkylsulfonyloxy, cycloalkylalkenylsulfonyloxy, cycloalkylalkynylsulfonyloxy, arylsulfonyloxy, arylalkylsulfonyloxy, arylalkenylsulfonyloxy, arylalkynylsulfonyloxy, heteroarylsulfonyloxy, heteroarylalkylsulfonyloxy, heteroaryl-alkenylsulfonyloxy, heteroaryl-alkynylsulfonyloxy, heterocyclylsulfonyloxy, heterocyclylalkyl-sulfonyloxy, heterocyclylalkenylsulfonyloxy, heterocyclylalkynyl-sulfonyloxy, alkylsulfonylamino, alkenylsulfonylamino, alkynylsulfonylamino, cycloalkylsulfonylamino, cycloalkalkylsulfoamino, cycloalkylalkenylsulfonylamino, cycloalkylalkynylsulfonylamino, arylsulfonylamino, arylalkylsulfonylamino, arylalkenylsulfonoamino, arylalkynylsylfonylamino, heteroarylsulfonylamino, heteroarylalkylsulfonylamino, heteroarylalkenylsulfonoamino, heteroarylalkynylsulfonylamino, alkylsulfonyl-N-alkylamino, alkenylsulfonyl-N-alkylamino, alkynylsulfonyl-N-alkylamino, cycloalkylsulfonyl-N-alkylamino, cycloalkylalkylsulfonyl-N-amino, cycloalkylalkenyl-sulfonyl-N-alkylamino, cycloalkylalkynylsulfonyl-N-alkylamino, arylsulfonyl-N-alkylamino, heteroarylsulfonyl-N-alkylamino, arylalkyl-sulfonyl-N-alkylamino, heteoarylalkylsulfonyl-N-alkylamino, aryl-alkenylsulfonoamino, heteroarylalkenylsulfonoamino, arylalkynyl-sulfonyl-N-alkylamino, heterorarylalkynylsulfonyl-N-alkylamino, heterocyclylsulfonyl-N-alkylamino, heterocyclylalkylsulfoamino, heterocyclylalkenylsulfonyl-N-alkylamino, heterocyclylalkynylsulfonyl-N-alkylamino, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, arylcarbonyl, arylalkylcarbonyl, alylalkenylcarbonyl, arylalkynylcarbonyl, heteroarylcarbonyl, heteroarylalkylcarbonyl, heteroarylalkenyl, heteroarylalkynylcarbonyl, heterocyclylcarbonyl, heterocyclyalkyl-carbonyl, heterocyclylalkenyl, heterocyclylalkynlycarbonyl, carboxyl, alkoxycarbonyl, alkenyloxycarbonyl, alkynyloxycarbonyl, cycloalkoxycarbonyl, cycloalkylalkoxycarbonyl, cycloalkylalkenyl-oxycarbonyl, cycloalkylalkynyloxycarbonyl, arylalkoxycarbonyl, arylalkoxycarbonyl, arylalkenyloxycarbonyl, arylalkynyloxycarbonyl, heteroaryloxycarbonyl, heteroarylalkoxycarbonyl, heteroarylalkenyl-oxycarbonyl, heteroarylalkynyloxycarbonyl, heterocyclyloxycarbonyl, heterocyclylalkoxycarbonyl, heterocyclylalkenyloxycarbonyl, heterocyclylalkynyloxycarbonyl, aminocarbonyl, unsubstituted or substituted mono- or dialkylaminocarbonyl, unsubstituted or substituted mono- or diarylaminocarbonyl, unsubstituted or substituted mono- or diheteroarylaminocarbonyl, unsubstituted or substituted N-alkyl-N-arylaminocarbonyl, unsubstituted or substituted N-alkyl-N-heteroarylaminocarbonyl, unsubstituted or substituted alkylcarbonylamino, unsubstituted or substituted alkylcarbonyl-N-alkylamino, unsubstituted or substituted arylcarbonylamino, unsubstituted or substituted arycarbonyl-N-arylamino, unsubstituted or substituted heteroarylcarbonylamino, unsubstituted or substituted heteroarylcarbonyl-N-heteroarylamino, unsubstituted or substituted alkylcarbonyl-N-alkylamino, unsubstituted or substituted arylcarbonyl-N-alkylamino, unsubstituted or substituted alkylcarbonyl-N-heteroarylamino, unsubstituted or substituted heteroarylcarbonyl-N-alkylamino, alkoxycarbonylamino, alkenyloxycarbonylamino, alkynyloxycarbonylamino, cycloalkoxycarbonylamino, cycloalkylalkoxycarbonylamino, cycloalkylalkenyloxycarbonylamino, cycloalkylalkynyloxycarbonylamino, aryloxycarbonylamino, arylalkoxycarbonylamino, arylalkenyloxycarbonylamino, arylalkynyloxycarbonylamino, heteroaryloxycarbonylamino, heteroarylalkoxycarbonylamino, heteroarylalkenyloxycarbonylamino, alkynyloxycarbonylamino, heterocyclyoxycarbonylamino, heterocyclylalkoxycarbonylamino, heterocyclylalkenyloxycarbonylamino, heterocyclylalkynyloxycarbonyl-amino, alkoxycarbonyl-N-alkylamino, alkenyloxycarbonyl-N-alkylamino, alkynyloxycarbonyl-N-alkylamino, cycloalkoxycarbonyl-N-alkylamino, cycloalkylalkoxycarbonyl-N-alkylamino, cycloalkyalkenyloxycarbonyl-N-alkylamino, cycloalkyalkynyloxycarbonyl-N-alkylamino, aryloxycarbonyl-N-alkylamino, aryloxycarbonyl-N-alkylamino, arylalkoxycarbonyl-N-alkylamino, arylalkenyloxycarbonyl-N-alkylamino, arylalkynyloxycarbonyl-N-alkylamino, heteroarylalkoxycarbonyl-N-alkylamino, heteroarylalkenyloxycarbonyl-N-alkylamino, heteroarylalkynyloxycarbonyl-N-alkylamino, heterocyclylalkoxycarbonyl-N-alkylamino, heterocyclylalkenyloxycarbonyl-N-alkylamino, heterocyclylalkynyloxycarbonyl-N-alkylamino, formyl, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfinyl, haloalkenylsulfinyl, haloalkynylsulfinyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkenyloxycarbonylamino, haloalkynyloxycarbonylamino, alkoxyalkoxy, arylalkoxyalkoxy, cyano, nitro, or a radical selected from the group consisting of alkyl-NH—N=CH—, aryl-$(CH_2)_n$—NH—N=CH—, alkoxy-N=CH—, aryl-$(CH_2)_n$—O—N=CH—, alkyl-NH—NH—CO— and arylalkyl-NH—NH—CO— and $R^5$ is heteroaryl, heterocyclyl or aryl, each of which is unsubstituted or mono- or polysubstituted by identical or different substituents selected from the group consisting of alkyl, alkenyl, alkynyl, cycloalkyl, cycloalkenyl, cycloalkylalkyl, cycloalkylalkenyl, cycloalkylalkynyl, aryl, arylalkyl, arylalkenyl, arylalkynyl, heteroaryl, heteroarylalkyl, heteroarylalkenyl, heteroarylalkynyl, heterocyclyl, heterocyclylalkyl, heterocyclylalkenyl, heterocyclylalkynyl, hydroxy, alkoxy, alkenyloxy, alkynyloxy, cycloalkoxy, cycloalkylalkoxy, cycloalkylalkenyloxy, cycloalkylalkynyloxy, cycloalkenyloxy, aryloxy, arylalkoxy, arylalkenyloxy, arylalkynyloxy, heteroaryloxy, heteroarylalkoxy, heteroarylalkenyloxy, heteroarylalkynyloxy, heterocyclyloxy, heterocyclylalkoxy, heterocyclylalkenyloxy, heterocyclylalkynyloxy, thio, alkylthio, alkenylthio, alkynylthio, cycloalkylthio, cycloalkylalkylthio, cycloalkylalkenylthio, cycloalkylalkynylthio, cycloalkenylthio, arylthio, arylalkylthio, arylalkenyltlio, arylalkynylthio, heteroarylthio, heteroarylalkylthio, heteroarylalkenylthio, heteroarylalkynylthio, heterocyclylthio, heterocyclylalkylthio, heterocyclylalkenylthio, heterocyclylalkynylthio, amino, unsubstituted or substituted mono- or dialkylamino, unsubstituted or substituted mono- or diarylamino, unsubstituted or substituted mono- or diheteroarylamino, unsubstituted or substituted N-alkyl-N-amino, unsubstituted or substituted N-alkyl-N-heteroarylamino, alkenylamino, alkynylamino, cycloalkylamino, cycloalkenylamino, heterocyclylalkylamino, heterocyclylalkenylamino, alkylsulfonyl, alkenylsulfonyl, alkynylsulfonyl, cycloalkylsulfonyl, cycloalkylalkylsulfonyl, cycloalkylalkenylsulfonyl, cycloalkylalkynylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynylsulfonyl, heterocyclylsulfonyl, heterocyclylalkylsulfonyl, heterocyclylalkenylsulfonyl, heterocyclylalkynylsulfonyl, alkylsulfinyl, alkenylsulfinyl, alkynylsulfinyl, cycloalkylsulfinyl, cycloalkylalkylsulfinyl, cycloalkylalkenylsulfinyl, cycloalkylalkynylsulfinyl, arylsulfinyl, arylalkylsulfinyl, arylalkenylsulfinyl, arylalkynylsulfinyl, heteroarylsulfinyl, heteroarylalkylsulfinyl, heteroarylalkenylsulfinyl, heteroarylalkynylsulfinyl, heterocyclylsulfinyl, arylalkylsulfinyl, heterocyclylalkenylsulfinyl, heterocyclylalkynylsulfinyl, aminosulfonyl, unsubstituted or substituted mono- or dialkylaminosulfonyl, unsubstituted or substituted mono- or diarylaminosulfonyl, unsubstituted or substituted mono- or diheteroarylaminosulfonyl, unsubstituted or substituted N-alkyl-N-arylaminosulfonyl, unsubstituted or substituted N-alkyl-N-heteroarylaminosulfonyl, alkylsulfonyloxy, alkenylsulfonyloxy, alkynylsulfonyloxy, cycloalkylsulfonyloxy, cycloalkylalkylsulfonyloxy, cycloalkylalkenylsulfonyloxy, cycloalkylalkynylsulfonyloxy, arylsulfonyloxy, arylalkylsulfonyloxy, arylalkenylsulfonyloxy, arylalkynylsulfonyloxy, heteroarylsulfonyloxy, heteroarylalkylsulfonyloxy, heteroarylalkenylsulfonyloxy, heteroarylalkynylsulfonyloxy, heterocyclylsulfonyloxy, heterocyclylalkylsulfonyloxy, heterocyclylalkenylsulfonyloxy, heterocyclylalkynylsulfonyloxy, alkylsulfonylamino, alkenylsulfonylamino, alkynylsulfonylamino, cycloalkylsulfonylamino, cycloalkylalkylsulfoamino, cycloalkylalkenylsulfonylamino, cycloalkylalkynylsulfonylamino, arylsulfonylamino, arylalkylsulfonylamino, arylalkenylsulfonoamino, arylalkynylsulfonylamino, heteroarylsulfonylamino, heteroarylalkylsulfonylamino, heteroarylalkenylsulfonoaminosulfonoamino, heteroarylalkynylsulfonylamino, alkylsulfonyl-N-alkylamino, alkenylsulfonyl-N-alkylamino, alkynylsulfonyl-N-alkylamino, cycloalkylsulfonyl-N-alkylamino, cycloalkylalkylsulfonyl-N-alkylamino, cycloalkylalkenylsulfonyl-N-alkylamino, cycloalkylalkynylsulfonyl-N-alkylamino, arylsulfonyl-N-alkylamino, heteroarylalkylsulfonyl-N-alkylamino, arylalkylsulfonyl-N-alkylamino, heteroarylsulfonyl-N-alkylamino, arylalkylsulfonyl-N-alkylamino, heteroarylalkenylsulfonyl-N-alkylamino, arylalkenylsulfonyl-N-alkylamino, heteroarylalkenylsulfonyl-N-alkylamino, arylalkynylsulfonyl-N-alkylamino, heteroarylalkynylsulfonyl-N-alkynylamino, heterocyclylsulfonyl-N-alkylamino, heterocyclylalkylsulfonyl-N-alkylamino, heterocyclylalkenylsulfonyl-N-alkylamino, heterocyclylalkynylsulfonyl-N-alkylamino, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenyl, heteroarylalkynylcarbonyl, heterocyclylcarbonyl, heterocyclylalkylcarbonyl, heterocyclylalkenyl, heterocyclylalkynylcarbonyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, aryloxycarbonyl, arylalkoxycarbonyl, arylalkenyloxycarbonyl, arylalkynyloxycarbonyl, heteroaryloxycarbonyl, heteroarylalkoxylcarbonyl, heteroarylalkenyloxycarbonyl, heteroarylalkynyloxycarbonyl, heterocyclyloxycarbonyl, heterocyclylalkoxycarbonyl, heterocyclylalkenyloxycarbonyl, heterocyclylalkynyloxycarbonyl, aminocarbonyl, unsubstituted or substituted mono- or dialkylaminocarbonyl, unsubstituted or substituted mono- or diarylaminocarbonyl, unsubstituted or substituted mono- or diheteroarylaminocarbonyl, unsubstituted or substituted N-alkyl-N-arylaminocarbonyl, unsubstituted or substituted N-alkyl-N-heteroarylaminocarbonyl, unsubstituted or substituted alkylcarbonylamino, unsubstituted or substituted alkylcarbonyl-alkylamino, unsubstituted or substituted arylcarbonylamino, unsubstituted or substituted arylcarbonyl-N-arylamino, unsubstituted or substituted heteroarylcarbonylamino, unsubstituted or substituted heteroarylcarbonyl-N-heteroarylamino, unsubstituted or substituted alkylcarbonyl-N-arylamino, unsubstituted or substituted arylcarbonyl-N-alkylamino, unsubstituted or substituted alkylcarbonyl-N-heteroarylamino, unsubstituted or substituted heteroarylcarbonyl-N-alkylamino, alkoxycarbonylamino, alkenyloxycarbonylamino, alkynyloxycarbonylamino, cycloalkoxycarbonylamino, cycloalkylalkoxycarbonylamino, cycloalkylalkenyloxycarbonylamino, cycloalkylalkynyloxycarbonylamino, aryloxycarbonylamino, arylalkoxycarbonylamino, arylalkenyloxycarbonylamino, arylalknyloxycarbonylamino, heteroaryloxycarbonylamino, heteroarylalkoxycarbonylamino, heteroarylalkenyloxycarbonylamino, heteroarylakynyloxycarbonylamino, heterocyclyloxycarbonylamino, heterocyclylalkoxycarbonylamino, heterocyclylalkenyloxycarbonylamino, heterocyclylalkynyloxycarbonylamino, alkoxycarbonyl-N-alkylamino, alkenyloxycarbonyl-N-alkylamino, alkynyloxycarbonyl-N-alkylamino, cycloalkoxcarbonyl-N-alkylamino, cycloalkylalkoxycarbonyl-N-alkylamino, cycloalkylalkenyloxycarbonyl-N-alkylamino, cycloalkylalkynyloxycarbonyl-N-alkylamino, aryloxycarbonyl-N-alkylamino, arylalkoxycarbonyl-N-alkylamino, arylalkenyloxycarbonyl-N-alkylamino, arylalkynyloxycarbonyl-N-alkylamino, heteroarylalkoxycarbonyl-N-alkylamino, heteroarylalkenyloxycarbonyl-N-alkylamino, heteroarylalkynyloxycarbonyl-N-alkylamino, heterocyclylalkoxycarbonyl-N-alkylamino, heterocyclylalkenyloxycarbonyl-N-alkylamino, heterocyclylalkynyloxycarbonyl-N-alkylamino, formyl, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfinyl, haloalkenylsulfinyl, haloalkynylsulfinyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxcarbonylamino, haloalkenyloxycarbonylamino, haloalkynyloxycarbonylamino, alkoxyalkoxy, arylalkoxyalkoxy, cyano, nitro, or a radical selected from the group consisting of alkyl-NH—N=CH—, aryl-$(CH_2)_n$—NH—N=CH—, alkoxy-N=CH—, aryl-$(CH_2)_n$—O—N=CH—, alkyl-NH—NH—CO— and arylalkyl-NH—NH—CO— and, or is a radical selected from the group consisting of —O—N=$CR^lR^m$, —P(=O)($OR^i$)($R^j$), —P(=O)($OR^i$)($OR^k$)

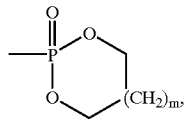

or, in the case that E is a bond and l is zero and Q is other than a radical of formula III where $G^1$–$G^2$ is $NR^{10}COR''$ then $R^5$ is also hydroxyl.

3. The compound as claimed in claim 1 in which $R^1$, $R^2$, $R^3$ independently of one another are hydrogen, halogen, nitro, cyano, alkyl, cycloalkyl, alkenyl, alkynyl, alkoxy, alkylthio, alkylsulfinyl, alkylsulfonyl, alkylsulfonyloxy, alkylsulfonylamino, alkylsulfonyl-N-alkylamino, phenyl, benyl, where the thirteen last-mentioned groups are unsubstitued or substituted by one or more idenfical or different radicals selected from the group consisting of halogen, nitro, cyano, alkyl, haloalkyl, cycloalkyl, alkenyl, alkynyl, alkoxy, haloalkoxy and alkylthio;

$R^4$ is hydrogen, cyano, alkyl, alkenyl, alkynyl, cycloalkyl, where the four last-mentioned groups are unsubstituted or substituted by one or more identical or different radicals selected from the group consisting of halogen, nitro, cyano, alkyl, cycloalkyl, alkynyl, alkoxy, alkylthio;

$R^5$ is a phenyl radical, a three-, five- or six-membered heteroaryl radical which may contain up to three heteroatoms selected from the group consisting of nitrogen, oxygen and sulfur, or a three- to six-membered saturated, partially saturated or unsaturated heterocycle radical which may contain up to four heteroatoms selected from the group consisting of nitrogen, oxygen and sulfur, each of which is unsubstituted or mono- or polysubstituted by identical or different substituents selected from the group consisting of halogen, nitro, cyano, formyl, amino, phenyl, benzyl, $(C_1-C_6)$-alkyl, $(C_2-C_6)$-alkenyl, $(C_2-C_6)$-alkynyl, $(C_3-C_6)$-cycloalkyl, $(C_1-C_6)$-alkoxy, $(C_1-C_6)$ alkylamino, di-$(C_1-C_6)$-alkylamino, $(C_1-C_6)$-alkoxycarbonyl, $(C_1-C_6)$-alkylaminocarbonyl, di-$(C_1-C_6)$-alkylaminocarbonyl, $(C_1-C_6)$-alkylcarbonyl, $(C_1-C_6)$-alkylcarbonylamino, $(C_1-C_6)$-alkylcarbonyl-$(C_1-C_6)$-alkylamino, $(C_1-C_6)$-alkylcarbonyl-di-$(C_1-C_6)$alkylamino, $(C_1-C_6)$-alkylthio, $(C_1-C_6)$-alkylsulfinyl, $(C_1-C_6)$-alkylsulfonyl, $(C_1-C_6)$-alkylsulfonylamino, $(C_1-C_6)$-alkylsulfonyl-$(C_1-C_6)$-alkylamino, $(C_1-C_6)$-alkylsulfonyl-di-$(C_1-C_6)$-alkylamino, where the 22 last-mentioned groups are unsubstituted or substitued by one or more identical or different radicals selected from the group consisting of halogen, nitro, cyano, $(C_1-C_6)$-alkyl, $(C_3-C_6$-cycloalkyl, $(C_2-C_6)$-alkenyl, $(C_2-C_6)$-alkynyl, $(C_1-C_6)$-alkoxy, $(C_1-C_6)$-alkylthio or by a three- to six-membered saturated, partially saturated or unsaturated heterocycle which may contain up to four heteroatoms selected from the group consisting of nitrogen, oxygen and sulfur, or is a radical selected from the group consisting of —O—N=$CR^lR^m$, —P(=O)($OR^i$)($R^j$), —P(=O)($OR^i$)($OR^k$) or

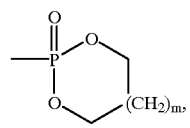

or, in the case that E is a bond and l is zero and Q is other than a radical of formula III where $G^1$–$G^2$ is $NR^{10}COR''$, then $R^5$ is also hydroxyl, A is a divalent unit selected from the group consisting of S, SO and $SO_2$;

B is a chain which has two carbon atoms which is saturated or contains a double bond and which is unsubstituted or substituted by alkyl, haloalkyl, alkoxy or haloalkoxy;

E is a bond, $CR^cR^d$, $NR^c$, S, SO, $SO_2$, O and CO;

$R^6$ is $(C_1-C_6)$-alkylthio, $(C_1-C_6)$-alkylsulfinyl, $(C_1-C_6)$-alkylsulfonyl, cyano, cyanato, thiocyanato, halogen or $OR^f$;

Y is a divalent unit selected from the group consisting of O, S, N—$(C_1-C_6)$-alkyl or $CHR^7$;

$R^7$ is hydrogen, $(C_1-C_6)$-alkyl, $(C_3-C_8)$-cycloalkyl, $(C_1-C_6)$-alkoxy, $(C_1-C_6)$-alkoxy-$(C_1-C_6)$-alkyl, $(C_1-C_6)$-alkylcarbonyl, $(C_1-C_6)$-alkoxycarbonyl, $(C_1-C_6)$-alkylthio, phenyl, where the hydrocarbon moiety of the eight last-mentioned radicals is unsubstituted or substituted by one or more identical or different radicals selected from the group consisting of halogen, $(C_1-C_3)$-alkylthio and $(C_1-C_3)$-alkyloxy;

Z is a bond, $CH_2$ or $CHR^7$;

$R^8$ is hydrogen, $(C_1-C_6)$-alkyl or $(C_1-C_6)$-alkoxycarbonyl;

$R^9$ is hydrogen, $(C_1-C_6)$-alkyl, $(C_3-C_8)$-cycloalkyl or halo-$(C_1-C_6)$-alkyl;

$R^{10}$ is hydrogen, $(C_1-C_6)$-alkyl, $(C_2-C_6)$-alkenyl, $(C_1-C_6)$-alkynyl, $(C_3-C_8)$-cycloalkyl, phenyl, benzyl, where the six last-mentioned radicals are unsubstituted or substituted by one or more identical or different radicals selected from the group consisting of halogen, cyano, nitro and $(C_1-C_6)$-alkoxy;

$R^{11}$ is hydrogen, formyl, $(C_1-C_6)$-alkyl, halo-$(C_1-C_6)$-alkyl, $(C_1-C_6)$-alkoxy-$(C_1-C_6)$-alkyl or a group L-$R^{12}$;

L is a divalent unit selected from the group consisting of $SO_2$, CO and $CHR^gCO$;

$R^{12}$ is $(C_1-C_6)$-alkyl, halo-$(C_1-C_6)$-alkyl, or phenyl which is unsubstituted or substituted by one or more identical or different radicals selected from the group consisting of cyano, nitro, $(C_1-C_3)$-alkyl, $(C_1-C_3)$-alkoxy, halo-$(C_1-C_3)$-alkyl and halo-$(C_1-C_3)$-alkoxy;

$R^c$ and $R^d$ independently of one another are hydrogen, halogen, nitro, cyano, $(C_1-C_6)$-alkyl, halo-$(C_1-C_6)$-alkyl, $(C_3-C_8)$-cycloalkyl, $(C_2-C_6)$-alkenyl, halo-$(C_2-C_6)$-alkenyl, $(C_2-C_6)$-alkynyl, halo-$(C_2-C_6)$-alkynyl, $(C_1-C_6)$-alkoxy, halo-$(C_1-C_6)$-alkoxy, $(C_1-C_6)$-alkylthio, halo-$(C_1-C_6)$-alkylthio, $(C_1-C_6)$-alkylcarbonyl, halo-$(C_1-C_6)$-alkylcarbonyl, $(C_1-C_6)$-alkoxycarbonyl, halo-$(C_1-C_6)$-alkoxycarbonyl, aminocarbonyl, and $(C_1-C_6)$-alkylsulfonyl;

$R^e$ is hydrogen, formyl, $(C_1-C_6)$-alkyl, $(C_3-C_8)$-cycloalkyl, $(C_2-C_6)$-alkenyl, $(C_2-C_6)$-alkynyl, $(C_1-C_6)$-alkylcarbonyl and $(C_1-C_6)$-alkylsulfonyl, where the hydrocarbon moiety of the six last-mentioned radicals may be unsubstituted or substituted by one or more identical or different radicals selected from the group consisting of halogen, nitro, cyano, $(C_1-C_6)$-alkyl, cycloalkyl, $(C_2-C_6)$-alkenyl, $(C_2-C_6)$-alkynyl, $(C_1-C_6)$-alkoxy and $(C_1-C_6)$-alkylthio;

$R^f$ is hydrogen, $(C_1-C_6)$-alkyl, halo-$(C_1-C_6)$-alkyl, $(C_1-C_6)$-alkylcarbonyl, $(C_1-C_6)$-alkoxycarbonyl, $(C_1-C_6)$-alkylsulfonyl, halo-$(C_1-C_6)$-alkylsulfonyl, benzoyl or phenylsulfonyl, where the aromatic moiety of the two last-mentioned radicals is unsubstituted or substituted by one or more identical or different radicals selected from the group consisting of $(C_1-C_6)$-alkyl, halo-$(C_1-C_6)$-alkyl, $(C_1-C_6)$-alkoxy, halo-$(C_1-C_6)$-alkoxy, halogen, cyano and nitro;

$R^g$ and $R^h$ independently of one another are hydogen or $(C_1-C_6)$-alkyl, and w is 0, 1, 2 or 3.

4. The compound as claimed in claim 1 in which $R^1$, $R^2$, $R^3$ independently of one another are hydrogen, halogen, nitro, cyano, $(C_1-C_6)$-alkyl, $(C_3-C_8)$-cycloalkyl, $(C_2-C_6)$-alkenyl, $(C_2-C_6)$-alkynyl, $(C_1-C_6)$-alkoxy, $(C_1-C_6)$-alkylthio, $(C_1-C_6)$-alkylsulfinyl, $(C_1-C_6)$-alkylsulfonyl, $(C_1-C_6)$-alkylsulfonyloxy, $(C_1-C_6)$-alkylsulfonylamino, $(C_1-C_6)$-alkylsulfonyl-N—$(C_1-C_6)$-alkylamino, phenyl, benzyl, where the thirteen last-mentioned groups are unsubstituted or substituted by one or more identical or different radicals selected from the group consisting of halogen, nitro, cyano, $(C_1-C_3)$-alkyl, halo-$(C_1-C_3)$-alkyl, cyclopropyl, $(C_2-C_4)$-alkenyl, $(C_2-C_4)$-alkynyl, $(C_1-C_3)$-alkoxy, halo-$(C_1-C_3)$-alkoxy and alkylthio;

$R^4$ is $(C_1-C_4)$-alkyl, hydrogen, cyano, $(C_2-C_4)$-alkenyl, $(C_2-C_4)$-alkynyl, $(C_3-C_6)$-cycloalkyl, where the three last-mentioned groups are unsubstituted or substituted by one or more identical or different radicals selected from the group consisting of halogen, cyano, $(C_1-C_3)$-alkoxy, $(C_1-C_3)$-alkylthio, and where the group mentioned first is unsubstituted or substituted by one or more identical or different radicals selected from the group consisting of halogen, cyano, $(C_3-C_6)$-cycloalkyl, $(C_1-C_3)$-alkoxy, $(C_1-C_3)$-alkylthio;

$R^5$ is a phenyl radical, a three-, five- or six-membered heteroaryl radical which may contain up to three heteroatoms selected from the group consisting of nitrogen, oxygen and sulfur, or a three- to six-membered saturated, partially saturated or unsaturated heterocycle radical which may contain up to four heteroatoms selected from the group consisting of nitrogen, oxygen and sulfur, each of which is unsubstituted or mono- or polysubstituted by identical or different substituents selected from the group consisting of halogen, nitro, cyano, formyl, amino, phenyl, benzyl, $(C_1-C_4)$-alkyl, $(C_2-C_4)$-alkenyl, $(C_2-C_4)$-alkynyl, $(C_3-C_6)$-cycloalkyl, $(C_1-C_4)$-alkoxy, $(C_1-C_4)$-alkylamino, di-$(C_1-C_4)$-alkylamino, $(C_1-C_4)$-alkoxycarbonyl, $(C_1-C_4)$-alkylaminocarbonyl, di-$(C_1-C_4)$-alkylaminocarbonyl, $(C_1-C_4)$-alkylcarbonyl, $(C_1-C_4)$-alkylcarbonylamino, $(C_1-C_4)$-alkylthio, $(C_1-C_4)$-alkylsulfinyl, $(C_1-C_4)$-alkylsulfonyl or is a radical selected from the group consisting of —O—N=$CR^lR^m$, —P(=O)(O$R^i$)($R^j$), —P(=O)(O$R^i$)(O$R^k$) or

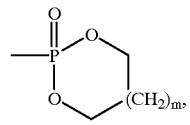

or, in the case that E is a bond that l is zero and Q is other than a radical of formula III where $G^1$–$G^2$ is NR$^{10}$COR", then $R^5$ is also hydroxyl, A is a divalent unit selected from the group consisting of S, SO, and SO$_2$;

B is a chain which has two carbon atoms which is saturated or contains a double bond and which is unsubstituted or substituted by one or two identical or different radicals selected from the group consisting of $(C_1-C_3)$-alkyl, halo-$(C_1-C_3)$-alkyl, $(C_1-C_3)$-alkoxy or halo-$(C_1-C_3)$-alkoxy;

E is a bond, $CR^cR^d$, SO$_2$ and CO;

$R^6$ is $(C_1-C_3)$-alkylthio, $(C_1-C_3)$-alkylsulfonyl, cyano, cyanato, thiocyanato, halogen or O$R^f$;

Y is a divalent unit selected from the group consisting of O and CH$R^7$;

$R^7$ is hydrogen, $(C_1-C_6)$-alkyl, $(C_3-C_6)$-cycloalkyl, $(C_1-C_6)$-alkoxy-$(C_1-C_6)$-alkyl, $(C_1-C_6)$-alkylcarbonyl, $(C_1-C_6)$-alkoxyarbonyl, phenyl, where the six last-mentioned radicals are unsubstituted or substituted by one or more identical of different halogen atoms;

$R^9$ is $(C_1-C_6)$-alkyl, $(C_3-C_6)$-cycloalkyl or halo-$(C_1-C_6)$-alkyl;

$R^{10}$ is $(C_1-C_6)$-alkyl, $(C_2-C_6)$-alkenyl, $(C_2-C_6)$-alkynyl, $(C_3-C_8)$-cycloalkyl, phenyl or benzyl;

$R^{11}$ is hydrogen, $(C_1-C_6)$-alkyl or a group L-$R^{12}$;

$R^c$ and $R^d$ independently of one another are hydrogen, $(C_1-C_3$-alkyl, halo-$(C_1-C_3)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_1-C_3)$-alkoxy, halo-$(C_1-C_3)$-alkoxy, $(C_1-C_3)$-alkylthio, halo-$(C_1-C_3)$-alkylthio and $(C_1-C_3)$-alkylcarbonyl;

$R^f$ is hydrogen, $(C_1-C_6)$-alkyl, $(C_1-C_6)$-alkylcarbonyl, $(C_1-C_6)$-alkoxycarbonyl, $(C_1-C_6)$-alkylsulfonyl, benzoyl or phenylsulfonyl, where the aromatic moiety of the two last-mentioned radicals is unsubstituted or substituted by one or more identical or different radicals selected from the group consisting of $(C_1-C_6)$-alkyl, halo-$(C_1-C_6)$-alkyl, $(C_1-C_6)$-alkoxy, halo-$(C_1-C_6)$-alkoxy, halogen, cyano and nitro, and w is 0, 1 or 2.

5. The compound as claimed in claim 1 in which

Q is a radical of the formula (II) or (III)

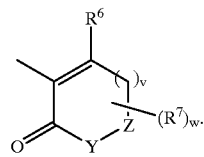
(II)

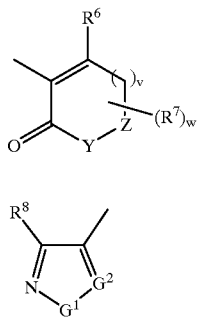
(III)

6. The compound as claimed in claim 1 in which $R^1$ and $R^2$ independently of one another are hydrogen, $(C_1-C_4)$-alkyl, halogen or nitro;

$R^3$ and $R^4$ are hydrogen;

A is $SO_2$;

B is $CH_2-CH_2$;

E is a bond or a divalent unit selected from the group consisting of $CH_2$, CO and $SO_2$;

$R^6$ is $OR^f$;

Y is $CHR^7$;

Z is $CHR^7$;

$G^1-G^2$ is a divalent unit selected from the group consisting of $OCR^9$ and $NR^{10}COR^{11}$;

$R^7$ is hydrogen or $(C_1-C_6)$-alkyl;

$R^8$ is hydrogen;

$R^9$ is $(C_3-C_6)$-cycloalkyl;

$R^{10}$ is $(C_1-C_3)$-alkyl;

$R^{11}$ is hydrogen or a group $L-R^{12}$;

L is a divalent unit selected from the group consisting of $SO_2$, CO and $CH_2CO$;

$R^{12}$ is phenyl which is unsubstituted or substituted by one or more identical or different radicals selected from the group consisting of halogen, cyano, nitro, $(C_1-C_6)$-alkyl, $(C_1-C_6)$-alkoxy, $(C_1-C_6)$-haloalkyl and $(C_1-C_6)$-haloalkoxy;

$R^e$ is hydrogen, formyl, $(C_1-C_6)$-alkyl, $(C_2-C_6)$-alkenyl, $(C_2-C_6)$-alkynyl, $(C_1-C_6)$-alkylcarbonyl and $(C_1-C_6)$-alkylsulfonyl;

$R^f$ is hydrogen, $(C_1-C_6)$-alkylsulfonyl, benzoyl, phenylsulfonyl, where the two last-mentioned radicals are unsubstituted or substituted by one or more identical or different radicals selected from the group consisting of $(C_1-C_6)$-alkyl, $(C_1-C_6)$-haloalkyl, $(C_1-C_6)$-alkoxy, $(C_1-C_6)$-haloalkoxy, halogen, cyano and nitro, and v is 1.

7. The compound as claimed in claim 1 in which Q is the radical of the formula (II)

8. The compound as claimed in claim 1 in which $R^5$ is a phenyl radical, a three-, five- or six-membered heteroaryl radical which may contain up to three heteroatoms selected from the group consisting of nitrogen, oxygen and sulfur, a three-, five- or six-membered heteroaryl radical which may contain up to three heteroatoms selected from the group consisting of nitrogen, oxygen and sulfur, or a three- to six-membered partially saturated or unsaturated heterocycle radical which may contain one, two, three or four heteroatoms selected from the group consisting of nitrogen, oxygen and sulfur, each of which is unsubstituted or mono- or polysubstituted by identical or different substituents selected from the group consisting of halogen, nitro, cyano, formyl, amino, phenyl, benzyl, $(C_1-C_4)$-alkyl, $(C_2-C_4)$-alkenyl, $(C_2-C_4)$-alkynyl, $(C_3-C_6)$-cycloalkyl, $(C_1-C_4)$-alkoxy, $(C_1-C_4)$-alkylamino, di-$(C_1-C_4)$-alkylamino, $(C_1-C_4)$-alkoxycarbonyl, $(C_1-C_4)$-alkylaminocarbonyl, di-$(C_1-C_4)$-alkylaminocarbonyl, $(C_1-C_4)$-alkylcarbonyl, $(C_1-C_4)$-alkylcarbonylamino, $(C_1-C_4)$-alkylthio, $(C_1-C_4)$-alkylsulfinyl, $(C_1-C_4)$-alkylsulfonyl.

9. A herbicidal composition which comprises at least one compound of the formula (I) as claimed in claim 1.

10. The herbicidal composition as claimed in claim 9 as a mixture with formulation auxiliaries.

11. A method for controlling undesirable plants, which comprises applying an effective amount of at least one compound of the formula (I) as claimed in any of claim 1 or a herbicidal composition as claimed in claim 9 to the plants or the location of the undesirable plant growth.

12. A method for use of compounds of the formula (I) as claimed in claim 1 or of herbicidal compositions as claimed in claim 9 for controlling undesirable plants.

13. A method for use as claimed in claim 12, wherein the compounds of the formula (I) are employed for controlling undesirable plants in crops of useful plants.

14. A method for use as claimed in claim 13, wherein the useful plants are transgenic useful plants.

15. The compound of the formula (Ig),

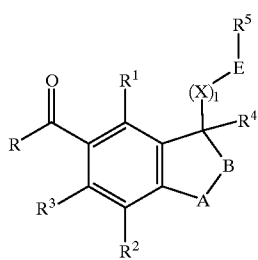
Ig in which

R is $(C_1-C_6)$-alkyl, $R^4$ is hydrogen, $R^5$ is COOH, COOR, COCl, CH=NOH, CHO, E is a bond, l is 0, and $R^1$, $R^2$, $R^3$, A and B are as defined in any of claims 1 to 8.

16. A method for use of the compounds as claimed in claim 15 for preparing compounds as claimed in claim 1.

* * * * *